(12) United States Patent
Pevarello et al.

(10) Patent No.: US 8,563,550 B2
(45) Date of Patent: Oct. 22, 2013

(54) IMIDAZOLOTHIADIAZOLES FOR USE AS PROTEIN KINASE INHIBITORS

(75) Inventors: Paolo Pevarello, Bresso (IT); Ana Maria Garcia Collazo, Madrid (ES); Ana Belen Garcia Garcia, Madrid (ES)

(73) Assignee: Centro Nacional de Investigaciones Oncologicas (CNIO)

( * ) Notice: Subject to any disclaimer, the term of this patent is extended or adjusted under 35 U.S.C. 154(b) by 304 days.

(21) Appl. No.: 12/679,514

(22) PCT Filed: Sep. 29, 2008

(86) PCT No.: PCT/GB2008/003287
§ 371 (c)(1),
(2), (4) Date: Apr. 6, 2011

(87) PCT Pub. No.: WO2009/040552
PCT Pub. Date: Apr. 2, 2009

(65) Prior Publication Data
US 2011/0190289 A1 Aug. 4, 2011

(30) Foreign Application Priority Data
Sep. 27, 2007 (EP) .................................. 07381066

(51) Int. Cl.
*A61K 31/5377* (2006.01)
*A61K 31/433* (2006.01)
*A61K 31/4439* (2006.01)
*A61K 31/497* (2006.01)
*C07D 513/04* (2006.01)

(52) U.S. Cl.
USPC ... 514/233.2; 514/363; 514/338; 514/255.05; 548/126; 546/268.7; 544/134

(58) Field of Classification Search
None
See application file for complete search history.

(56) References Cited

U.S. PATENT DOCUMENTS

| | | | |
|---|---|---|---|
| 4,709,031 A | 11/1987 | Ingendoh et al. | |
| 2007/0049591 A1 | 3/2007 | Pinkerton et al. | |
| 2007/0093490 A1 | 4/2007 | Prien et al. | |

FOREIGN PATENT DOCUMENTS

| | | |
|---|---|---|
| CN | 101037445 | 9/2007 |
| EP | 0041215 | 5/1981 |
| EP | 0088323 | 2/1983 |
| EP | 662 477 | 1/1995 |
| GB | 1 464 259 | 2/1977 |
| WO | 97/11075 | 9/1996 |
| WO | 02/12250 | 2/2002 |
| WO | 03/051890 | 6/2003 |
| WO | 2004/111060 | 6/2004 |
| WO | 2004/058769 | 7/2004 |
| WO | WO-2004/078110 A2 | 9/2004 |
| WO | WO-2004/111061 A1 | 12/2004 |
| WO | WO-2006/128692 A2 | 12/2006 |
| WO | 2007/118318 | 4/2007 |
| WO | 2007/064797 | 6/2007 |
| WO | 2007/136730 | 11/2007 |
| WO | 2008/138834 | 11/2008 |
| WO | WO-2008/144767 A1 | 11/2008 |
| WO | 2009/040552 | 4/2009 |
| WO | 2010/012345 | 2/2010 |

OTHER PUBLICATIONS

Compound CAS RN 342782-02-9_(2001).*
Hegde et al., Journal of Sulfur Chemistry (2006), 27(6), p. 553-569.*
Abdel-Magid A. F., et al., J. Org. Chem., (1996), vol. 61, p. 3849.
Abdel-Magid A. F., et al., Synthesis, (1998) p. 537.
Abignente, et al., Il Farmaco, (1990), vol. 45, p. 1075.
Andanappa K. Gadad, et al., Bioorg. Med. Chem, (2004), vol. 12, pp. 5651-5659.
Asuncion Malin, et al., Farmaco, (1992), vol. 47(1), pp. 63-75.
Bellamy F.D., et al., Tetrahedron Letters, (1984), vol. 25, p. 839.
Bretonnet, et al., J. Med. Chem. (2007), vol. 50, p. 1872.
Cohen, Current Opinion in Chemical Biology, (1999), vol. 3, pp. 459-465.
Defacqz N., et al., Tetrahedron :Letters, (2003), vol. 44, p. 9111.
Dehuri S. N., et al., Journal of the Indian Chemical Society (1982), vol. 59(10), pp. 1170-1173.
Dermer O. C., Chem. Rev., (1934) vol. 14, p. 385.
El-Sherbeny M.A., et al., Boll. Chim. Farm., (1997), vol. 136, pp. 253-256.
Fabio P.F., et al., Journal of Labelled Compounds and Pharmaceuticals, (1978), vol. 15, p. 407.
Gregson S.J., et al., J. Med. Chem., (2004), vol. 47, p. 1161.
Han S. Y., et al.., Tetrahedron, (2004), vol. 60, p. 2447.
Hennessey, et al., Nature Rev. Drug Discovery 4: (2005), pp. 988-1004.
Ikemoto T., et al., Heterocycles, (2001), vol. 55, p. 99.
Ikemoto T., et al., Tetrahedron; (2000), vol. 56, p. 7915.
Katso, et al., Annu. Rev. Cell. Deg. Boil., (2001), vol. 17, pp. 615-675.

(Continued)

*Primary Examiner* — Yong Chu
(74) *Attorney, Agent, or Firm* — McCarter & English, LLP; Steven G. Davis; Daniel A. Wespe

(57) ABSTRACT

There is provided compounds of formula (I), wherein Z, M, $R^1$, X, $R^2$, $R^3$ and B have meanings given in the description, and pharmaceutically-acceptable esters, amides, solvates or salts thereof, which compounds are useful in the treatment of diseases in which inhibition of a protein kinase (e.g. a PIM family kinase or PI3-K) is desired and/or required, and particularly in the treatment of cancer.

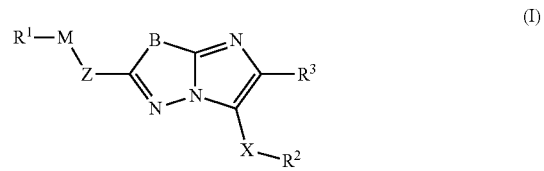

(I)

22 Claims, No Drawings

(56) References Cited

OTHER PUBLICATIONS

Kobe J., et al., Tetrahedra, (1968), vol. 24, p. 239.
Kuwahara M., et al., Chem. Pham Bull., (1996), vol. 44, p. 122.
Lainton J. A. H., et al., J. Comb. Chem., (2003), vol. 5, p. 400.
Leslie, et al., Chem Rev., (2001), vol. 101(8), pp. 2365-2380.
Parsons, et al., Nature 436:(2005), p. 792.
Paul Heinz, et al., Monatshefte für Chemie, (1977), vol. 108, pp. 665-680.
Plotkin M., et al., Tetrahedron Letters, (2000), vol. 41, p. 2269.
Schlosser M., et al., Organometallics in Synthesis. A Manual, (M. Schlosser, Ed.), Wiley & Sons Ltd: Chichester, UK, (2002).
Severinsen R., et al., Tetrahedron, (2005), vol. 61, pp. 5565-5575.
Seyden-Penne J., Reductions by the Alumino and Borohydrides, VCH, NY, (1991).
Shintani, R., et al., Org. Letters, (2005), vol. 7(21), pp. 4757-4759.
Terzioglu, et al., Eur. J. of Med. Chem. (2003), vol. 38(7-8), pp. 781-786.
Toker, et al., Cell. Mol. Life Sci., (2002), vol. 59(5), pp. 761-779.
Vanhaesebroeck, et al., Exp. Cell. Res., (1999), vol. 25(1), pp. 239-254.
Vanhaesebroeck, et al., Trends Biochem. Sci., (1997), vol. 22(7), pp. 267-272.
Wenwei L., et al., Tetrahedron Letters; (2006); vol. 47, p. 1941.
Werber G., et al., J. Heterocycl. Chem.; 14; (1977); pp. 823-827.
Wiggins J. M., et al., Synth. Commun., (1988), vol. 18, p. 741.
Wipf P., et al., J. Org. Chem., (2000), vol. 65(20), pp. 6318-6337.
Terzioglu et al, European Journal of Medicinal Chemistry (2003), 38(7-8), pp. 781-786.
Andreani et al., Arzneimittel-Forschung (2000), 50(6), pp. 550-553.
Journal of the Indian Chemical Society (1979), 56(7), pp. 716-717.
Abignente et al, Farmaco, Edizione Scientifica (1985), 40(3), pp. 190-199.
XP-002470755, Deburi, S. N. et al. "Studies on heterocyclic compounds. Part V. synthesis and antimicrobial activities of N-bridged thiazole and imidazole derivatives" (1982) Database Accession No. 1983:179345.
Kolavi et al. Bioorg. Med. Chem. 2006, 14, 3069-3080.
Zhang et al. Chem. J. Chinese U. 2002, 23, 1882-1886.

* cited by examiner

IMIDAZOLOTHIADIAZOLES FOR USE AS PROTEIN KINASE INHIBITORS

FIELD OF THE INVENTION

This invention relates to novel pharmaceutically-useful compounds, which compounds are useful as inhibitors of protein kinases (such as PI3Ks and the PIM family kinases). The compounds are of potential utility in the treatment of diseases such as cancer. The invention also relates to the use of such compounds as medicaments, to pharmaceutical compositions containing them, and to synthetic routes for their production.

BACKGROUND OF THE INVENTION

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, *Current Opinion in Chemical Biology* 1999, 3, 459-465.

PIM-1 is the protooncogene activated by murine leucemia virus (Provirus Integration site for Moloney murine leucemia virus—MoMuLV) that induces T-cell lymphoma [Cuypers, H. T., et. al. *Cell,* 1984, 37, 141-150].

The expression of the protooncogene produces a non-transmembrane serine/threonine kinase of 313 residues, including a kinase domain consisting of 253 amino acid residues. Two isoforms are known through alternative initiation (p44 and p33) [Saris, C. J. M. et al. *EMBO J.* 1991, 10, 655-664].

PIM-1, PIM-2 and PIM-3 phosphorylate protein substrates that are important in cancer neogenesis and progression. For example, PIM-1 phosphorylates inter alia p21, Bad, c-myb, Cdc 25A and eIF4B (see e.g. Quian, K. C. et al, *J. Biol. Chem.* 2005, 280(7), 6130-6137, and references cited therein).

Two PIM-1 homologs have been described [Baytel, D. *Biochem. Biophys. Acta* 1998, 1442, 274-285; Feldman, J. et al. *J. Biol. Chem.* 1998, 273, 16535.16543]. PIM-2 and PIM-3 are respectively 58% and 69% identical to PIM-1 at the amino acid level. PIM-1 is mainly expressed in thymus, testis, and cells of the hematopoietic system [Mikkers, H.; Nawijn, M.; Allen, J.; Brouwers, C.; Verhoeven, E.; Jonkers, J.; Berns, *Mol. Cell. Biol.* 2004, 24, 6104; Bachmann, M.; Moroy, T. *Int. J. Biochem. Cell Biol.* 2005, 37, 726-730. 6115]. PIM-1 expression is directly induced by STAT (Signal Transducers and Activators of Transcription) transcription factors, and PIM-1 expression is induced by many cytokine signalling pathways such as interleukins (IL), granulocyte-macrophage colony stimulating factor (GM-CSF), α- and γ-interferon, erythropoietin, and prolactin [Wang, Z et al. *J. Vet. Sci.* 2001, 2, 167-179].

PIM-1 has been implicated in lymphoma development. Induced expression of PIM-1 and the protooncogene c-myc synergise to increase the incidence of lymphomagenesis [Breuer, M. et al. Nature 1989, 340, 61-63; van Lohuizen M. et al. Cell, 1991, 65, 737-752]. PIM-1 functions in cytokine signalling pathways and has been shown to play a role in T cell development [Schmidt, T. et al. EMBO J. 1998, 17, 5349-5359; Jacobs, H. et al. JEM 1999, 190, 1059-1068]. Signalling through gp130, a subunit common to receptors of the IL-6 cytokine family, activates the transcription factor STAT3 and can lead to the proliferation of hematopoietic cells [Hirano, T. et al. Oncogene 2000, 19, 2548-2556]. A kinase-active PIM-1 appears to be essential for the gp130-mediated STAT3 proliferation signal. In cooperation with the c-myc PIM-1 can promote STAT3-mediated cell cycle progression and antiapoptosis [Shirogane, T. et sl., immunity, 1999, 11, 709-719]. PIM-1 also appears to be necessary for IL-3-stimulated growth in bone marrow-derived mast cells [Domen, J. et al., Blood, 1993, 82, 1445-1452] and survival of FDCP1 cells after IL-3 withdrawal [Lilly, M. et al., Oncogene, 1999, 18, 4022-4031].

Additionally, control of cell proliferation and survival by PIM-1 may be effected by means of its phosphorylation of the well-established cell cycle regulators cdc25 [Mochizuki, T. et al., J. Biol. Chem. 1999, 274, 18659-18666] and/or p21(Cip1/WAF1) [Wang Z. et al. Biochim. Biophys. Acta 2002, 1593, 45-55] or phosphorylation of heterochromatin protein 1, a molecule involved in chromatin structure and transcriptional regulation [Koike, N. et al, FEBS Lett. 2000, 467, 17-21].

Mice deficient for all three PIM genes showed an impaired response to hematopoietic growth factors and demonstrated that PIM proteins are required for efficient proliferation of peripheral T lymphocytes. In particular, it was shown that PIM function is required for efficient cell cycle induction of T cells in response to synergistic T-cell receptor and IL-2 signalling. A large number of interaction partners and substrates of PIM-1 have been identified, suggesting a pivotal role for PIM-1 in cell cycle control, proliferation, as well as in cell survival.

The oncogenic potential of this kinase has been first demonstrated in E μ PIM-1 transgenic mice in which PIM-1 over-expression is targeted to the B-cell lineage which leads to formation of B-cell tumors [van Lohuizen, M. et al.; *Cell* 1989, 56, 673-682. Subsequently PIM-1 has been reported to be over-expressed in a number of prostate cancers, erythro-leukemias, and several other types of human leukemias [Roh, M. et al.; *Cancer Res.* 2003, 63, 8079-8084; Valdman, A. et al; *Prostate* 2004, 60, 367-371.

For example, chromosomal translocation of PIM-1 leads to overexpression of PIM-1 in diffuse large cell lymphoma. [Akasaka, H. et al.; *Cancer Res.* 2000, 60, 2335-2341]. Furthermore, a number of missense mutations in PIM-1 have been reported in lymphomas of the nervous system and AIDS-induced non-Hodgkins' lymphomas that probably affect PIM-1 kinase activity or stability [Pasqualucci, L. et al, *Nature* 2001, 412, 341-346; Montesinos-Rongen, M. et al., *Blood* 2004, 103, 1869-1875; Gaidano, G. et al., *Blood* 2003, 102, 1833-184]. Thus, the strong linkage between reported overexpression data and the occurrence of PIM-1 mutations in cancer suggests a dominant role of PIM-1 in tumorigenesis.

Several other protein kinases have been described in the literature, in which the activity and/or elevated activity of such protein kinases have been implicated in diseases such as cancer, in a similar manner to PIM-1, PIM-2 and PIM-3. Such protein kinases include PI3-K, CDK-2, SRC and GSK-3.

There is a constant need to provide alternative and/or more efficacious inhibitors of protein kinases, and particularly inhibitors of CDK-2, SRC, GSK-3, PI3-K, PIM-1, PIM-2 and/or PIM-3. Such modulators are expected to offer alternative and/or improved approaches for the management of medical conditions associated with activity and/or elevated activity of CDK-2, SRC, GSK-3, PI3-K, PIM-1, PIM-2 and/or PIM-3 protein kinases The listing or discussion of an apparently prior-published document in this specification should not necessarily be taken as an acknowledgement that the document is part of the state of the art or is common general knowledge.

International patent application WO 2007/064797 discloses various compounds that may be useful in the treatment of cancer. However, there is no mention in that document of imidazothiadiazoles.

US patent applications US 2007/0049591 and US 2007/0093490 and international patent application WO 2004/058769 all disclose various compounds that may be useful as kinase inhibitors. Further, international patent application WO 2007/0136736 discloses various compounds that may be useful as Lck inhibitors. However, all these documents only mention compounds in which the core ring structure is a 6,5-ring system.

International patent application WO 2004/111060 discloses various imidazothiadiazoles that may be useful in the treatment of neurodegenerative diseases and cancer. However, this document primarily relates to 6-aryl substituted imidazo[2,1-b]-1,3,4-thiadiazoles, substituted in the 2-position with a sulfur (or oxidised derivative thereof) linker group. Further, international patent application WO 03/051890 also discloses various imidazothiadiazoles, which may be useful in the treatment of neurodegenerative diseases and cancer. However, this document primarily relates to 6-aryl substituted imidazo[2,1-b]-1,3,4-thiadiazoles, substituted in the 2-position with a sulfonamide group.

Journal article *European Journal of Medicinal Chemistry* (2003), 38(7-8), 781-786 by Terzioglu et al discloses various compounds that may be useful in the treatment of cancer. However, this document only discloses compounds that contain a carbohydrazide moiety.

Italian journal article *Arzneimittel-Forschung* (2000), 50(6), 550-553 by Andreani et al discloses various compounds including specific imidazothiadiazoles. However, there is no mention in this journal article that the compounds disclosed therein may be useful as protein kinase inhibitors.

International patent application WO 97/11075 discloses various compounds imidazothiadiazoles as herbicides. However, there is no disclosure that such compounds may be useful as pharmaceuticals, e.g. in the treatment of cancer.

European patent application EP 662 477 and journal article *Journal of the Indian Chemical Society* (1979), 56(7), 716-17 by Joshi et al, both disclose various heterobicyclic compounds, including specific imidazolothiadiazole compounds, which may be active as fungicides. However, there is no disclosure in either of these documents that the compounds disclosed therein may be useful as protein kinase inhibitors.

Italian journal article *Farmaco, Edizione Scientifica* (1985), 40(3), 190-9 by Abignente et al and European patent application EP 41215 both disclose various imidazolothiadiazoles, which may have been tested for medicinal properties for research purposes.

Various imidazolothiadiazoles have also been disclosed in *Journal of the Indian Chemical Society* (1982), 59(10), 1170-3 as potential fungicides and/or bactericides.

Various other imidazolothiadiazoles have also been disclosed in the CAS registry database, but to which compounds no use has apparently been ascribed.

DISCLOSURE OF THE INVENTION

According to the invention, there is provided a compound of formula I,

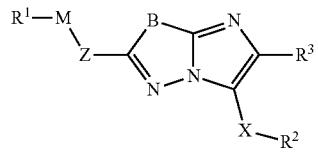

wherein:
B represents —S—, —S(O)— or —SO$_2$—;
Z represents a direct bond, —(CH$_2$)$_n$—O—, —(CH$_2$)$_n$—S—, —(CH$_2$)$_n$—N(R$^a$)—, —(CH$_2$)$_{n1}$—S(O)—, —(CH$_2$)$_n$—SO$_2$—, —(CH$_2$)$_n$—NH—SO$_2$—, —(CH$_2$)$_{n1}$—SO$_2$—NH—, —(CH$_2$)$_n$—N(R$^a$)—CO—, —(CH$_2$)$_n$—NH—CO—NH— or —(CH$_2$)$_n$—CO—N(R$^a$)—;
n represents, on each occasion when used herein, 0, 1 or 2;
n1 represents, on each occasion when used herein, 1 or 2;
M represents a direct bond or C$_{1-8}$ alkylene optionally substituted by one or more substituents independently selected from halo, —OR$^b$, —SR$^b$ or —N(R$^b$)$_2$;
R$^1$ represents hydrogen, halogen, —CN, —CO$_2$H, C$_{1-8}$ alkyl (optionally substituted by one or more substituents selected from A$^1$), C$_{3-6}$ cycloalkyl, heterocycloalkyl (which latter two groups are optionally substituted by one or more substituents selected from B$^1$ and B$^2$, respectively) aryl or heteroaryl (which latter two groups are optionally substituted with one or more substituents selected from B$^3$ and B$^4$, respectively);
X represents a direct bond, —(CH$_2$)$_m$—O—, —(CH$_2$)$_m$—S—, —(CH$_2$)$_m$—N(R$^d$)—, —S(O)—, —(CH$_2$)$_m$—SO$_2$—, —(CH$_2$)$_m$—NH—SO$_2$—, —(CH$_2$)$_m$—SO$_2$—NH—, —(CH$_2$)$_m$—NH—CO—, —(CH$_2$)$_m$—CO—N(R$^d$)—, —(CH$_2$)$_m$—NH—CO—NH— or C$_{1-8}$ alkylene optionally substituted by one or more substituents selected from A$^2$;
m represents, on each occasion when used herein, 0, 1 or 2;
R$^2$ represents hydrogen, halo, —CO$_2$H, C$_{1-8}$ alkyl (optionally substituted by one or more substituents selected from A$^3$) or -T-Q;
T represents a direct bond or a C$_{1-3}$ alkylene linker group optionally substituted by one or more substituents selected from A$^4$;
Q represents C$_{3-6}$ cycloalkyl, heterocycloalkyl (which latter two groups are optionally substituted by one or more substituents selected from B$^5$ and B$^6$, respectively), aryl or heteroaryl (which latter two groups are optionally substituted by one or more substituents selected from B$^7$ and B$^8$, respectively);
but wherein:
(i) when X represents a direct bond, then R$^2$ does not represent hydrogen or halo; and
(ii) when Z and M both represent direct bonds, then R$^1$ does not represent hydrogen; and
(iii) when either Z and M represent direct bonds, then R$^1$ does not represent halo;
A$^1$, A$^2$, A$^3$ and A$^4$ independently represent halo, —OR$^e$, —S—C$_{1-4}$ alkyl, —N(R$^e$)$_2$, —C(O)$_2$R$^e$, —C(O)N(R$^e$)$_2$, —N(R$^e$)—C(O)—R$^e$, —C(O)R$^e$, —CN, —SO$_2$N(R$^e$)$_2$ and/or phenyl (optionally substituted by one or more halo and/or —OR$^e$ substituents);
B$^1$, B$^2$, B$^3$, B$^4$, B$^5$, B$^6$, B$^7$ and B$^8$ independently represent halo, —OR$^e$, —C(O)$_2$R$^e$, —C(O)R$^e$, —C(O)N(R$^e$)$_2$, —N(R$^e$)—C(O)—R$^e$, —CN, —S(O)$_2$R$^e$, —S(O)$_2$N(R$^e$)$_2$, —N(R$^e$)$_2$ and/or C$_{1-4}$ alkyl optionally substituted by one or more substituents selected from halo, —OR$^e$ and —C(O)$_2$R$^e$; or,
B$^1$, B$^2$, B$^5$ and B$^6$ may alternatively and independently represent =O;

$R^3$ represents hydrogen, halo, —$R^f$, —$OR^f$, —$SR^f$, cyano or —$N(R^f)_2$;

$R^a$, $R^b$, $R^d$, $R^e$ and $R^f$ represent independently, on each occasion when used herein, hydrogen, phenyl (optionally substituted by one or more halo or $C_{1-3}$ alkyl substituents) and/or $C_{1-4}$ alkyl optionally substituted with one or more substituents selected from halo, —$OR^h$ and —$N(R^h)_2$;

$R^h$ represents, on each occasion when used herein, hydrogen or $C_{1-3}$ alkyl optionally substituted by one or more halo atoms, or a pharmaceutically acceptable ester, amide, solvate or salt thereof, provided that when B represents —S—:
- (a) X represents a direct bond, $R^2$ represents unsubstituted phenyl, $R^3$ represents hydrogen, M represents —$(CH_2)_2$— and $R^1$ represents bromo, then Z does not represent —S—;
- (b) Z, M and X represent direct bonds, $R^1$ and $R^3$ represent —$CH_3$, then $R^2$ does not represent methyl substituted by —OH;
- (c) Z and M both represent a direct bond, then:
  - (I) $R^2$ does not represent unsubstituted 1,2,4-triazol-3-yl when X represents —S— or —$SO_2$—:
    - (A) $R^1$ represents —$CH_2CH_3$ and $R^3$ represents —$CH_2CH_3$ or —$CH_3$; or
    - (B) $R^1$ represents —$CH_3$ and $R^3$ represents —$CH_2CH_3$, —$CH_3$ or Cl; or
  - (II) $R^2$ does not represent 1,2,4-triazol-3-yl substituted in the 1-position by —$C(O)N(CH_2CH_3)_2$ when X represents —$SO_2$—:
    - (A) $R^1$ represents —$CH_2CH_3$, and $R^3$ represents —$CH_2CH_3$ or —$CH_3$,
    - (B) $R^1$ represents —$CH_3$, and $R^3$ represents —$CH_2CH_3$, —$CH_3$ or Cl;
- (d) Z and M represents direct bonds, $R^3$ represents —$CH_3$, then:
  - (I) when $R^1$ represents 4-methoxyphenyl, —X—$R^2$ does not represent —$CH_2$—$C(O)OCH_3$, —$C(=C(H)—OCH_3)$—$C(O)$—$NHCH_3$, —$C(=C(H)—CH_2CH_3)$—$C(O)$—$OCH_3$ or —$C(=C(H)—OCH_3)$—$C(O)$—$OCH_3$;
  - (II) when $R^1$ represents tert-butyl, —X—$R^2$ does not represent —$C(=C(H)—OCH_3)$—$C(O)$—$OCH_3$;
- (e) Z and M represent direct bonds, $R^1$ represents —$CH_3$, $R^3$ represents hydrogen, then $R^2$ does not represent unsubstituted phenyl when X represents a direct bond;
- (f) Z, M and X represent direct bonds, $R^1$ and $R^3$ represent —$CH_3$, then $R^2$ does not represent —$CO_2H$ (or an ethyl ester thereof);
- (g) Z, and M represent direct bonds, $R^1$ and $R^3$ represent tert-butyl, then $R^2$ does not represent hydrogen when X represents —NH—;
- (h) Z, M and X represent direct bonds, $R^3$ represents H, then:
  - (I) when $R^1$ represents 4-chlorophenyl or unsubstituted phenyl, then $R^2$ does not represent unsubstituted phenyl or 4-chlorophenyl;
  - (II) when $R^1$ represents 4-methoxyphenyl, then $R^2$ does not represent 4-chlorophenyl or unsubstituted phenyl;
- (i) Z and M represent direct bonds, $R^1$ represents —$CH_3$, X represents —CH=CH— (i.e. ethenylene) and $R^2$ represents —$CO_2H$, then $R^3$ does not represent tert-butyl or methyl;
- (j) Z, M and X represent direct bonds, $R^3$ represents H, then:
  - (I) $R^2$ does not represent 4-fluoro-1-naphthyl when $R^1$ represents pentyl, butyl or isopropyl;
  - (II) $R^2$ does not represent 3-chloro-4-fluoro-1-naphthyl when $R^1$ represents pentyl, methyl or ethyl;
  - (III) $R^2$ does not represent 3-methyl-4-fluoro-1-naphthyl when $R^1$ represents pentyl, methyl, ethyl or n-propyl
  - (IV) $R^2$ does not represent 2-methyl-4-fluoro-1-naphthyl when $R^1$ represents trifluoromethyl;
- (k) X and M represent direct bonds, $R^2$ represents methyl, $R^3$ represents ethyl, then:
  - (I) when Z represents —NHC(O)—, then $R^1$ does not represent unsubstituted methyl or methyl substituted by —$C(O)CH_3$;
  - (II) when Z represents —NH—, then $R^1$ does not represent hydrogen;
- (l) X, M and Z all represent direct bonds, $R^1$ and $R^3$ represent —$CH_3$, then $R^2$ does not represent —$CH_3$, —$CO_2H$ or unsubstituted phenyl;
- (m) X represents a direct bond, Z represents —S—, M represents —$CH_2$— (i.e. methylene) and $R^1$ represents unsubstituted phenyl, then:
  - (I) when $R^3$ represents —$CH_3$, then $R^2$ does not represent —$CO_2CH_2CH_3$; or
  - (II) when $R^3$ represents hydrogen, then $R^2$ does not represent —$CH_3$;
- (n) X, M and Z represent direct bonds, $R^1$ represents —$CH_2CH_3$ and $R^3$ represents —$CH_3$, then $R^2$ does not represent —$CO_2H$;
- (o) X, Z and M all represent direct bonds, $R^3$ represents hydrogen, then $R^2$ does not represent 1-piperidinyl when $R^1$ represents unsubstituted phenyl, which compounds, esters, amides, solvates and salts are referred to hereinafter as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

By "pharmaceutically acceptable ester, amide, solvate or salt thereof", we include salts of such an ester or amide, and solvates of such an ester, amide or salt. For instance, pharmaceutically acceptable esters and amides such as those defined herein may be mentioned, as well as pharmaceutically acceptable solvates or salts.

Pharmaceutically acceptable esters and amides of the compounds of the invention are also included within the scope of the invention. Pharmaceutically acceptable esters and amides of compounds of formula I may have an appropriate group, for example an acid group (e.g. when $R^1$ and/or $R^2$ represent —$CO_2H$), converted to the appropriate ester or amide. For example, pharmaceutically acceptable esters (of carboxylic acids) that may be mentioned include optionally substituted $C_{1-6}$ alkyl, $C_{5-10}$ aryl and/or $C_{5-10}$ aryl-$C_{1-6}$ alkyl-esters. Pharmaceutically acceptable amides (of carboxylic acids) that may be mentioned include those of the formula —$C(O)N(R^{z1})R^{z2}$, in which $R^{z1}$ and $R^{z2}$ independently represent optionally substituted $C_{1-6}$ alkyl, $C_{5-10}$ aryl, or $C_{5-10}$ aryl-$C_{1-6}$ alkylene-. Preferably, $C_{1-6}$ alkyl groups that may be mentioned in the context of such pharmaceutically acceptable esters and amides are not cyclic, e.g. linear and/or branched.

Preferably, specific esters and amides of compounds of the invention that may be mentioned include esters and amides of compounds of the invention in which $R^1$ and/or $R^2$ represent —$CO_2H$. Hence, $R^1$ and $R^2$ may each independently represent —$CO_2R^x$ (wherein $R^x$ represents $C_{1-4}$ alkyl optionally substituted by one or more halo atoms or —$OR^h$) or —$C(O)N(R^h)_2$, wherein, in each case, $R^h$ is as hereinbefore defined.

Further compounds of the invention that may be mentioned include carbamate, carboxamido or ureido derivatives, e.g. such derivatives of existing amino functional groups.

For the purposes of this invention, therefore, prodrugs of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. I-92, Elesevier, New York-Oxford (1985).

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Unless otherwise stated, the terms $C_{1-q}$ alkyl, and $C_{1-q}$ alkylene, groups (where q is the upper limit of the range) defined herein may be straight-chain or, when there is a sufficient number of carbon atoms, be branched-chain, saturated or unsaturated (so forming, for example, an alkenyl or alkynyl group).

$C_{3-q}$ cycloalkyl groups (where q is the upper limit of the range) that may be mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double or triple bonds (forming for example a cycloalkenyl or cycloalkynyl group). Substituents may be attached at any point on the cycloalkyl group. Further, where there is a sufficient number (i.e. a minimum of four) such cycloalkyl groups may also be part cyclic.

The term "halo", when used herein, includes fluoro, chloro, bromo and iodo.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is between five and ten. Such heterocycloalkyl groups may also be bridged. Further, such heterocycloalkyl groups may be saturated or unsaturated containing one or more double and/or triple bonds, forming for example a $C_{2-q}$ heterocycloalkenyl (where q is the upper limit of the range) or a $C_{7-q}$ heterocycloalkynyl group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form.

For the avoidance of doubt, the term "bicyclic" (e.g. when employed in the context of heterocycloalkyl groups) refers to groups in which the second ring of a two-ring system is formed between two adjacent atoms of the first ring. The term "bridged" (e.g. when employed in the context of cycloalkyl or heterocycloalkyl groups) refers to monocyclic or bicyclic groups in which two non-adjacent atoms are linked by either an alkylene or heteroalkylene chain (as appropriate).

Aryl groups that may be mentioned include $C_{6-10}$ aryl groups. Such groups may be monocyclic, bicyclic or tricyclic and have between 6 and 10 ring carbon atoms, in which at least one ring is aromatic. $C_{6-10}$ aryl groups include phenyl, naphthyl and the like, such as 1,2,3,4-tetrahydronaphthyl. The point of attachment of aryl groups may be via any atom of the ring system. However, when aryl groups are bicyclic or tricyclic, they are linked to the rest of the molecule via an aromatic ring.

Unless otherwise specified, the term "heteroaryl" when used herein refers to an aromatic group containing one or more heteroatom(s) (e.g. one to four heteroatoms) preferably selected from N, O and S. Heteroaryl groups include those which have between 5 and 10 members and may be monocyclic, bicyclic or tricyclic, provided that at least one of the rings is aromatic (so forming, for example, a mono-, bi-, or tricyclic heteroaromatic group). However, when heteroaryl groups are bicyclic or tricyclic, they are linked to the rest of the molecule via an aromatic ring. Heteroaryl groups that may be mentioned include acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form.

It may be specifically stated that the heteroaryl group is monocyclic or bicyclic. In the case where it is specified that the heteroaryl is bicyclic, then it may be consist of a five-, six- or seven-membered monocyclic ring (e.g. a monocyclic heteroaryl ring) fused with another a five-, six- or seven-membered ring (e.g. a monocyclic aryl or heteroaryl ring).

Heteroatoms that may be mentioned include phosphorus, silicon, boron and, preferably, oxygen, nitrogen and sulphur.

For the avoidance of doubt, in cases in which the identity of two or more substituents in a compound of the invention may be the same, the actual identities of the respective substituents are not in any way interdependent. For example, in the situation in which there is more than one $A^1$ substituent present, then those $A^1$ substituents may be the same or different. Further, in the case where there are two $A^1$ substituents present, in which one represents —$OR^e$ and the other represents —$C(O)_2R^e$, then those $R^e$ groups are not to be regarded as being interdependent. Similarly, in specific case when $R^3$ represents —$N(R^f)_2$, then those two $R^f$ groups may be the same or different.

Linker groups, for example as defined by X and Z are specified with hyphens ("-"s) at the respective ends, depicting the points of attachment with the rest of the compound of formula I. For the avoidance of doubt, in relation to the linker groups defined by X and Z, the first hyphen of the linking moiety is the point at which that moiety links to the requisite 5,5-bicycle of formula I (and the last hyphen depicts the linking point to —$R^2$, in the case of the X linker group, or -M-$R^1$, in the case of the Z linker group). For example, when Z represents —$(CH_2)_n$—$N(R^a)$—, it is the —$(CH_2)_n$— portion that is attached to the 5,5-bicycle of formula I.

For the avoidance of doubt, when a term such as "$R^a$ to $R^f$" is employed herein, this will be understood by the skilled person to mean $R^a$, $R^b$, $R^d$, $R^e$ and $R^f$, inclusively. Likewise, a term such as "$B^1$ to $B^8$" when employed herein, will be understood by the skilled person to mean $B^1$, $B^2$, $B^3$, $B^4$, $B^5$, $B^6$, $B^7$ and $B^8$, inclusively.

The skilled person will appreciate that in certain preferred embodiments of the compounds of the invention, some or all of the provisos (a) to (p) above will become redundant. For instance, where it is stated herein in relation to compounds of the invention that preferred such compounds include those in which "when $R^2$ represents aryl, then it is a monocyclic aryl group", then in relation to such a preferred aspect of the invention, at least proviso (j) above will become redundant. $B^1$, $B^2$, $B^3$, $B^4$, $B^5$, $B^6$, $B^7$ and $B^8$ independently represent halo, —$OR^e$, —$C(O)_2R^e$, —$C(O)R^e$, —$C(O)N(R^e)_2$, —CN, —$S(O)_2R^e$, —$S(O)_2N(R^e)_2$, —$N(R^e)_2$ and/or $C_{1-4}$ alkyl optionally substituted by one or more substituents selected from halo, —$OR^e$ and —$C(O)_2R^e$; or, $B^1$, $B^2$, $B^5$ and $B^6$ may alternatively and independently represent =O;

$R^a$, $R^b$, $R^d$, $R^e$ and $R^f$ (e.g. $R^a$, $R^b$, $R^d$ and $R^f$) represent independently, on each occasion when used herein, hydrogen and/or $C_{1-4}$ alkyl optionally substituted with one or more substituents selected from halo and —$OR^h$;

when Z represents —$(CH_2)_n$—$N(R^a)$—CO—, then $R^a$ represents hydrogen.

Compounds of the invention that may be mentioned include those in which:

when X represents —$(CH_2)_m$—$SO_2$—NH—, then m represents 1 or 2;

X does not represent —$(CH_2)_m$—$SO_2$—NH— (i.e. X preferably represents a direct bond, —$(CH_2)_m$—O—, —$(CH_2)_m$—S—, —$(CH_2)_m$—$N(R^d)$—, —S(O)—, —$(CH_2)_m$—$SO_2$—, —$(CH_2)_m$—NH—$SO_2$—, —$(CH_2)_m$—NH—CO—, —$(CH_2)_m$—CO—$N(R^d)$—, —$(CH_2)_m$—NH—CO—NH— or $C_{1-8}$ alkylene optionally substituted by one or more substituents selected from $A^2$).

Compounds of the invention that may be mentioned include those in which:

for example when either Z and M represent direct bonds, then $R^1$ does not represent halo;

for example when X represents a direct bond, then $R^2$ does not represent halo;

when Z and M both represent direct bonds, then $R^1$ does not represent hydrogen;

for example when Z, M and X all represent direct bonds, then:
  (i) $R^1$ does not represent hydrogen or (e.g. when Z and M represent direct bonds) halo; and/or
  (ii) $R^2$ does not represent hydrogen or (e.g. when X represents a direct bond) halo.

Further compounds of the invention that may be mentioned include those in which:

for example when Z, M and X all represent direct bonds, then:
  (i) $R^1$ represents —CN, —$CO_2H$ or, more preferably, $C_{1-8}$ alkyl (optionally substituted by one or more substituents selected from $A^1$), $C_{3-6}$ cycloalkyl, heterocycloalkyl (which latter two groups are optionally substituted by one or more substituents selected from $B^1$ and $B^2$, respectively) aryl or heteroaryl (which latter two groups are optionally substituted with one or more substituents selected from $B^3$ and $B^4$, respectively);

(ii) $R^2$ represents —$CO_2H$ or, more preferably, $C_{1-8}$ alkyl (optionally substituted by one or more substituents selected from $A^3$) or -T-Q;

T represents —$CH_2$—, —$(CH_2)_2$— or, preferably, a direct bond (hence $R^2$ preferably represents halo or, preferably, —$CO_2H$ or, more preferably, $C_{1-8}$ alkyl (optionally substituted by one or more substituents selected from $A^3$) or $C_{3-6}$ cycloalkyl, heterocycloalkyl (which latter two groups are optionally substituted by one or more substituents selected from $B^5$ and $B^6$, respectively), aryl or heteroaryl (which latter two groups are optionally substituted by one or more substituents selected from $B^7$ and $B^8$, respectively)).

Further compounds of the invention that may be mentioned include those in which:

$R^1$ represents halogen, or, preferably, hydrogen, —$CO_2H$, $C_{1-8}$ alkyl (optionally substituted by one or more substituents selected from $A^1$), $C_{3-6}$ cycloalkyl, heterocycloalkyl (which latter two groups are optionally substituted by one or more substituents selected from $B^1$ and $B^2$, respectively), aryl or heteroaryl (which latter two groups are optionally substituted with one or more substituents selected from $B^3$ and $B^4$, respectively);

when Z represents —$(CH_2)_n$—O—, then n represents 0;
when Z represents —$(CH_2)_n$—S—, then n represents 0;
$R^3$ represents hydrogen, halo, —$R^f$ or —$OR^f$;
Z represents —$(CH_2)_n$—O—, —$(CH_2)_n$—S—, —$(CH_2)_n$—N($R^a$)—, —$(CH_2)_{n1}$—S(O)—, —$(CH_2)_n$—$SO_2$—, —$(CH_2)_n$—NH—$SO_2$—, —$(CH_2)_{n1}$—$SO_2$—NH—, —$(CH_2)_n$—NH—CO—, —$(CH_2)_n$—NH—CO—NH— or —$(CH_2)_n$—CO—N($R^a$)—;

M represents $C_{1-8}$ alkylene optionally substituted by one or more substituents independently selected from halo, —$OR^b$, —$SR^b$ or $N(R^b)_2$;

when X represents —$(CH_2)_m$—O—, then m represents 0;
when X represents —$(CH_2)_m$—S—, then m represents 0;
X is selected from —$(CH_2)_m$—O—, —$(CH_2)_m$—S—, —$(CH_2)_m$—N($R^d$)—, —S(O)—, —$(CH_2)_m$—$SO_2$—, —$(CH_2)_m$—NH—$SO_2$—, —$(CH_2)_m$—$SO_2$—NH—, —$(CH_2)_m$—NH—CO—, —$(CH_2)_m$—CO—N($R^d$)—, —$(CH_2)_m$—NH—CO—NH— or $C_{1-8}$ alkylene optionally substituted by one or more substituents selected from $A^2$;
m and n independently represent 2, preferably, 1 or, more preferably, 0.

Further compounds of the invention that may be mentioned include those in which:

Z represents —S— or, preferably, —$(CH_2)_n$—$SO_2$—, or, more preferably, a direct bond, —O—, —$(CH_2)_n$—N($R^a$)—, —$(CH_2)_n$—NH—$SO_2$—, —$(CH_2)_n$—NH—CO—, —$(CH_2)_n$—NH—CO—NH— or —$(CH_2)_n$—CO—N($R^a$)— when $R^2$ represents aryl, then it is a monocyclic aryl group.

For instance in one embodiment, preferred compounds of the invention include those in which:
$R^1$ represents optionally substituted aryl, or optionally substituted monocyclic or bicyclic heteroaryl;
X represents a single bond or $C_{1-3}$ alkylene (optionally substituted as defined herein); and/or
$R^2$ represents optionally substituted aryl or heteroaryl.

For instance in another embodiment, preferred compounds of the invention include those in which:

$R^1$ preferably represents aryl, monocyclic heteroaryl or bicyclic heteroaryl;
X represents a single bond; and/or
$R^2$ represents halo or, preferably, —$CO_2H$ or, more preferably, $C_{1-8}$ alkyl, $C_{3-6}$ cycloalkyl or heterocycloalkyl, which latter three groups are optionally substituted as defined herein).

For instance in another embodiment, preferred compounds of the invention include those in which:
M represents a direct bond or $C_{1-8}$ alkylene optionally substituted by one or more substituents independently selected from halo, —$OR^b$, $C_{1-4}$ alkylthio or —$N(R^b)_2$;
$R^1$ represents $C_{3-8}$ cycloalkyl; and/or
X represents a single bond.

Preferred aryl and heteroaryl groups that $R^1$ and $R^2$ may independently represent include optionally substituted phenyl, naphthyl, pyrrolyl, furanyl, thienyl, imidazolyl, oxazolyl, isoxazolyl, thiazolyl, pyrazolyl, pyridyl, indazolyl, indolyl, indolinyl, isoindolinyl, quinolinyl, isoquinolinyl, quinolizinyl, benzoxazolyl, benzofuranyl, isobenzofuranyl, chromanyl, benzothienyl, pyridazinyl, pyrimidinyl, pyrazinyl, indazolyl, benzimidazolyl, quinazolinyl, quinoxalinyl, 1,3-benzodioxolyl, tetrazolyl, benzothiazolyl, and/or benzodioxanyl.

Preferred $C_{1-8}$ alkyl groups that $R^1$ and $R^2$ may independently represent include optionally substituted $C_{1-6}$ alkyl, which alkyl group may be unsaturated, linear (for example, methyl, ethyl, n-propyl) or branched (e.g. branched $C_{1-5}$ alkyl, such as 1-methyl-isobutyl, 1-methyl-n-propyl or 2,2-dimethylpropyl).

Preferred heterocycloalkyl groups that $R^1$ and $R^2$ may independently represent include optionally substituted 5- or 6-membered heterocycloalkyl groups containing one to three heteroatoms selected from sulfur, or preferably, nitrogen and/or oxygen, so forming for example a piperidinyl, morpholinyl, imidazolidinyl or tetrahydropyranyl group.

Preferred substituents on aryl, heteroaryl, $C_{1-8}$ alkyl, $C_{3-6}$ cycloalkyl or heterocycloalkyl groups that $R^1$ and $R^2$ may represent include (as appropriate):
=O (e.g. in the case of cycloalkyl or, preferably, heterocycloalkyl groups);
—CN;
halo (e.g. fluoro, chloro or bromo);
$C_{1-4}$ alkyl, which alkyl group may be cyclic, part-cyclic, unsaturated or, preferably, linear or branched (e.g. $C_{1-4}$ alkyl (such as ethyl, n-propyl, isopropyl, t-butyl or, preferably, n-butyl or methyl), all of which are optionally substituted with one or more substituents selected from —$OR^{z1}$, —$N(R^{z4})R^{z5}$ (so forming for example a —$CH_2$—$CH_2$—OH or —$CH_2$—$CH_2$—$N(CH_3)_2$ group) and, preferably, halo (e.g. fluoro; so forming, for example, fluoromethyl, difluoromethyl or, preferably, trifluoromethyl); aryl (e.g. phenyl), if appropriate (e.g. when a substitutent on an alkyl group, thereby forming e.g. a benzyl group);
—$OR^{z1}$;
—$C(O)R^{z2}$;
—$C(O)OR^{z3}$;
—$N(R^{z4})R^{z6}$;
—$S(O)_2R^{z6}$;
—$S(O)_2N(R^{z7})R^{z8}$;
—$N(R^{z9})R^{z10}$;
wherein $R^{z1}$ to $R^{z10}$ independently represent, on each occasion when used herein, H or $C_{1-4}$ alkyl (e.g. ethyl, n-propyl, t-butyl or, preferably, n-butyl, methyl or isopropyl) optionally substituted by one or more halo (e.g. fluoro) groups (so forming e.g. a trifluoromethyl group).

Preferred compounds of the invention include those in which:

at least one of X and Z is other than a direct bond;

B represents —S—;

Z represents a direct bond, —O—, —S—, —(CH$_2$)$_n$—N(R$^a$)— or —(CH$_2$)$_n$—N(H)—C(O)—;

R$^a$ represents H;

n represents 0;

M represents a direct bond or C$_{1-3}$ alkylene (e.g. —CH$_2$— or —(CH$_2$)$_2$—), which group may be unsaturated (so forming, for example a ethenylene (i.e. —CH=CH—) group or, preferably an ethynylene group);

R$^1$ represents —CO$_2$H or an amide thereof (i.e. —C(O)N(R$^h$)$_2$), C$_{1-6}$ alkyl optionally substituted by A$^1$, C$_{3-6}$ cycloalkyl (e.g. cyclopropyl or cyclohexyl) optionally substituted by B$^1$ (but preferably unsubstituted), heterocycloalkyl optionally substituted by B$^2$, aryl (e.g. phenyl) optionally substituted by B$^3$, or heteroaryl optionally substituted by B$^4$, when R$^1$ represents C$_{1-6}$ alkyl, then it preferably represents methyl, ethyl, n-propyl or optionally branched C$_{1-5}$ alkyl such as 1-methyl-isobutyl, 1-methyl-n-propyl or 2,2-dimethylpropyl), which C$_{1-6}$ alkyl groups may be substituted by A$^1$ (e.g. by —OR$^e$, so forming, for example a hydroxyalkyl group, such as hydroxypropyl, 1-hydroxymethylisobutyl or 1-hydroxymethyl-n-propyl);

when R$^1$ represents heterocycloalkyl, then such a group preferably represents a 5- or 6-membered heterocycloalkyl group containing one or two heteroatoms selected from nitrogen and/or oxygen, so forming for example a piperidinyl (e.g. 1-piperidinyl), morpholinyl (e.g. 4-morpholinyl), imidazolidinyl (e.g. 1-imidazolidinyl) or tetrahydropyranyl (e.g. 4-tetrahydropyranyl) group;

when R$^1$ represents heteroaryl, then it preferably represent a 5- or 6-membered monocyclic heteroaryl group such as pyrazolyl (e.g. 4-pyrazolyl), pyrazinyl (e.g. 2-pyrazinyl), furanyl (e.g. 2-furanyl), pyrrolyl (e.g. 2-pyrrolyl), imidazolyl (e.g. 1-imidazolyl), thienyl (e.g. 2-thienyl) or pyridyl (e.g. 3-pyridyl);

X represents a direct bond, —O—, —(CH$_2$)$_m$—N(R$^d$)—, —(CH$_2$)$_m$—N(H)—CO, —(CH$_2$)$_m$—CO—N(R$^d$)—, —(CH$_2$)$_m$—NH—SO$_2$— or C$_{1-3}$ alkylene (e.g. —CH$_2$— or —(CH$_2$)$_2$—), which group may be unsaturated (so forming, for example a ethenylene (i.e. —CH=CH—) group or, preferably an ethynylene group);

m represents 0;

R$^d$ represents H;

R$^2$ represents halo (e.g. iodo), C$_{1-6}$ (e.g. C$_{1-4}$) alkyl (e.g. methyl or ethyl) optionally substituted by A$^3$, C$_{3-6}$ cycloalkyl (e.g. cyclohexyl), heterocycloalkyl (e.g. tetrahydropyranyl, such as 4-tetrahydropyranyl or morpholinyl, such as 4-morpholinyl) optionally substituted by B$^6$, aryl (e.g. naphthyl or, preferably, phenyl) optionally substituted by B$^7$, or, heteroaryl (e.g. pyrazolyl, such as 4-pyrazolyl, indolyl, such as 2- or 5-indolyl, pyridyl, such as 3-pyridyl) optionally substituted by B$^8$;

A$^1$ to A$^4$ independently represent halo, —OR$^e$, —CO$_2$R$^e$, —N(R$^e$)—C(O)—R$^e$ or phenyl optionally substituted by —OR$^e$;

B$^1$ to B$^8$ independently represent —N(R$^e$)—C(O)R$^e$, preferably, —C(O)N(R$^e$)$_2$, or, more preferably, halo (e.g. fluoro or chloro), —OR$^e$, —C(O)$_2$R$^e$, —C(O)R$^e$, —CN, —S(O)$_2$R$^e$, —S(O)$_2$N(R$^e$)$_2$, —N(R$^e$)$_2$ and/or C$_{1-3}$ alkyl (e.g. methyl or optionally unsaturated ethyl, e.g. ethenyl), which alkyl group is optionally substituted by one or more substituents selected from halo (e.g. fluoro, so forming, for example, a trifluoromethyl group), —OR$^e$ (so forming for example a hydroxymethyl group) or —C(O)$_2$R$^e$ (so forming, for example, a —CH=CH—COOH group); or B$^1$, B$^2$, B$^5$ and B$^6$ may alternatively and independently represent =O;

R$^a$, R$^b$, R$^d$, R$^e$ and R$^f$ independently represent hydrogen or C$_{1-3}$ alkyl (e.g. methyl) optionally substituted by one or more substituents selected from —N(R$^h$)$_2$, —OR$^h$ and, preferably, halo (e.g. fluoro);

R$^h$ represents H or C$_{1-2}$ alkyl (e.g. ethyl or, preferably, methyl);

R$^3$ represents hydrogen, C$_{1-2}$ alkyl (e.g. methyl) or halo (e.g. fluoro).

Further preferred compounds of the invention include those in which:

when:

(I) Z represents —N(R$^a$)— or —NH—CO— (which compounds of the invention are particularly preferred), then preferably:

M represents a direct bond or C$_{1-3}$ alkylene as defined herein;

R$^1$ is hereinbefore defined;

X is direct bond, —O—, —CO—N(H)—, —NHSO$_2$—

(II) Z represents —S—, then preferably:

M represents a direct bond;

R$^1$ represents aryl (e.g. phenyl) optionally substituted as defined herein;

X represents —NH—;

(III) Z represents —O—, then preferably:

M represents a direct bond or C$_{1-3}$ alkylene as defined herein,

R$^1$ represents —CO$_2$H or an amide thereof (i.e. —C(O)N(R$^h$)$_2$), C$_{1-3}$ alkyl or aryl (e.g. phenyl), which latter two groups are optionally substituted as hereinbefore defined;

X represents —NH— or a direct bond;

(IV) Z represents a direct bond, then, preferably:

M represents C$_{1-3}$ alkylene as defined herein (e.g. ethynylene);

R$^1$ represents aryl as defined herein;

R$^2$ represents halo (e.g. iodo), heterocycloalkyl, aryl or heteroaryl, all of which are as defined herein;

X represents —N(H)— or a direct bond.

Preferred R$^2$ groups that may be mentioned include those in which:

when R$^2$ represents aryl, naphthyl (which group is preferably unsubstituted; e.g. unsubstituted 2-naphthyl) or, preferably, unsubstituted phenyl, (3-trifluoromethyl)phenyl, 3-cyanophenyl, 3-fluorophenyl, 3,5-difluorophenyl, 4-cyanophenyl, 4-trifluoromethylphenyl, 3-acetylphenyl, 3-aminophenyl, 4-aminophenyl, (3-chloro-4-fluoro)phenyl, 3-methanesulfonylphenyl, (4-trifluoromethoxy)phenyl, 4-hydroxyphenyl, (4-acrylic acid)phenyl, 4-carboxyphenyl, 4-methoxyphenyl, 3,4-dimethoxyphenyl and 3-chloro-4-fluorophenyl;

when R$^2$ represents heteroaryl, thienyl (e.g. 2- or 3-thienyl) or, preferably, pyrazolyl (such as 1-methyl-4-pyrazolyl), indolyl (such as 5-indolyl or 2-indolyl), 5-methoxy-3-pyridyl and 6-methoxy-3-pyridyl;

when R$^2$ represents C$_{1-8}$ alkyl, C$_{3-6}$ cycloalkyl or heterocycloalkyl (e.g. a monocyclic 5- or 6-membered heterocycloalkyl group, containing one or two heteroatoms selected from nitrogen and/or oxygen), ethyl, cyclohexyl, carboxymethyl and 4-morpholinyl.

More preferred compounds of the invention include those in which:

B$^1$ to B$^7$ substituents independently represent —N(H)—C(O)CH$_3$, —N(CH$_3$)$_2$, —C(O)N(H)—CH$_2$CH$_2$—N(CH$_3$)$_2$, C(O)N(CH$_3$)$_2$, —C(O)N(H)—CH$_2$CH$_2$—OH or, preferably, trifluoromethyl, —CN, halo (e.g. fluoro or chloro), —COOH, —C(O)CH$_3$, —NH$_2$, —OH, —S(O)$_2$NH$_2$, —S(O)$_2$CH$_3$, —OCF$_3$, —CH$_3$, —OCH$_3$, —CF$_3$, —CH=CH—COOH, and, if applicable, =O;

A$^1$ represents halo or, more preferably, —OR$^e$;

A$^3$ represents —CO$_2$R$^e$, —N(R$^e$)—C(O)—R$^e$ (e.g. —N(H)—C(O)—CH$_3$) or phenyl optionally substituted by —OR$^e$;

B$^1$ represents —OH;

B$^2$ represents methyl or =O;

B$^3$ represents —SO$_2$NH$_2$, fluoro, —OCH$_3$, chloro, —C(O)CH$_3$;

B$^4$ represents methyl;

B$^7$ represents —N(H)—C(O)CH$_3$, —OCH$_3$, —N(CH$_3$)$_2$, —C(O)N(H)—CH$_2$CH$_2$—N(CH$_3$)$_2$, C(O)N(CH$_3$)$_2$, —C(O)N(H)—CH$_2$CH$_2$—OH or, preferably, F, Cl, —CF$_3$, —CN, —OCF$_3$, —C(O)CH$_3$, —NH$_2$, —C(O)$_2$H, —S(O)$_2$CH$_3$, —OH, —CH=CH—COOH;

B$^8$ represents —CH$_3$, —OCH$_3$;

R$^a$ represents hydrogen.

Particularly preferred compounds of the invention include those in which:

Z represents —(CH$_2$)$_n$—O— or, preferably, a direct bond or —(CH$_2$)$_n$—N(R$^a$)—;

M represents a direct bond or C$_{1-2}$ alkylene, which is preferably unsubstituted (e.g. —(CH$_2$)$_2$— or, preferably, —CH$_2$—);

R$^1$ represents C$_{1-6}$ (e.g. C$_{1-4}$) alkyl (optionally substituted by one or more substituents selected from A$^1$) or, R$^1$ preferably represents C$_{3-6}$ (e.g. C$_{3-5}$) cycloalkyl (e.g. cyclopropyl) or aryl (e.g. phenyl), optionally substituted by one or more substituents selected from B$^3$;

X represents —(CH$_2$)$_m$—N(R$^d$)—, —(CH$_2$)$_m$—C(O)—N(R$^d$)—, C$_{1-2}$ alkylene, which is preferably unsubstituted (e.g. —CH$_2$—), or, X more preferably represents a direct bond;

m represents 0 (e.g. when X represents —(CH$_2$)$_m$—C(O)—N(R$^d$)—) or 1 (e.g. when X represents —(CH$_2$)$_m$—N(R$^d$)—);

R$^d$ represents hydrogen or, preferably, C$_{1-2}$ alkyl (e.g. methyl) (e.g. when X represents —(CH$_2$)$_m$—N(R$^d$)— or —(CH$_2$)$_m$—C(O)—N(R$^d$)—);

R$^2$ represents hydrogen, preferably, halo (e.g. iodo) or, more preferably, -T-Q;

T represents unsubstituted C$_{1-2}$ alkylene (e.g. —CH$_2$—CH$_2$— or —CH$_2$—) or, preferably, a direct bond;

T preferably represents a direct bond when X represents a direct bond;

Q represents heterocycloalkyl (e.g. morpholinyl, such as 4-morpholinyl) or, Q more preferably represents aryl (e.g. naphthyl or, preferably, phenyl) optionally substituted by one or more substituents selected from B$^7$, or, heteroaryl (e.g. thienyl, such as 2- or 3-thienyl, pyrazolyl, such as 4-pyrazolyl, or, more preferably, indolyl, such as 6-indolyl, or pyridyl, such as 4-pyridyl or, preferably, 3-pyridyl) optionally substituted by one or more substituents selected from B$^8$;

B$^1$ to B$^8$ independently represent —N(R$^e$)—C(O)R$^e$, preferably, —CN, —C(O)N(R$^e$)$_2$, —OR$^e$, —N(R$^e$)$_2$, or, more preferably, halo (e.g. fluoro or chloro), —C(O)R$^e$ or C$_{1-2}$ alkyl (e.g. methyl) optionally substituted by —OR$^e$;

R$^e$ represents hydrogen or C$_{1-3}$ alkyl (e.g. ethyl or, preferably, methyl), optionally substituted (e.g. at the terminal position) with one or more (e.g. one) substituent selected from —N(R$^h$)$_2$ and, preferably —OR$^h$ (but which alkyl group is preferably unsubstituted);

most preferably, R$^e$ represents hydrogen or methyl;

R$^3$ represents halo (e.g. chloro), R$^f$ or, preferably, hydrogen;

R$^f$ represents C$_{1-3}$ (e.g. C$_{1-2}$) alkyl (such as methyl);

R$^h$ represents hydrogen (e.g. when appended to an oxygen atom, i.e. in the case of —OR$^h$) or C$_{1-2}$ alkyl such as methyl (e.g. when appended to a nitrogen atom, i.e. in the case of —N(R$^h$)$_2$).

Further preferred compounds of the invention include those in which:

B$^3$ represents halo (e.g. fluoro or chloro);

B$^7$ represents —N(R$^e$)—C(O)R$^e$ (e.g. —N(H)—C(O)CH$_3$) or, preferably, halo (e.g. chloro or fluoro), —CN, —C(O)R$^e$ (e.g. —C(O)CH$_3$), —OR$^e$ (e.g. —OH, —OCH$_3$ or —OCF$_3$), —N(R$^e$)$_2$ (e.g. —N(CH$_3$)$_2$) or —C(O)N(R$^e$)$_2$ (e.g. —C(O)N(H)—CH$_2$CH$_2$—N(CH$_3$)$_2$ or, preferably, C(O)N(CH$_3$)$_2$ or —C(O)N(H)—CH$_2$CH$_2$—OH);

B$^8$ represents —OR$^e$ (e.g. —OH, —OCF$_3$ or, preferably, —OCH$_3$).

Preferred Z groups include a direct bond, —N(H)—, —N(CH$_3$)— and —O—.

Preferred "-M-R$^1$" groups include:

phenyl (e.g. unsubstituted phenyl, 4-fluorophenyl or 4-methoxyphenyl);

C$_{1-6}$ part cyclic alkyl (e.g. cyclopropylmethyl);

optionally substituted C$_{1-6}$ (e.g. C$_{1-2}$) alkyl such as ethyl (e.g. methoxyethyl or phenoxyethyl), isobutyl, methyl (for example, -M-R$^1$ represents methyl when Z represents —N(CH$_3$)—) or methyl substituted by phenyl (e.g. benzyl, such as 3,4-dichlorobenzyl, 4-fluorobenzyl, 2-methylbenzyl4-methoxybenzyl, 4-dimethylaminobenzyl) or heteroaryl (e.g. thienyl, furanyl or pyridyl);

C$_{5-6}$ cycloalkyl (e.g. cyclohexyl);

5- or 6-membered heterocycloalkyl (e.g. containing one or two heteroatoms, e.g. tetrahydropyranyl (e.g. 4-tetrahydropyranyl));

5- or 6-membered heteroaryl, e.g. pyridyl, furanyl or thienyl;

hydrogen (e.g. when Z represents —N(H)—).

Preferred "—X—R$^2$" groups include:

pyridyl (e.g. 3-pyridyl, 6-methoxypyrid-3-yl, 5-methoxy-3-pyridyl, 4-pyridyl);

indolyl (e.g. 6-indolyl);

phenyl (e.g. unsubstituted phenyl, 3-acetylphenyl (i.e. 3-(C(O)CH$_3$)-phenyl), 4-(hydroxymethyl)phenyl, 3-fluorophenyl, 4-fluorophenyl, 4-hydroxyphenyl, 4-methoxyphenyl, 3,4-dimethoxyphenyl, 3-(dimethylamino)phenyl, 4-acetamidophenyl, 3-acetamidophenyl, 2-chlorophenyl, 3-chlorophenyl, 4-chlorophenyl, 3-trifluoromethoxyphenyl, 3-chloro-4-fluorophenyl, 3-trifluoromethylphenyl, 3-methoxy-4-hydroxyphenyl, 4-cyanophenyl, 3,5-dimethyl-4-hydroxyphenyl, 3-(dimethylamido)phenyl, 3-[—C(O)N(H)—CH$_2$—CH$_2$—N(CH$_3$)$_2$]-phenyl and 4-[—C(O)N(H)—CH$_2$—CH$_2$—CH$_2$—OH]-phenyl); naphthyl (e.g. 2-naphthyl);

thienyl (e.g. 2-thienyl and 3-thienyl);

pyrazolyl (e.g. 1-methyl-4-pyrazolyl);

morpholinylmethyl (e.g. 4-morpholinylmethyl);

—CH$_2$—N(CH$_3$)—CH$_2$—CH$_2$-phenyl;

—C(O)—N(CH$_3$)—CH$_2$-phenyl; and

—CH$_2$—N(H)-phenyl (e.g. —CH$_2$—N(H)-(3-acetylphenyl), —CH$_2$—N(H)-(3,4-dimethoxyphenyl) and —CH$_2$—N(H)-(3-chloro-4-fluorophenyl)).

Particularly preferred compounds of the invention include those of the examples described hereinafter.

Compounds of the invention may be made in accordance with techniques that are well known to those skilled in the art, for example as described hereinafter.

According to a further aspect of the invention there is provided a process for the preparation of a compound of formula I which process comprises:

(i) for compounds of formula I in which X represents a direct bond, and R² represents optionally substituted C₁₋₈ alkyl, C₃₋₆ cycloalkyl, aryl, heteroaryl or heterocycloalkyl, or for compounds of formula I in which X represents a C₁₋₈ alkylene linker group and R² is as hereinbefore defined, reaction of a corresponding compound of formula II,

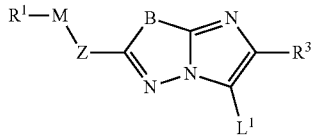
II wherein L¹ represents a suitable leaving group, such as iodo, bromo, chloro or a sulfonate group (e.g. —OS(O)₂CF₃, —OS(O)₂CH₃ or —OS(O)₂PhMe), and Z, M, R¹, B and R³ are as hereinbefore defined, with a compound of formula III,

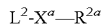
III or a compound of formula IV,

IV respectively, wherein L² represents a suitable group such as —B(OH)₂, —B(OR^{wx})₂ or —Sn(R^{wx})₃, in which each independently represents a C₁₋₆ alkyl group, or, in the case of —B(OR^{wx})₂, the respective R^{wx} groups may be linked together to form a 4- to 6-membered cyclic group (such as a 4,4,5,5-tetramethyl-1,3,2-dioxaborolan-2-yl group), X^a represents a direct bond, R^{2a} represents C₁₋₈ alkyl, C₃₋₆ cycloalkyl, aryl, heteroaryl or heterocycloalkyl, all of which are optionally substituted as hereinbefore defined, X^b represents C₁₋₈ alkylene optionally substituted as hereinbefore defined in the definition of X, and R² is as hereinbefore defined. This reaction may be performed, for example in the presence of a suitable catalyst system, e.g. a metal (or a salt or complex thereof) such as CuI, Pd/C, PdCl₂, Pd(OAc)₂, Pd(Ph₃P)₂Cl₂, Pd(Ph₃P)₄ (i.e. palladium tetrakistriphenylphosphine), Pd₂(dba)₃ or NiCl₂ and a ligand such as t-Bu₃P, (C₆H₁₁)₃P, Ph₃P, AsPh₃, P(o-Tol)₃, 1,2-bis(diphenylphosphino)ethane, 2,2'-bis(di-tert-butylphosphino)-1,1'-biphenyl, 2,2'-bis(diphenylphosphino)-1,1'-bi-naphthyl, 1,1'-bis(diphenyl-phosphino-ferrocene), 1,3-bis(diphenylphosphino)propane, xantphos, or a mixture thereof, together with a suitable base such as, Na₂CO₃, K₃PO₄, Cs₂CO₃, NaOH, KOH, K₂CO₃, CsF, Et₃N, (i-Pr)₂NEt, t-BuONa or t-BuOK (or mixtures thereof) in a suitable solvent such as dioxane, toluene, ethanol, dimethylformamide, ethylene glycol dimethyl ether, water, dimethylsulfoxide, acetonitrile, dimethylacetamide, N-methylpyrrolidinone, tetrahydrofuran or mixtures thereof. The reaction may also be carried out for example at room temperature or above (e.g. at a high temperature such as the reflux temperature of the solvent system). The reaction may also be carried out under microwave irradiation reaction conditions, for example at elevated temperature (e.g. at above 100° C., such as at about 135 to 140° C.). Alternative L² groups that may be mentioned include alkali metal groups (e.g. lithium) and halo groups, which may be converted to a magnesium halide (i.e. a Grignard reagent), in which the magnesium may undergo a 'transmetallation' reaction, thereby being exchanged with, for example, zinc. The skilled person will appreciate that various compounds of formula I in which the groups as defined by —Z-M-R¹ represent similar moieties may also be prepared in a similar manner;

(ii) for compounds of formula I in which X represents —O—, —S— or —N(R^d)—, reaction of a compound of formula II as hereinbefore defined, with a compound of formula V, HX^c—R²   V wherein X^c represents —O—, —S— or —N(R^d)—, and R² is as hereinbefore defined, for example optionally in the presence of an appropriate metal catalyst (or a salt or complex thereof) such as Cu, Cu(OAc)₂, CuI (or CuI/diamine complex), copper tris(triphenyl-phosphine)bromide, Pd(OAc)₂, Pd₂(dba)₃ or NiCl₂ and an optional additive such as Ph₃P, 2,2'-bis(diphenylphosphino)-1,1'-binaphthyl, xantphos, NaI or an appropriate crown ether such as 18-crown-6-benzene, in the presence of an appropriate base such as NaH, Et₃N, pyridine, N,N'-dimethylethylenediamine, Na₂CO₃, K₂CO₃, K₃PO₄, Cs₂CO₃, t-BuONa or t-BuOK (or a mixture thereof, optionally in the presence of 4 Å molecular sieves), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof). This reaction may be carried out under microwave irradiation reaction conditions, for example a described in process step (i) above. Alternatively, the reaction may be performed as described herein, under such microwave irradiation reaction conditions, but in the absence of other reagents such as catalyst, base and even solvent (i.e. the reaction mixture may contain only compound of formula II and compound of formula IVA);

(iii) for compounds of formula I in which Z represents —(CH₂)ₙ—N(R^a)— or —(CH₂)ₙ—O—, M represents a direct bond, and R¹ represents optionally substituted aryl, heteroaryl or, preferably, C₁₋₈ alkyl, C₃₋₆ cycloalkyl or heterocycloalkyl, reaction of a corresponding compound of formula I in which Z represents —(CH₂)ₙ—N(R^a)— or —(CH₂)ₙ—O—, M represents a direct bond, and R¹ represents H, with a compound of formula VI, R^{1a}-L¹   VI wherein L¹ is as hereinbefore defined, and R^{1a} represents aryl, heteroaryl or, preferably, C₁₋₈ alkyl, C₃₋₆ cycloalkyl or heterocycloalkyl, all of which are optionally substituted as hereinbefore defined in respect of corresponding R¹ substituents, for example at around room temperature or above in the presence of a suitable base (e.g. pyridine, triethylamine, dimethylaminopyridine, diisopropylamine, sodium hydroxide, or mixtures thereof), an appropriate solvent (e.g. pyridine, dichloromethane, chloroform, tetrahydrofuran, dimethylformamide, triethylamine, dimethylsulfoxide, water or mixtures thereof) and, in the case of biphasic reaction conditions, optionally in the presence of a phase transfer catalyst. The skilled person will appreciate that the —(CH₂)ₙ—N(R^a)— group, e.g. when R^a represents hydrogen, may need to be protected (and subsequently deprotected) in order to effect this transformation. Further, the skilled person will also appreciate which values of R¹ in compounds of formula VI (in obtaining compounds of formula I) would be suitable in such a process step;

(iv) for compounds of formula I in which Z represents —O—, —S— or —(CH₂)ₙ—N(R^a)— in which n represents 0, reaction of a compound of formula VII,

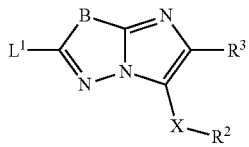

VII wherein $L^1$, B, X, $R^2$ and $R^3$ are as hereinbefore defined, with a compound of formula VIII,

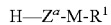   VIII wherein $Z^a$ represents —O—, —S— or —N($R^a$)—, and $R^a$, $R^1$ and M are as hereinbefore defined, under standard conditions, for example, such as those hereinbefore described in respect of process step (i) or (ii) above (preferably process step (ii) above);

(v) for compounds of formula I in which Z represents a direct bond and M represents $C_{1-8}$ alkylene optionally substituted as hereinbefore defined, reaction of a compound of formula VII as hereinbefore defined, with a compound of formula IX,

   IX wherein Ma represents $C_{1-8}$ alkylene optionally substituted by one or more substituents selected from halo, —$OR^b$, —$SR^b$ and —$N(R^b)_2$, and $R^1$ and $L^1$ are as hereinbefore defined, for example under reaction conditions such as those hereinbefore described in respect of process step (i);

(vi) compounds of formula I in which B, Z or X represents —S(O)— or —$S(O)_2$— may be prepared by oxidation of a corresponding compound of formula I in which B, Z or X represents —S—, under standard conditions, for example in the presence of a suitable oxidising agent, such as $KMnO_4$ or meta-chloroperbenzoic acid (mCPBA), optionally in the presence of a suitable solvent;

(vii) compounds of formula I in which Z represents —NHS$(O)_2$, —NHC(O)— or —NHC(O)NH— may be prepared by reaction of a corresponding compound of formula I in which Z represents —N($R^a$)—, $R^a$ represents H, M represent a direct bond and $R^1$ represents hydrogen, with a compound of formula X,

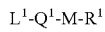   X wherein $L^1$ is as hereinbefore defined and preferably represents chloro, $Q^1$ represents —$S(O)_2$—, —C(O)— or —C(O)NH—, and M and $R^1$ are as hereinbefore defined, under standard reaction conditions, for example such as those hereinbefore described in respect of process step (iii) above. The skilled person will appreciate that similar groups defined by X in the compound of formula I may also be prepared in a similar manner;

(viii) compounds of formula I in which X represents —NH— and $R^2$ represents optionally substituted $C_{1-8}$ alkyl, may be prepared by the reductive amination of a corresponding compound of formula I in which X represents —NH— and $R^2$ represents hydrogen, with a compound of formula XI,

   XI wherein $R^{2b}$ represents $C_{1-7}$ alkyl optionally substituted by one or more substituents selected from $A^3$, and $A^3$ is as hereinbefore defined, under standard reaction conditions, for example in the presence of sodium cyanoborohydride or sodium triacetoxyborohydride, optionally in the presence of a suitable solvent such as an alcohol (e.g. ethanol or methanol);

(ix) compounds of formula I in which X represents —$CH_2$—NH— may be prepared by a reductive amination of a compound of formula XII,

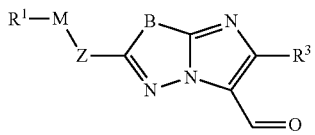

XII wherein Z, M, $R^1$, B and $R^3$ are as hereinbefore defined, with a compound of formula XIII,

   XIII wherein $R^2$ is as hereinbefore defined, for example under conditions such as those described hereinbefore in respect of process step (viii) above;

(x) for compounds of formula I in which X represents —$CH_2$—N($R^d$)— and $R^2$ represents hydrogen or optionally substituted $C_{1-8}$ alkyl, provided that at least one of $R^2$ and $R^d$ is other than hydrogen (so forming a secondary or tertiary amine), or, for compounds of formula I in which —X—$R^2$ represents —$CH_2$-heterocycloalkyl, in which the heterocycloalkyl group is attached to the relevant —$CH_2$— moiety via a nitrogen atom of the heterocycloalkyl group (so forming a tertiary amino moiety; for example —$CH_2$-[4-morpholinyl]), reaction of a compound of formula XIIIA,

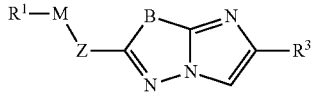

XIIIA wherein Z, M, $R^1$, B and $R^3$ are as hereinbefore defined, with formaldehyde and a compound of formula XIIIB,

   XIIIB wherein $X^d$ represents —N($R^d$)— and $R^{2d}$ represents hydrogen or $C_{1-8}$ alkyl (optionally substituted by one or more substituents selected from $A^3$), provided that at least one of $R^d$ and $R^{2d}$ is other than hydrogen (so forming a secondary or tertiary amine), or with a compound of formula XIIIC,

   XIIIC wherein $het^a$ represents a heterocycloalkyl group containing a —N(H)— moiety that is integral to the cyclic group (e.g. morphine, piperidine, pyrrolidine, etc), i.e. a secondary amino group, both of which may be performed under reaction conditions known to those skilled in the art, for example in the presence of glacial acetic acid and an appropriate solvent (e.g. an alcohol, such as methanol), which is preferably dry, under an inert atmosphere;

(xi) compounds of formula I in which X represents —$CH_2$—O— and $R^2$ represents hydrogen may be prepared by reduction of a corresponding compound of formula XII as hereinbefore defined, in the presence of a suitable reducing agent, for example, a borohydride such as $NaBH_4$, $LiBH_4$ or $LiAlH_4$, in the presence of a suitable solvent, e.g. an alcohol (e.g. methanol or ethanol);

(xii) compounds of formula I in which X represents —$(CH_2)_m$—C(O)N($R^d$)— may be prepared by reaction of a compound corresponding to a compound of formula I but in which —X—$R^2$ represents —$(CH_2)_m$—C(O)OH with a compound of formula XIV,

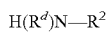   XIV wherein $R^d$ and $R^2$ are as hereinbefore defined, under standard amide coupling reaction conditions, for example in the presence of a suitable coupling reagent (e.g. 1,1'-carbonyldiimidazole, N,N'-dicyclohexylcarbodiimide, 1-(3-dimethylaminopropyl)-3-ethylcarbodiimide (or hydrochloride thereof) or N,N'-disuccinimidyl carbonate), optionally in the presence of a suitable base (e.g. sodium hydride, sodium bicarbonate, potassium carbonate, pyridine, triethylamine, dimethylaminopyridine, diisopropylamine, sodium hydroxide, potassium tert-butoxide and/or lithium diisopropylamide (or variants thereof) and an appropriate solvent (e.g. tetrahydrofuran, pyridine, toluene, dichloromethane, chloroform, acetonitrile, dimethylformamide, trifluoromethylbenzene, dioxane or triethylamine). Alternatively, the carboxylic acid group may be converted under standard conditions to the corresponding acyl chloride (e.g. in the presence of $SOCl_2$ or oxalyl chloride), which acyl chloride is then reacted with a compound of formula XIV, for example under similar conditions to those mentioned above;

(xiii) for compounds of formula I in which there is a —$CH_2$— group present, reduction of a corresponding compound of formula I in which there is a —C(OH)— group present, for example, in the presence of a suitable silicon based reducing agent such as $(CH_3)_2SiCl_2$ and optionally in the presence of an additive such as NaI;

(xiv) for compounds of formula I in which X represents methylene substituted by —OH, and $R^2$ represents optionally substituted $C_{1-8}$ alkyl, $C_{3-6}$ cycloalkyl, aryl, heteroaryl or heterocycloalkyl, reaction of a compound of formula XII as defined above with a compound of formula XV, $$R^{2a}\text{-}M^1 \qquad\qquad XV$$

wherein $M^1$ represents an appropriate alkali metal group (e.g. sodium, potassium or, especially, lithium), a —Mg-halide or a zinc-based group (e.g. a zinc halide group) and $R^{2a}$ is as hereinbefore defined, i.e. $R^{2a}$ represents $C_{1-8}$ alkyl (optionally substituted by one or more $A^3$ substituents), $C_{3-6}$ cycloalkyl, heterocycloalkyl (which latter two groups are optionally substituted by one or more substituents selected from $B^5$ and $B^6$, respectively), aryl or heteroaryl (which latter two groups are optionally substituted by one or more substituents selected from $B^7$ and $B^8$, respectively), under appropriate reaction conditions, for example under an inert atmosphere, in the presence of a suitable anhydrous solvent (e.g. an anhydrous polar aprotic solvent such a tetrahydrofuran, diethyl ether and the like);

(xv) compounds of formula I in which there is a —$NH_2$ group present (e.g. when "—X—$R^2$" or "—Z-M-$R^1$" represent —$NH_2$) may be prepared by the reduction of a corresponding compound of formula I in which there is a —$NO_2$ group present, under standard reaction conditions known to those skilled in the art, for example in the presence of a suitable reducing agent, for example reduction by catalytic hydrogenation (e.g. in the presence of a palladium catalyst in a source of hydrogen) or employing an appropriate reducing agent (such as trialkylsilane, e.g. triethylsilane). The skilled person will appreciate that where the reduction is performed in the presence of a —C(O)— group (e.g. when T represents —C(O)—), a chemoselective reducing agent may need to be employed;

(xvi) compounds of formula I in which —X—$R^2$ represents —C(O)OH, may be prepared by oxidation of a corresponding compound of formula XII as hereinbefore defined, in the presence of a suitable oxidising agent such as a peroxide (e.g. t-butylhydroperoxide);

(xvii) compounds of formula I in which X represents —$(CH_2)_m$—$S(O)_2N(H)$— may be prepared by reaction of a compound corresponding to a compound of formula I but in which —X—$R^2$ represents —$(CH_2)_m$—$S(O)_2OH$ (or an activated derivative thereof; see process step (xii) above), with a compound of formula XIV as hereinbefore defined but in which $R^d$ represents hydrogen, for example under reaction conditions hereinbefore described in respect of process step (xii) above.

Compounds of formula II in which $L^1$ represents halo, may be prepared by reaction of a corresponding compound of formula XIIIA, with a source of halide ions, for instance an electrophile that provides a source of iodide ions includes iodine, diiodoethane, diiodotetrachloroethane or, preferably, N-iodosuccinimide, a source of bromide ions includes N-bromosuccinimide and bromine, and a source of chloride ions includes N-chlorosuccinimide, chlorine and iodine monochloride. Compounds of formula II in which $R^3$ represents halo (and $L^1$ preferably represents halo) may be prepared from a corresponding compound of formula II in which $R^3$ represents hydrogen, using the above-mentioned compounds that provide a source of halide ions, under standard reaction conditions.

Other compounds of formula II may also be prepared under standard conditions, for instance such as those described herein. For example, for synthesis of compounds of formula II in which $L^1$ represents a sulfonate group, reaction of a compound corresponding to a compound of formula II but in which $L^1$ represents —OH with an appropriate sulfonyl halide, under standard reaction conditions, such as in the presence of a base (e.g. as hereinbefore described in respect of preparation of compounds of formula I (process step (iii)).

Compounds corresponding to a compound of formula I but in which —X—$R^2$ represents —$(CH_2)_m$—$S(O)_2OH$, may be prepared by reaction of a corresponding compound of formula XIIIA, in the presence of an appropriate reagent for the introduction of the sulfonic acid group, e.g. oleum (or the like).

Compounds of formula XII may be prepared by reaction of a corresponding compound of formula XIIIA, with dimethylformamide, under standard conditions, and optionally in the presence of $POCl_3$ (so forming for example, a Vilsmeir-Haack reagent), oxalyl chloride, phosgene or the like, in optionally in the presence of a further solvent other than DMF (e.g. dichloromethane).

Compounds of formula XIIIA in which $R^3$ represents hydrogen or $C_{1-4}$ alkyl optionally substituted by one or more halo atoms, reaction of a compound of formula XVI,

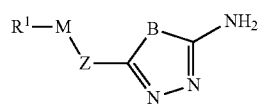

XVI wherein Z, M, $R^1$ and B are as hereinbefore defined, with a compound of formula XVII, $$Cl\text{—}CH_2\text{—}C(O)\text{—}R^{3a} \qquad\qquad XVII$$

wherein $R^{3a}$ represents hydrogen or $C_{1-4}$ alkyl optionally substituted by one or more halo atoms, under standard conditions known to those skilled in the art. For example, the compound of formula XVII may already be present in water, and hence, the reaction may be performed in the presence of water as a solvent, optionally in the presence of a further solvent, such as an alcohol (e.g. n-butanol), for example at room temperature or, preferably, elevated temperature such as at reflux.

Compounds of formula XVI in which Z represents —(CH$_2$)$_n$—N(R$^a$)—, R$^a$ represents hydrogen, n represents 0, M represents a direct bond and R$^1$ represents hydrogen, may be prepared by intramolecular reaction of a compound of formula XVIII,

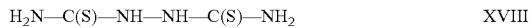

H$_2$N—C(S)—NH—NH—C(S)—NH$_2$                    XVIII for example, under standard conditions, e.g. in the presence of an activating group such as dicyclohexylcarbodiimide (DCC) or, preferably, 1-ethyl-3-(3-dimethylaminopropyl)carbodiimide hydrochloride (EDC.HCl), optionally in the presence of hydrogen peroxide (e.g. 50% H$_2$O$_2$).

Compounds of formula XV may be prepared by reaction of a corresponding compound of formula XIX, R$^{2a}$L$^x$                    XIX wherein L$^x$ represents halo, and R$^{2a}$ is as hereinbefore defined, by, in the case of the formation of a compound of formula XV in which:

(i) M$^1$ represents a —Mg-halide, employing magnesium or a suitable reagent such as a mixture of C$_{1-6}$ alkyl-Mg-halide and ZnCl$_2$ or LiCl, under standard Grignard conditions known to those skilled in the art (e.g. optionally in the presence of a catalyst (e.g. FeCl$_3$));

(ii) M$^1$ represents lithium, forming the corresponding lithiated compound under halogen-lithium exchange reaction conditions known to those skilled in the art (e.g. employing n-BuLi or t-BuLi in the presence of an anhydrous suitable solvent (e.g. a polar aprotic solvent such as THF)).

The skilled person will also appreciate that the magnesium of the Grignard reagent or the lithium of the lithiated species may be exchanged to a different metal (i.e. a transmetallation reaction may be performed), for example to zinc (e.g. using ZnCl$_2$), so forming for example, the corresponding compound of formula XV in which M$^1$ represent a zinc-based group.

Compounds of formula XVI may be prepared by reaction of a corresponding compound of formula XX,

XX wherein L$^1$ and B are as hereinbefore defined, with a compound of formula VIII or IX as hereinbefore defined, for example under reaction conditions such as those hereinbefore described in respect of preparation of compounds of formula I (process steps (iv) and (v)).

Compounds of formula XX in which L$^1$ represents halo, may be prepared by reaction of a corresponding compound of formula XXI,

XXI wherein B is as hereinbefore defined, in the presence of a source of halide ions (e.g. in the case of bromide ions, bromine), such as those described hereinbefore in respect of preparation of compounds of formula II, for instance, in the presence of a suitable solvent, such as an alcohol (e.g. methanol) optionally in the presence of a suitable base, such as a weak inorganic base, e.g. sodium bicarbonate.

Compounds of formulae III, IV, V, VII, IX, X, XI, XIII, XIV, XVI, XVII, XVIII, XIX, XXI (as well as some compounds of formula II, VI, VIII, XII and XX) are either commercially available, are known in the literature, or may be obtained either by analogy with the processes described herein, or by conventional synthetic procedures, in accordance with standard techniques, from available starting materials using appropriate reagents and reaction conditions. Further, the skilled person will appreciate that where reactions to introduce the "—Z-M-R$^1$" moiety of compounds of formula I is described, similar reactions may be performed to introduce the "—X—R$^2$" moiety in compounds of formula I and vice versa. Further, processes to prepare compounds of formula I may be described in the literature, for example in:

Werber, G. et al.; *J. Heterocycl. Chem.*; EN; 14; 1977; 823-827;

Andanappa K. Gadad et al. *Bioorg. Med. Chem.* 2004, 12, 5651-5659;

Paul Heinz et al. *Monatshefte für Chemie*, 1977, 108, 665-680;

M. A. El-Sherbeny et al. *Boll. Chim. Farm.* 1997, 136, 253-256;

Nicolaou, K. C.; Bulger, P. G.; Sarlah, D. *Angew. Chem. Int. Ed.* 2005, 44, 2-49;

Bretonnet et al. *J. Med. Chem.* 2007, 50, 1872;

Asunción Marín et al. *Farmaco* 1992, 47 (1), 63-75;

Severinsen, R. et al. *Tetrahedron* 2005, 61, 5565-5575;

Nicolaou, K. C.; Bulger, P. G.; Sarlah, D. *Angew. Chem. Int. Ed.* 2005, 44, 2-49;

M. Kuwahara et al., *Chem. Pharm Bull.*, 1996, 44, 122;

Wipf, P.; Jung, J.-K. *J. Org. Chem.* 2000, 65(20), 6319-6337;

Shintani, R.; Okamoto, K. *Org. Lett.* 2005, 7 (21), 4757-4759;

Nicolaou, K. C.; Bulger, P. G.; Sarlah, D. *Angew. Chem. Int. Ed.* 2005, 44, 2-49;

J. Kobe et al., *Tetrahedron*, 1968, 24, 239;

P. F. Fabio, A. F. Lanzilotti and S. A. Lang, *Journal of Labelled Compounds and Pharmaceuticals*, 1978, 15, 407;

F. D. Bellamy and K. Ou, *Tetrahedron Lett.*, 1985, 25, 839;

M. Kuwahara et al., *Chem. Pharm Bull.*, 1996, 44, 122;

A. F. Abdel-Magid and C. A Maryanoff. *Synthesis*, 1990, 537;

M. Schlosser et al. *Organometallics in Synthesis. A Manual*, (M. Schlosser, Ed.), Wiley & Sons Ltd: Chichester, UK, 2002, and references cited therein;

L. Wengwei et al., *Tetrahedron Lett.*, 2006, 47, 1941;

M. Plotkin et al. *Tetrahedron Lett.*, 2000, 41, 2269;

Seyden-Penne, J. *Reductions by the Alumino and Borohydrides*, VCH, NY, 1991;

O. C. Dermer, *Chem. Rev.*, 1934, 14, 385;

N. Defacqz, et al., *Tetrahedron Lett.*, 2003, 44, 9111;

S. J. Gregson et al., *J. Med. Chem.*, 2004, 47, 1161;

A. M. Abdel Magib, et al., *J. Org. Chem.*, 1996, 61, 3849;

A. F. Abdel-Magid and C. A Maryanoff. *Synthesis*, 1990, 537;

T. Ikemoto and M. Wakimasu, *Heterocycles*, 2001, 55, 99;

E. Abignente et al., *Il Farmaco*, 1990, 45, 1075;

T. Ikemoto et al., *Tetrahedron*, 2000, 56, 7915;

T. W. Greene and P. G. M. Wuts, *Protective Groups in Organic Synthesis*, Wiley, NY, 1999;

S. Y. Han and Y.-A. Kim. *Tetrahedron*, 2004, 60, 2447;

J. A. H. Lainton et al., *J. Comb. Chem.*, 2003, 5, 400; or

Wiggins, J. M. *Synth. Commun.*, 1988, 18, 741.

The substituents Z, M, R$^1$, X, R$^2$ and B in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications, etherifications, halogenations or nitrations. Such reactions may result in the formation of a symmetric or asymmetric final compound of the invention or intermediate. The precursor groups can be changed to a different such group, or to the groups defined in formula I, at any time during the reaction sequence. For example, in cases in which $R^1$ represents an ester of —$CO_2H$, the skilled person will appreciate that at any stage during the synthesis (e.g. the final step), the relevant ester group may be hydrolysed to form a carboxylic acid functional group.

Compounds of the invention bearing a carboxyester functional group may be converted into a variety of derivatives according to methods well known in the art to convert carboxyester groups into carboxamides, N-substituted carboxamides, N,N-disubstituted carboxamides, carboxylic acids, and the like. The operative conditions are those widely known in the art and may comprise, for instance in the conversion of a carboxyester group into a carboxamide group, the reaction with ammonia or ammonium hydroxide in the presence of a suitable solvent such as a lower alcohol, dimethylformamide or a mixture thereof; preferably the reaction is carried out with ammonium hydroxide in a methanol/dimethylformamide mixture, at a temperature ranging from about 50° C. to about 100° C. Analogous operative conditions apply in the preparation of N-substituted or N,N-disubstituted carboxamides wherein a suitable primary or secondary amine is used in place of ammonia or ammonium hydroxide. Likewise, carboxyester groups may be converted into carboxylic acid derivatives through basic or acidic hydrolysis conditions, widely known in the art. Further, amino derivatives of compounds of the invention may easily be converted into the corresponding carbamate, carboxamido or ureido derivatives.

Compounds of the invention may be isolated from their reaction mixtures using conventional techniques (e.g. recrystallisations).

It will be appreciated by those skilled in the art that, in the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Synthesis*", $3^{rd}$ edition, T. W. Greene & P. G. M. Wutz, Wiley-Interscience (1999).

Medical and Pharmaceutical Uses

Compounds of the invention are indicated as pharmaceuticals. According to a further aspect of the invention there is provided a compound of the invention, as hereinbefore defined but without provisos (a), (c), (d), (e), (g) and (j) to (o), for use as a pharmaceutical.

Compounds of the invention may inhibit protein kinases, such as CDK-2, SRC, GSK-3, and in particular may inhibit PI3-K or a PIM family kinase such as PIM-1, PIM-2 and/or PIM-3, for example as may be shown in the tests described below and/or in tests known to the skilled person. Thus, the compounds of the invention may be useful in the treatment of those disorders in an individual in which the inhibition of such protein kinases (e.g. a PIM family kinase such as PIM-1 and/or PIM-2) is desired and/or required.

The term "inhibit" may refer to any measurable reduction and/or prevention of catalytic protein kinase (e.g. CDK-2, SRC, GSK-3 or, preferably, PI3-K or a PIM family kinase such as PIM-1, PIM-2 and/or PIM-3) activity. The reduction and/or prevention of protein kinase activity may be measured by comparing the protein kinase activity in a sample containing a compound of the invention and an equivalent sample of protein kinase (e.g. CDK-2, SRC, GSK-3 or, preferably, PI3-K or a PIM family kinase such as PIM-1, PIM-2 and/or PIM-3) in the absence of a compound of the invention, as would be apparent to those skilled in the art. The measurable change may be objective (e.g. measurable by some test or marker, for example in an in vitro or in vivo assay or test, such as one described hereinafter, or otherwise another suitable assay or test known to those skilled in the art) or subjective (e.g. the subject gives an indication of or feels an effect).

Compounds of the invention may be found to exhibit 50% inhibition of a protein kinase (e.g. CDK-2, SRC, GSK-3 or, preferably, PI3-K or a PIM family kinase such as PIM-1, PIM-2 and/or PIM-3) at a concentration of 100 µM or below (for example at a concentration of below 50 µM, or even below 10 µM), when tested in an assay (or other test), for example as described hereinafter, or otherwise another suitable assay or test known to the skilled person.

Compounds of the invention are thus expected to be useful in the treatment of a disorder in which a protein kinase (and particularly CDK-2, SRC, GSK-3 or, preferably, PI3-K or a PIM family kinase such as PIM-1, PIM-2 and/or PIM-3) is known to play a role and which are characterised by or associated with an overall elevated activity of that protein kinase (due to, for example, increased amount of the kinase or increased catalytic activity of the kinase). Such disorders include cancer (particularly lymphomas or a cancer as described hereinafter), inflammatory diseases (such as asthma, allergy and Chrohn's disease), immunosuppression (such as transplantation rejection and autoimmune diseases), and other associated diseases. Other associated diseases that may be mentioned (particularly due to the key role of kinases in the regulation of cellular proliferation) include other cell proliferative disorders and/or non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

As stated above, the compounds of the invention may be useful in the treatment of cancer. More, specifically, the compounds of the invention a may therefore be useful in the treatment of a variety of cancer including, but not limited to: carcinoma such as cancer of the bladder, breast, colon, kidney, liver, lung (including small cell lung cancer), esophagus, gall-bladder, ovary, pancreas, stomach, cervix, thyroid, prostate and skin, as well as squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xeroderma pigmentosum, keratoxanthoma, thyroid follicular cancer and Kaposi's sarcoma.

Further, the protein kinases (e.g. CDK-2, SRC, GSK-3 or, more particularly, PI3-K or a PIM family kinase such as PIM-1, PIM-2 and/or PIM-3) may also be implicated in the multiplication of viruses and parasites. They may also play a major role in the pathogenesis and development of neurodegenerative disorders. Hence, compounds of the invention may also be useful in the treatment of viral conditions, parasitic conditions, as well as neurodegenerative disorders.

Compounds of the invention are indicated both in the therapeutic and/or prophylactic treatment of the above-mentioned conditions.

According to a further aspect of the present invention, there is provided a method of treatment of a disease which is associated with the inhibition of protein kinase (e.g. CDK-2, SRC, GSK-3 or, preferably, PI3-K or a PIM family kinase such as PIM-1, PIM-2 and/or PIM-3) is desired and/or required (e.g. cancer or another disease as mentioned herein), which method comprises administration of a therapeutically effective amount of a compound of the invention, as hereinbefore defined but without the provisos, to a patient suffering from, or susceptible to, such a condition.

"Patients" include mammalian (including human) patients.

The term "effective amount" refers to an amount of a compound, which confers a therapeutic effect on the treated patient. The effect may be objective (e.g. measurable by some test or marker) or subjective (e.g. the subject gives an indication of or feels an effect).

Compounds of the invention may be administered orally, intravenously, subcutaneously, buccally, rectally, dermally, nasally, tracheally, bronchially, sublingually, by any other parenteral route or via inhalation, in a pharmaceutically acceptable dosage form.

Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like. The type of pharmaceutical formulation may be selected with due regard to the intended route of administration and standard pharmaceutical practice. Such pharmaceutically acceptable carriers may be chemically inert to the active compounds and may have no detrimental side effects or toxicity under the conditions of use.

Such formulations may be prepared in accordance with standard and/or accepted pharmaceutical practice. Otherwise, the preparation of suitable formulations may be achieved non-inventively by the skilled person using routine techniques and/or in accordance with standard and/or accepted pharmaceutical practice.

According to a further aspect of the invention there is thus provided a pharmaceutical formulation including a compound of the invention, as hereinbefore defined but without provisos (a), (c), (d), (e), (g) and (j) to (o), in admixture with a pharmaceutically acceptable adjuvant, diluent or carrier.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The amount of compound of the invention in the formulation will depend on the severity of the condition, and on the patient, to be treated, as well as the compound(s) which is/are employed, but may be determined non-inventively by the skilled person.

The invention further provides a process for the preparation of a pharmaceutical formulation, as hereinbefore defined, which process comprises bringing into association a compound of the invention, as hereinbefore defined but without provisos (a), (c), (d), (e), (g) and (j) to (o), or a pharmaceutically acceptable ester, amide, solvate or salt thereof with a pharmaceutically-acceptable adjuvant, diluent or carrier.

Compounds of the invention may also be combined with other therapeutic agents that are inhibitors of protein kinases (e.g. CDK-2, SRC, GSK-3 or, preferably, PI3-K or a PIM family kinase such as PIM-1, PIM-2 and/or PIM-3) and/or useful in the treatment of a cancer and/or a proliferative disease. Compounds of the invention may also be combined with other therapies.

According to a further aspect of the invention, there is provided a combination product comprising:

(A) a compound of the invention, as hereinbefore defined but without the provisos (for example without provisos (a), (c), (d), (e), (g) and (j) to (o)); and
(B) another therapeutic agent that is useful in the treatment of cancer and/or a proliferative disease, wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:

(1) a pharmaceutical formulation including a compound of the invention, as hereinbefore defined but without the provisos (for example, without provisos (a), (c), (d), (e), (g) and (j) to (o)), another therapeutic agent that is useful in the treatment of cancer and/or a proliferative disease, and a pharmaceutically-acceptable adjuvant, diluent or carrier; and (2) a kit of parts comprising components:

(a) a pharmaceutical formulation including a compound of the invention, as hereinbefore defined but without the provisos (for example without provisos (a), (c), (d), (e), (g) and (j) to (o)), in admixture with a pharmaceutically-acceptable adjuvant, diluent or carrier; and (b) a pharmaceutical formulation including another therapeutic agent that is useful in the treatment of cancer and/or a proliferative disease in admixture with a pharmaceutically-acceptable adjuvant, diluent or carrier, which components (a) and (b) are each provided in a form that is suitable for administration in conjunction with the other.

The invention further provides a process for the preparation of a combination product as hereinbefore defined, which process comprises bringing into association a compound of the invention, as hereinbefore defined but without the provisos (for example, without provisos (a), (c), (d), (e), (g) and (j) to (o)), or a pharmaceutically acceptable ester, amide, solvate or salt thereof with the other therapeutic agent that is useful in the treatment of cancer and/or a proliferative disease, and at least one pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

Depending on the disorder, and the patient, to be treated, as well as the route of administration, compounds of the invention may be administered at varying therapeutically effective doses to a patient in need thereof. However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of the invention.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

Compounds of the invention may have the advantage that they are effective inhibitors of protein kinases (such as CDK-2, SRC, GSK-3 or, preferably, PI3-K or a PIM family kinase such as PIM-1, PIM-2 and/or PIM-3).

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

EXAMPLES/BIOLOGICAL TESTS

PIM-1 Biochemical Assay

The biochemical assay to measure PIM-1 activity relies on the ADP Hunter assay kit (DiscoveRx Corp., Cat. #90-0077), that determines the amount of ADP as direct product of the kinase enzyme activity.

The enzyme has been expressed and purified in-house as a recombinant human protein with a C-terminal histidine tag. The protein is active and stable.

Assay conditions were as indicated by the kit manufacturers with the following adaptations for the kinase activity step:
Kinase assay buffer and assay volume stay as recommended (15 mM HEPES, pH 7.4, 20 mM NaCl, 1 mM EGTA, 0.02% Tween 20, 10 mM $MgCl_2$ and 0.1 mg/ml bovine γ-globulins/75 μl assay volume)
Incubation time and temperature: 60 min at 30° C.
PIM-1 concentration: 50 pg/μl
ATP concentration: 100 μM
PIM-1 substrate peptide: PIMtide (ARKRRRHPSGPPTA)
Peptide concentration: 60 μM
Positive control for kinase activity inhibition: 1-10 μM Staurosporine
DMSO concentration have to stay below 2% during the kinase reaction Assays were performed in either 96 or 384-well plates. The final outcome of the coupled reactions provided by the kit is the release of the fluorescent product Resorufin and has been measured with a multilabel HTS counter VICTOR V (PerkinElmer) using an excitation filter at 544 nm and an emission filter at 580 nm.

PIM-2 Biochemical Assay

The biochemical assay to measure PIM-2 activity relies on the ADP Hunter assay kit (DiscoveRx Corp., Cat. #90-0077), that determines the amount of ADP as direct product of the kinase enzyme activity.

The enzyme has been expressed and purified in-house as a recombinant human protein with a N-terminal histidine tag. The protein is active and stable.

Assay conditions were as indicated by the kit manufacturers with the following adaptations for the kinase activity step:
Kinase assay buffer and assay volume stay as recommended (15 mM HEPES, pH 7.4, 20 mM NaCl, 1 mM EGTA, 0.02% Tween 20, 10 mM $MgCl_2$ and 0.1 mg/ml bovine γ-globulins/20 μl assay volume)
Incubation time and temperature: 30 min at 30° C.
PIM-2 concentration: 350 pg/μl
ATP concentration: 100 μM
PIM-1 substrate peptide: PIMtide (ARKRRRHPSGPPTA)
Peptide concentration: 100 μM
Positive control for kinase activity inhibition: 1-10 μM Staurosporine
DMSO concentration have to stay below 2% during the kinase reaction Assays were performed in either 96 or 384-well plates. The final outcome of the coupled reactions provided by the kit is the release of the fluorescent product Resorufin and has been measured with a multilabel HTS counter VICTOR V (PerkinElmer) using an excitation filter at 544 nm and an emission filter at 580 nm.

The compounds names given above were generated with MDL ISIS/DRAW 2.5 SP 2, Autonom 2000.

EXAMPLES

The following Examples illustrate the invention.
General Experimental Conditions
Compounds were analyzed on HPLC-MS (Agilent 1100 Series) with ESI+ (API 2000) and equipped with different brands of C18 columns. Analysis of final compounds was performed using RP-C18 Gemini column, (150×4.6 mm, 5 μm). Elution was done with different gradients of A/B (B=$CH_3CN$+0.1% formic acid; A=$H_2O$+0.1% formic acid) (15 min, flow rate=1 mL/min).

MW calculated is an isotopic average and the "found mass" refers to the most abundant isotope detected in the LC-MS.

NMR was recorded in a Bruker Avance II 300 spectrometer.

Intermediate 1

2-Phenyl-imidazo[2,1-b][1,3,4]thiadiazole

To a suspension of 2-amino-5-phenylthiadiazole (1 g, 5.40 mmol) in water (30 mL) was added a water solution of chloroacetaldehyde (50% wt, 1.5 eq, 1 mL). n-Butanol (5 mL) was added in order to solubilize the starting material. The mixture was heated at reflux for 30 hours. After cooling down to room temperature, the mixture was neutralized with sodium bicarbonate (sat. aq. solution) and extracted with dichloromethane (3×30 mL). The combined organic layers were dried over sodium sulfate and the solvent evaporated under vacuum. The crude product was purified by flash chromatography (Biotage™, ethyl acetate:hexane, 3:7 to 7:3) to provide 490 mg of 2-phenyl-imidazo[2,1-b][1,3,4]thiadiazole (45% yield) as a white solid.

$^1$H NMR (300 MHz, CDCl$_3$): δ 7.84 (d, J=5.4 Hz, 2H), 7.75 (s, 1H), 7.49 (s, 3H), 7.31 (s, 1H).
MS (ES+) m/z 202 (M+H)$^+$ (MW: 201.2)

Intermediate 2

2-Amino-5-bromo-[1,3,4]thiadiazole

Sodium bicarbonate (8.14 g, 96.90 mmol) and bromine (2.5 mL, 48.45 mmol) were added to a solution of 2-amino-1,3,4-thiadiazole (5 g, 48.45 mmol) in methanol (70 mL). The reaction mixture was stirred at room temperature until disappearance of starting material (30-40 minutes). The solvent was removed under vacuum and the crude product was triturated with methanol-diethyl ether to yield 2-amino-5-bromo-[1,3,4]thiadiazole as white solid. The mother liquor containing a bit of product was submitted to flash chromatography eluting with dichloromethane-methanol (99% yield).

$^1$H NMR (300 MHz, DMSO-d$_6$): δ 7.52 (br s, 2H).
MS (ES+) m/z 181 (M+H)$^+$ (MW: 180.0)

Intermediate 3

2-Bromo-imidazo[2,1-b][1,3,4]thiadiazole

To a suspension of 2-amino-5-bromo-1,3,4-thiadiazole (1.65 g, 9.15 mmol) in water (27 mL) was added a water solution of chloroacetaldehyde (50% wt, 1.7 mL). The mixture was stirred at reflux. After 10 hours, a second addition of chloroacetaldehyde (1.5 eq, 1.7 mL) was done and stirring was continued until disappearance of starting material (20 hours). After cooling, the reaction mixture was neutralized with sodium bicarbonate (sat. aq. solution) and extracted with dichloromethane (3×30 mL). The combined organic layers were dried over sodium sulphate and the solvent evaporated under vacuum. The crude product was triturated with diethyl ether to yield 2-bromo-imidazo[2,1-b][1,3,4]thiadiazole as a white solid. The mother liquor was purified by flash chromatography (Biotage™, ethyl acetate:hexane, 3:7 to 7:3) to yield another batch of compound (20% global yield) as a white solid.

$^1$H NMR (300 MHz, CDCl$_3$): δ 7.64 (s, 1H), 7.24 (s, 1H).
MS (ES+) m/z 204 (M+H)$^+$ (MW: 204.05).

General Procedure a for the Preparation of Intermediates 4-8

2-Bromo-imidazo[2,1-b][1,3,4]thiadiazole (1 eq) and the appropriate amine (e.g. cyclopropanemethyl amine) (4.5 eq) were stirred at 135° C. under microwave irradiation (200 W) for 5 minutes. After cooling down to room temperature, the reaction mixture was diluted with dichloromethane and purified by flash chromatography (Biotage™, silica, dichloromethane:methanol) to yield the desired product (e.g. cyclopropylmethyl-imidazo[2,1-b][1,3,4]thiadiazol-2-yl-amine).

Intermediate 4

Cyclopropylmethyl-imidazo[2,1-b][1,3,4]thiadiazol-2-yl-amine

The title compound was obtained in 89% yield.
$^1$H NMR (300 MHz, CDCl$_3$): δ 7.27 (brs, 1H), 7.21 (d, J=1.3, 1H), 6.83 (s, 1H), 3.01 (dd, J=5.1, 6.9, 2H), 1.04-0.80 (m, 1H), 0.43-0.28 (m, 2H), 0.13-0.05 (m, 2H).
MS (ES+) m/z 195.10 (M+H)$^+$ (MW: 194.26).

Intermediate 5

(3,4-Dichlorobenzyl)-imidazo[2,1-b][1,3,4]thiadiazol-2-yl-amine

The title compound was obtained as a white solid in a 65% yield.
$^1$H NMR (300 MHz, DMSO-d$_6$) 5 ppm 8.45 (t, J=5.6 Hz, 1H), 7.70 (d, J=1.3 Hz, 1H), 7.63 (dd, J=5.0, 3.2 Hz, 2H), 7.37 (dd, J=8.3, 1.9 Hz, 1H), 6.99 (d, J=1.2 Hz, 1H), 4.50 (d, J=5.6 Hz, 2H).
MS (ES+) m/z 299 (M+H)$^+$ (MW: 299.2).

Intermediate 6

(4-Fluoro-benzyl)-imidazo[2,1-b][1,3,4]thiadiazol-2-yl-amine

The title compound was obtained in 58% yield.
$^1$H NMR (300 MHz, CDCl$_3$): δ 7.98 (brs, 1H), 7.47-7.31 (m, 3H), 7.06 (t, J=8.7, 2H), 6.63 (d, J=1.4, 1H), 4.54 (d, J=5.2, 2H).
MS (ES+) m/z 249.05 (M+H)$^+$ (MW: 248.28).

Intermediate 7

Imidazo[2,1-b][1,3,4]thiadiazol-2-yl-(2-methoxy-ethyl)-amine

The title compound was obtained in 84% yield.
$^1$H NMR (300 MHz, CDCl$_3$): δ 7.67 (brs, 1H), 7.43 (s, 1H), 7.06 (s, 1H), 3.68-3.47 (m, 4H), 3.35 (s, 3H).
MS (ES+) m/z 199.10 (M+H)$^+$ (MW: 198.25).

Intermediate 8

Imidazo[2,1-b][1,3,4]thiadiazol-2-yl-isobutyl-amine

The title compound was obtained in 89% yield.
$^1$H NMR (300 MHz, CDCl$_3$): δ 7.95 (t, J=5.5, 1H), 7.44 (d, J=1.3, 1H), 7.01 (d, J=1.4, 1H), 3.20 (dd, J=5.7, 6.9, 2H), 2.00 (dp, J=6.7, 13.4, 1H), 0.99 (d, J=6.7, 6H).
MS (ES+) m/z 197.10 (M+H)$^+$ (MW: 196.28).

General Procedure B for the Synthesis of Intermediates 9-14.

A mixture of the appropriate imidazo[2,1-b][1,3,4]thiadiazol-2-yl-substituted amine (e.g. imidazo[2,1-b][1,3,4]thiadiazol-2-yl-isobutyl-amine) (1.0 eq) and N-iodosuccinimide (1.1 eq) in N,N-dimethylformamide (about 4 mL/mmol) was stirred at room temperature for 16 hours. The reaction was diluted with dichloromethane and washed with 10% solution of sodium thiosulphate and saturated solution of sodium chloride. The organic layer was dried (sodium sulfate), filtered and concentrated. The crude mixture was purified to give the desired product (e.g. (5-iodo-imidazo[2,1-b][1,3,4]thiadiazol-2-yl)-isobutyl-amine).

Intermediate 9

(3,4-Dichlorobenzyl)-(5-iodo-imidazo[2,1-b][1,3,4]thiadiazol-2-yl)-amine

The title compound was obtained as a white solid in a 45% yield after purification by column chromatography (Biotage/Flash, silica, ethyl acetate:hexane 2.5:7.5 to 7.5:2.5).

$^1$H NMR (300 MHz, DMSO-d$_6$): δ 8.49 (t, J=5.4, 1H), 7.45 (dd, J=5.7, 8.1, 2H), 7.20 (t, J=8.6, 2H), 7.04 (s, 1H), 4.48 (d, J=5.5, 2H).

MS (ES+) m/z 374 (M+H)$^+$ (MW: 374.18).

Intermediate 10

(5-Iodo-imidazo[2,1-b][1,3,4]thiadiazol-2-yl)-(2-methoxy-ethyl)-amine

The title compound was obtained in 52% yield after purification by column chromatography (Biotage/Flash, silica, methanol:dichloromethane 0.1:9.9 to 1:9).

$^1$H NMR (300 MHz, CDCl$_3$): δ 7.13 (s, 1H), 5.84 (brs, 1H), 3.70-3.53 (m, 4H), 3.42 (s, 3H).

MS (ES+) m/z 324.90 (M+H)$^+$ (MW: 324.14).

Intermediate 11

(5-Iodo-imidazo[2,1-b][1,3,4]thiadiazol-2-yl)-isobutyl-amine

The title compound was obtained in 59% yield after purification by column chromatography (Biotage/Flash, silica, ethylacetate:dichloromethane 0.1:9.9 to 3:7).

$^1$H NMR (300 MHz, CDCl$_3$): δ 7.03 (s, 1H), 5.64 (brs, 1H), 3.12 (td, J=0.9, 6.4, 2H), 1.90 (dt, J=6.7, 13.4, 1H), 0.94 (s, 3H), 0.92 (s, 3H).

MS (ES+) m/z 323.00 (M+H)$^+$ (MW: 322.17).

Intermediate 12

Cyclopropylmethyl-(5-iodo-imidazo[2,1-b][1,3,4]thiadiazol-2-yl)-amine

The title compound was obtained in 59% yield after purification by column chromatography (Biotage/Flash, silica, ethylacetate:dichloromethane 0.1:9.9 to 3:7).

$^1$H NMR (300 MHz, CDCl$_3$): δ 7.10 (s, 1H), 5.21 (brs, 1H), 3.24 (dd, J=5.4, 7.1, 2H), 1.14 (ddd, J=4.9, 7.6, 12.3, 1H), 0.73-0.50 (m, 2H), 0.31 (q, J=5.1, 2H).

MS (ES+) m/z 321.00 (M+H)$^+$ (MW: 320.15).

Intermediate 13

5-Iodo-2-phenyl-imidazo[2,1-b][1,3,4]thiadiazole

The title compound was obtained in a 62% yield after purification by column chromatography (Biotage/Flash, silica, hexane:ethyl acetate, 7.5:2.5 to 2.5:7.5).

$^1$H NMR (300 MHz, CDCl$_3$): δ 7.87 (m, 2H), 748 (m, 3H), 7.30 (s, 1H).

MS (ES+) m/z 328 (M+H)$^+$ (MW: 327.1).

Intermediate 14

(3,4-Dichlorobenzyl)-(5-iodo-imidazo[2,1-b][1,3,4]thiadiazol-2-yl)-amine

The title compound was obtained as a yellow solid in a 52% yield after purification by column chromatography (Biotage/Flash, silica, hexane:ethyl acetate, 7.5:2.5 to 2.5:7.5).

$^1$H NMR (300 MHz, CDCl$_3$): δ 8.55 (t, J=5.7 Hz, 1H), 7.66 (dd, J=5.0, 14.2 Hz, 2H), 7.40 (dd, J=1.8, 8.3 Hz, 1H), 7.04 (s, 1H), 4.50 (d, J=5.7 Hz, 2H).

MS (ES+) m/z 425 (M+H)$^+$ (MW: 425.1).

General Procedure C for the Synthesis of Intermediates 15-18.

A mixture of the appropriate iodo-imidazo[2,1-b][1,3,4]thiadiazol-2-yl-substituted-amine (e.g. (5-iodo-imidazo[2,1-b][1,3,4]thiadiazol-2-yl)-isobutyl-amine) (1.0 eq) and N-chlorosuccinimide (1.1 eq) in acetonitrile (about 6 mL/mmol) was heated under microwave irradiation at 180° C. for 15 minutes. The reaction was diluted with dichloromethane and washed with water. The organic layer was dried (sodium sulfate), filtered and concentrated. The crude mixture was purified by column chromatography (Biotage™/Flash, silica) to give the desired product (e.g. (6-chloro-5-iodo-imidazo[2,1-b][1,3,4]thiadiazol-2-yl)-isobutyl-amine).

Intermediate 15

(6-Chloro-5-iodo-imidazo[2,1-b][1,3,4]thiadiazol-2-yl)-(4-fluoro-benzyl)-amine

The title compound was obtained in 48% yield after purification by column chromatography (Biotage/Flash, silica, methanol:dichloromethane 0.1:9.9 to 1:9).

$^1$H NMR (300 MHz, CDCl$_3$): δ 7.37 (dd, J=5.5, 8.5, 2H), 7.15-6.99 (m, 2H), 5.47 (brs, 1H), 4.57 (d, J=5.2, 2H).

MS (ES+) m/z 408.90 (M+H)$^+$ (MW: 408.62).

Intermediate 16

(6-Chloro-5-iodo-imidazo[2,1-b][1,3,4]thiadiazol-2-yl)-(2-methoxy-ethyl)-amine

The title compound was obtained in 89% yield after purification by column chromatography (Biotage/Flash, silica, methanol:dichloromethane 0.1:9.9 to 3:7).

$^1$H NMR (300 MHz, CDCl$_3$): δ 6.16 (brs, 1H), 3.70-3.52 (m, 4H), 3.39 (s, 3H).

MS (ES+) m/z 458.90 (M+H)$^+$ (MW: 358.59).

Intermediate 17

(6-Chloro-5-iodo-imidazo[2,1-b][1,3,4]thiadiazol-2-yl)-isobutyl-amine

The title compound was obtained in 89% yield after purification by column chromatography (Biotage/Flash, silica, ethylacetate:dichloromethane 0.1:9.9 to 1:9).

$^1$H NMR (300 MHz, CDCl$_3$): δ 5.54 (brs, 1H), 3.09 (ddd, J=2.3, 6.8, 13.5, 2H), 1.93-1.78 (m, 1H), 0.88 (s, 3H), 0.87 (s, 3H).

MS (ES+) m/z 356.90 (M+H)$^+$ (MW: 356.61).

Intermediate 18

(6-Chloro-5-iodo-imidazo[2,1-b][1,3,4]thiadiazol-2-yl)-cyclopropylmethyl-amine The title compound was obtained in 42% yield after purification by column chromatography (Biotage/Flash, silica, ethylacetate:dichloromethane 0.1:9.9 to 3:7).

$^1$H NMR (300 MHz, CDCl$_3$): δ 5.52 (brs, 1H), 3.26 (ddd, J=4.1, 7.9, 12.0, 2H), 1.18-1.14 (m, 1H), 0.69-0.52 (m, 2H), 0.39-0.21 (m, 2H).

MS (ES+) m/z 354.90 (M+H)$^+$ (MW: 354.55).

General Procedure D for the Synthesis of Examples 1-12.

Cesium carbonate (3.0 eq) dissolved in water (about 1 mL/mmol) was added over a mixture of the appropriate 5-iodo-imidazo[2,1-b][1,3,4]thiadiazol-2-yl-substituted compound (e.g. 5-iodo-2-phenyl imidazo[2,1-b][1,3,4]thiadiazole) (1.0 eq), the corresponding boronic acid (e.g. phenylboronic acid) (1.1 eq) and tetrakis(triphenylphosphine) palladium(0) (10% mol) in 1,4-dioxane (about 3.7 mL/mmol). The mixture was heated under microwave irradiation at 135-140° C. for 30 minutes. The reaction mixture was diluted with dichloromethane and washed with water. (Alternatively the reaction mixture was filtered through a celite pad which was washed with dichloromethane). The organic layer was dried (sodium sulphate), filtered and concentrated in vacuo. The crude mixture was purified by column chromatography (different methods) to give the desired product (e.g. 2,5-diphenyl-imidazo[2,1-b][1,3,4]thiadiazole).

Example 1

2,5-Diphenyl-imidazo[2,1-b][1,3,4]thiadiazole

The title compound was obtained after filtration of the reaction mixture through a celite pad and purification by chromatography (Isolute cartridge flash Si II, 5 g, hexane: ethyl acetate) as a syrup in a 79% yield.

$^1$H NMR (300 MHz, CDCl$_3$): δ 7.89 (m, 4H), 7.54 (s, 1H), 7.44 (m, 5H), 7.27 (t, J=7.4 Hz, 1H).

MS (ES+) m/z 278 (M+H)$^+$ (MW: 277.3).

Example 2

6-(2-Phenyl-imidazo[2,1-b][1,3,4]thiadiazole-5-yl)-1H-indole

The title compound was obtained after filtration of the reaction mixture through a celite pad and purification by chromatography (Isolute cartridge flash Si II, 5 g, hexane: ethyl acetate) as a yellow solid in a 65% yield.

$^1$H NMR (300 MHz, CDCl$_3$): δ 8.41 (s, 1H=NH), 8.07 (s, 1H), 7.86 (m, 2H), 7.59 (m, 3H), 7.44 (m, 3H), 7.19 (dd, J=2.2, 4.9 Hz, 1H), 6.52 (s, 1H).

MS (ES+) m/z 317 (M+H)$^+$ (MW: 316.4).

Example 3

[4-(2-Phenyl-imidazo[2,1-b][1,3,4]thiadiazole-5-yl)-phenyl]methanol

The title compound was obtained after filtration of the reaction mixture through a celite pad and purification by chromatography (Isolute cartridge flash Si II, 5 g, hexane: ethyl acetate) as a white solid in a 48% yield.

$^1$H NMR (300 MHz, DMSO-d$_6$): δ 8.02 (m, 4H), 7.81 (s, 1H), 7.62 (m, 3H), 7.46 (d, J=8.1 Hz, 2H), 5.26 (t, J=5.7 Hz, 1H), 4.55 (d, J=5.7 Hz, 2H).

MS (ES+) m/z 308 (M+H)$^+$ (MW: 307.4).

Example 4

5-(4-Fluorophenyl)-2-phenyl-imidazo[2,1-b][1,3,4]thiadiazole

The title compound was obtained after filtration of the reaction mixture through a celite pad and purification by chromatography (Isolute cartridge flash Si II, 5 g, hexane: ethyl acetate) as a white solid in a 49% yield.

$^1$H NMR (300 MHz, CDCl$_3$): δ 7.96 (m, 4H), 7.52 (m, 4H), 7.16 (t, J=8.7 Hz, 2H).

MS (ES+) m/z 296 (M+H)$^+$ (MW: 295.3).

Example 5

2-Phenyl-5-pyridin-3-yl-imidazo[2,1-b][1,3,4]thiadiazole

The title compound was obtained after filtration of the reaction mixture through a celite pad and purification by chromatography (Isolute cartridge flash Si II, 5 g, hexane: ethyl acetate) as a white solid in a 69% yield.

$^1$H NMR (300 MHz, CDCl$_3$): δ 9.23 (d, J=2.2 Hz, 1H), 8.54 (d, J=4.8 Hz, 1H), 8.27 (d, J=8.0 Hz, 1H), 7.65 (s, 1H), 7.91 (m, 2H), 7.48 (m, 3H), 7.38 (dd, J=4.8, 8.0 Hz, 1H).

MS (ES+) m/z 279 (M+H)$^+$ (MW: 278.3).

Example 6

1-{3-[2-(Cyclopropylmethyl-amino)-imidazo[2,1-b][1,3,4]thiadiazol-5-yl]-phenyl}-ethanone The title compound was obtained after filtration of the reaction mixture through a celite pad and purification by chromatography (Isolute cartridge flash Si II, 5 g, hexane: ethyl acetate) as a white solid in a 38% yield.

$^1$H NMR (300 MHz, DMSO-d$_6$): δ 8.60 (s, 1H), 8.24 (s, 1H), 8.17 (d, J=12.8 Hz, 1H), 7.59 (m, 2H), 3.25 (t, J=6.0 Hz, 2H), 2.63 (s, 3H), 1.20 (m, 1H), 0.53 (d, J=6.5 Hz, 2H), 0.31 (d, J=4.6 Hz, 2H).

MS (ES+) m/z 313 (M+H)$^+$ (MW: 312.4).

Example 7

1-{3-[2-(3,4-Dichlorobenzyl-amino)-imidazo[2,1-b][1,3,4]thiadiazol-5-yl]-phenyl}-ethanone The title compound was obtained after filtration of the reaction mixture through a celite pad and purification by chromatography (Isolute cartridge flash Si II, 5 g, hexane: ethyl acetate) as a white solid in a 33% yield.

$^1$H NMR (300 MHz, DMSO-d$_6$): δ 8.70 (s, 1H), 8.53 (s, 1H), 8.12 (d, J=7.9 Hz, 1H), 7.85 (d, J=7.8 Hz, 1H), 7.73 (s, 1H), 7.61 (m, 3H), 7.47 (d, J=8.2 Hz, 1H), 4.58 (d, J=5.3 Hz, 2H), 2.59 (s, 3H).

MS (ES+) m/z 417 (M+H)$^+$ (MW: 417.32).

Example 8

4-[2-(4-Fluorobenzylamino)-imidazo[2,1-b][1,3,4]thiadiazol-5-yl]-phenol

The title compound was obtained after filtration of the reaction mixture through a celite pad and purification by chromatography (Isolute cartridge flash Si II, 5 g, hexane: ethyl acetate) as a brownish solid in a 24% yield.

$^1$H NMR (300 MHz, methanol-d$_4$): δ 7.67 (d, J=8.7 Hz, 2H), 7.40 (dd, J=5.6, 8.3 Hz, 2H), 7.17 (s, 1H), 7.04 (t, J=8.7 Hz, 2H), 6.79 (d, J=8.7 Hz, 2H), 4.49 (s, 2H).

MS (ES+) m/z 341 (M+H)$^+$ (MW: 340.38).

Example 9

[6-Chloro-5-(4-methoxy-phenyl)-imidazo[2,1-b][1,3,4]thiadiazol-2-yl]-(4-fluoro-benzyl)-amine The title compound was obtained in 7% yield after purification by column chromatography (Biotage/Flash, silica, ethyl acetate:dichloromethane 0.1:9.9 to 3:7) and by semi-preparative-HPLC (Gemini C18 (150×10 mm; 5 um), Solvent A: water with 0.1% formic acid; Solvent B: acetonitrile with 0.1% formic acid. Gradient: 60% of A to 20% of B).

$^1$H NMR (300 MHz, CDCl$_3$): δ 9.37 (s, 1H), 7.73 (d, J=8.9, 2H), 7.37 (dd, J=5.5, 8.3, 2H), 6.96 (t, J=9.2, 4H), 4.57 (d, J=5.9, 2H), 3.79 (s, 3H).

MS (ES+) m/z 389.00 (M+H)$^+$ (MW: 388.85).

Example 10

[6-Chloro-5-(3,4-dimethoxy-phenyl)-imidazo[2,1-b][1,3,4]thiadiazol-2-yl]-(2-methoxy-ethyl)-amine The title compound was obtained in 19% yield after purification by column chromatography (Biotage/Flash, silica, ethyl acetate:dichloromethane 0.1:9.9 to 3:7).

$^1$H NMR (300 MHz, CDCl$_3$): δ 7.51 (dd, J=1.1, 7.2, 2H), 6.97 (d, J=8.8, 1H), 3.94 (s, 6H), 3.63-3.57 (m, 6H), 3.40 (s, 3H).

MS (ES+) m/z 369.00 (M+H)$^+$ (MW: 368.07).

Example 11

1-[3-(6-Chloro-2-isobutylamino-imidazo[2,1-b][1,3,4]thiadiazol-5-yl)-phenyl]-ethanone The title compound was obtained in 31% yield after purification by column chromatography (Biotage/Flash, silica, ethyl acetate:dichloromethane 0.1:9.9 to 3:7).

$^1$H NMR (300 MHz, CDCl$_3$): δ 7.51 (dd, J=1.1, 7.2, 2H), 6.97 (d, J=8.8, 1H), 3.94 (s, 6H), 3.63-3.57 (m, 6H), 3.40 (s, 3H).

MS (ES+) m/z 369.00 (M+H)$^+$, (MW: 348.85).

Example 12

[6-Chloro-5-(3-dimethylamino-phenyl)-imidazo[2,1-b][1,3,4]thiadiazol-2-yl]-cyclopropylmethyl-amine The title compound was obtained in 37% yield after purification by column chromatography (Biotage/Flash, silica, ethyl acetate:dichloromethane 0.1:9.9 to 3:7).

$^1$H NMR (300 MHz, CDCl$_3$): δ 7.36-7.24 (m, 3H), 6.70 (d, J=7.5, 1H), 5.38 (brs, 1H), 3.34-3.17 (m, 2H), 3.00 (s, 6H), 1.13 (ddd, J=4.3, 7.4, 12.0, 1H), 0.68-0.51 (m, 2H), 0.32-0.27 (m, 2H).

MS (ES+) m/z 348.00 (M+H)$^+$, (MW: 347.87).

General Procedure E for the Preparation of Examples 13-14

To a solution of the appropriate imidazo[2,1-b][1,3,4]thiadiazol-2-yl-amine (e.g. cyclopropylmethyl-imidazo[2,1-b][1,3,4]thiadiazol-2-yl-amine) (1 eq) in dry methanol (5 mL/mmmol) were added the appropriate secondary amine (e.g. morpholine) (1.2 eq), glacial acetic acid (0.125 mL/mmol) and formaldehyde (37% aq. sol., 5 eq). The mixture was heated at reflux for 2 hours under argon atmosphere. Methanol was removed under vacuum and the residue was diluted with dichloromethane and water. The aqueous layer was extracted with dichloromethane (3×) and the combined organic layers were washed with brine and dried over sodium sulfate. The crude product was purified by flash chromatography (methanol:dichlormethane, 0:10 to 2.5:7.5) to yield the required product (e.g. cyclopropylmethyl-(5-morpholin-4-ylmethyl-imidazo[2,1-b][1,3,4]thiadiazol-2-yl)-amine).

Example 13

Cyclopropylmethyl-(5-morpholin-4-ylmethyl-imidazo[2,1-b][1,3,4]thiadiazol-2-yl)-amine The title compound was isolated as a syrup in a 32% yield.

$^1$H NMR (300 MHz, CDCl$_3$): δ 7.20 (s, 1H), 6.34 (br s, 1H), 3.95 (m, 6H), 3.44 (t, J=6.0 Hz, 2H), 2.77 (d, J=4.3 Hz, 4H), 1.36 (m, 1H), 0.82 (q, J=5.6 Hz, 2H), 0.53 (q, J=4.9 Hz, 2H).

MS (ES+) m/z 294 (M+H)$^+$ (MW: 293.4).

Example 14

2-Dimethylamino-imidazo[2,1-b][1,3,4]thiadiazole-5-carboxylic acid benzyl-methyl-amide 2-Dimethylamino-imidazo[2,1-b][1,3,4]thiadiazole-5-carbaldehyde (116 mg, 0.591 mmol) was dissolved in dry acetonitrile (4 mL) and N-methylbenzylamine (0.768 mmol, 0.1 mL) and t-butylhydroperoxide (0.768 mmol, 5.5M, 0.14 mL) were added. The mixture was heated at 80° C. for 10 hours. The reaction mixture was diluted with water (4 mL) at room temperature and extracted with dichloromethane (3×8 mL). The combined organic layer was dried over sodium sulphate and concentrated in vacuo. The crude product was purified by flash chromatography (Isolute cartridge SiII, ethyl acetate:dichloromethane, 1:9 to 10:0) yielding 54 mg of 2-dimethylamino-imidazo[2,1-b][1,3,4]thiadiazole-5-carboxylic acid benzyl-methyl-amide as yellowish solid (29% yield).

$^1$H NMR (300 MHz, CDCl$_3$) 5 ppm 7.26 (m, 6H), 4.72 (s, 2H), 3.06 (s, 6H), 3.01 (s, 3H).

MS (ES+) m/z 316 (M+H)$^+$ (MW: 315.4).

Intermediate 19

2-(4-Fluoro-phenoxy)-imidazo[2,1-b][1,3,4]thiadiazole

A mixture of 2-bromo-imidazo[2,1-b][1,3,4]thiadiazole (1.0 g, 4.90 mmol) and 4-fluorophenol (2.2 g, 19.60 mmol) was heated under microwave irradiation at 135° C. for 3.5 hours. On cooling, the mixture was diluted with dichloromethane (7 mL), adsorbed in silica and purified by column chromatography (Biotage™/Flash, silica, methanol:dichloromethane 0.2:9.8 to 2:8) to give 2-(4-fluoro-phenoxy)-imidazo[2,1-b][1,3,4]thiadiazole as a white solid (610 mg, 53% yield).

$^1$H-NMR (300 MHz, CDCl$_3$): δ 7.54 (d, J=1.3 Hz, 1H), 7.29 (m, 2H), 7.21 (d, J=1.2 Hz, 1H), 7.14 (m, 2H).

MS (ES+) m/z 236 (M+H)$^+$ (MW: 235.24).

Intermediate 20

2-(4-Fluoro-phenoxy)-5-iodo-imidazo[2,1-b][1,3,4]thiadiazole 2-(4-Fluoro-phenoxy)-imidazo[2,1-b][1,3,4]thiadiazole (0.6 g, 2.55 mmol) was dissolved in N,N-dimethylformamide (10 mL) and N-iodosuccinimide (0.63 g, 2.81 mmol) was added in one portion. The reaction mixture was stirred at room temperature overnight in the absence of light. The yellow suspension was filtered and rinsed with diethylether (2×2 mL) to give 2-(4-fluoro-phenoxy)-5-iodo-imidazo[2,1-b][1,3,4]thiadiazole as a white solid (0.65 g, 71%). The filtrate was evaporated and the residue was triturated with diethylether (6 mL) and filtered. This solid was purified by column chromatography (Biotage™/Flash, silica, methanol:dichloromethane 0:10 to 1:9) to give 2-(4-fluoro-phenoxy)-5-iodo-imidazo[2,1-b][1,3,4]thiadiazole as a white solid (0.15 g, 16% yield).
$^1$H-NMR (300 MHz, CDCl$_3$): δ 7.24 (dd, J=4.3, 9.1 Hz, 2H), 7.17 (s, 1H), 7.07 (t, J=8.5 Hz, 2H).
MS (ES+) m/z 360 (M+H)$^+$, (MW: 361.13)

Example 15

{3-[2-(4-Fluoro-phenoxy)-imidazo[2,1-b][1,3,4]thiadiazol-5-yl]-phenyl}-dimethyl-amine 2-(4-Fluoro-phenoxy)-5-iodo-imidazo[2,1-b][1,3,4]thiadiazole (0.13 g, 0.36 mmol) was suspended in 1,4-dioxane (1.5 mL) at room temperature and argon was bubbled into the mixture while tetrakis(triphenylphosphine)palladium(0) (42 mg, 0.036 mmol), 3-(N,N-dimethylamino)phenylboronic acid (68 mg, 0.41 mmol), cesium carbonate (235 mg, 0.72 mmol, 2.0 eq), and water (1.5 mL) were added. The mixture was deoxygenated for 10 minutes and heated under microwave irradiation at 140° C. for 1 hour. On cooling, the mixture was diluted with dichloromethane (7 mL), adsorbed in silica and purified by column chromatography (Biotage™/Flash, silica, methanol:dichloromethane 0.2:9.8 to 2:8). The obtained residue was crystallized from methanol:1,2-dichloroethane (1:1, 1.5 mL) and filtered to give {3-[2-(4-fluoro-phenoxy)-imidazo[2,1-b][1,3,4]thiadiazol-5-yl]-phenyl}-dimethyl-amine as a white solid (13 mg, 10% yield).
$^1$H-NMR (300 MHz, CDCl$_3$) δ 7.51 (s, 1H), 7.37 (m, 2H), 7.29 (m, 2H), 7.16 (m, 3H), 6.75 (d, J=8.2 Hz, 1H), 2.94 (s, 6H).
MS (ES+) m/z 355 (M+H)$^+$ (MW: 354.41).

Example 16

4-[2-(4-Fluoro-phenoxy)-imidazo[2,1-b][1,3,4]thiadiazol-5-yl]-phenol 2-(4-Fluoro-phenoxy)-5-iodo-imidazo[2,1-b][1,3,4]thiadiazole (0.15 g, 0.42 mmol) was suspended in 1,4-dioxane (1.5 mL) at room temperature and argon was bubbled into the mixture while tetrakis(triphenylphosphine)palladium(0) (48 mg, 0.042 mmol), 4-hydroxyphenylboronic acid (66 mg, 0.48 mmol), cesium carbonate (271 mg, 0.83 mmol) and water (1.5 mL) were added. The mixture was deoxygenated for 10 minutes and heated under microwave irradiation at 140° C. for 20 minutes. On cooling, the mixture was diluted with dichloromethane (7 mL), adsorbed in silica and purified by column chromatography (Biotage™/Flash, silica, methanol:dichloromethane 0.2:9.8 to 1.5:7.5). The product obtained was treated with dichloromethane (5 mL) and filtered to give 4-[2-(4-fluoro-phenoxy)-imidazo[2,1-b][1,3,4]thiadiazol-5-yl]-phenol as a white solid (37 mg, 27% yield).
$^1$H-NMR (300 MHz, DMSO-d$_6$) δ 9.69 (s, 1H), 7.67 (m, 4H), 7.53 (s, 1H), 7.44 (t, J=8.8 Hz, 2H), 6.87 (d, J=8.7 Hz, 2H).
MS (ES+) m/z 328 (M+H)$^+$ (MW: 327.34).

Example 17

N-{4-[2-(4-Fluoro-phenoxy)-imidazo[2,1-b][1,3,4]thiadiazol-5-yl]-phenyl}-acetamide 2-(4-Fluoro-phenoxy)-5-iodo-imidazo[2,1-b][1,3,4]thiadiazole (0.15 g, 0.42 mmol) was suspended in 1,4-dioxane (1.5 mL) at room temperature and argon was bubbled into the mixture while dichlorobis(triphenylphosphine)palladium(II) (29 mg, 0.042 mmol), 4-acetamidophenylboronic acid (85 mg, 0.48 mmol), cesium carbonate (271 mg, 0.83 mmol) and water (1.5 mL) were added. The mixture was deoxygenated for 10 minutes and heated under microwave irradiation at 140° C. for 20 minutes. On cooling, the resulting suspension was diluted with dichloromethane (7 mL), adsorbed in silica and purified by column chromatography (Biotage™/Flash, silica, methanol:dichloromethane 0.2:9.8 to 2:8). The residue obtained was treated with diethylether (7 mL) and filtered to give 66 mg of N-{4-[2-(4-fluoro-phenoxy)-imidazo[2,1-b][1,3,4]thiadiazol-5-yl]-phenyl}-acetamide as a white solid (43%).
$^1$H-NMR (300 MHz, DMSO-d$_6$): δ 10.04 (s, 1H), 7.78 (d, J=8.7 Hz, 2H), 7.63 (m, 5H), 7.41 (dd, J=5.7, 11.8 Hz, 2H), 2.05 (s, 3H).
MS (ES+) m/z 369 (M+H)$^+$ (MW: 368.39).

Intermediate 21

(4-Fluoro-phenyl)-imidazo[2,1-b][1,3,4]thiadiazol-2-yl-amine

A mixture of 2-bromo-imidazo[2,1-b][1,3,4]thiadiazole (1.0 g, 4.90 mmol) and 4-fluoroaniline (1.86 mL, 19.60 mmol) was heated under microwave irradiation at 135° C. for 15 minutes. On cooling, the mixture was diluted with dichloromethane (10 mL) and purified by column chromatography (Biotage™/Flash, silica, methanol:dichloromethane 0.2:9.8 to 1:9). The residue obtained was treated with dichloromethane (5 mL) and filtered to give (4-fluoro-phenyl)-imidazo[2,1-b][1,3,4]thiadiazol-2-yl-amine as a beige solid (117 mg, 10% yield).
$^1$H-NMR (300 MHz, DMSO-d$_6$): δ 10.47 (s, 1H), 7.87 (d, J=1.3 Hz, 1H), 7.57 (m, 2H), 7.23 (t, J=8.9 Hz, 2H), 7.10 (d, J=1.3 Hz, 1H).
MS (ES+) m/z 235 (M+H)$^+$ (MW: 234.25).

Intermediate 22

(4-Fluoro-phenyl)-(5-iodo-imidazo[2,1-b][1,3,4]thiadiazol-2-yl)-amine (4-Fluoro-phenyl)-imidazo[2,1-b][1,3,4]thiadiazol-2-yl-amine (0.117 g, 0.50 mmol) was suspended in N,N-dimethylformamide (3 mL) and N-iodosuccinimide (0.124 g, 0.55 mmol) was added in one portion. The reaction mixture was stirred at room temperature for 2 hours in the absence of light. The mixture was evaporated and the residue was purified by column chromatography (Biotage™/Flash, silica, methanol:dichloromethane 0.4:9.6 to 1:9) to give 0.13 g of (4-fluorophenyl)-(5-iodo-imidazo[2,1-b][1,3,4]thiadiazol-2-yl)-amine as an off-white solid (72% yield).

$^1$H-NMR (300 MHz, DMSO-$d_6$): δ 10.59 (s, 1H), 7.59 (dd, J=4.8, 9.1 Hz, 2H), 7.27 (t, J=8.9 Hz, 2H), 7.15 (s, 1H).

MS (ES+) m/z 360 (M+H)$^+$ (MW: 360.15).

Example 18

4-[2-(4-Fluoro-phenylamino)-imidazo[2,1-b][1,3,4]thiadiazol-5-yl]-phenol (4-Fluoro-phenyl)-(5-iodo-imidazo[2,1-b][1,3,4]thiadiazol-2-yl)-amine (0.065 g, 0.18 mmol) was suspended in 1,4-dioxane (1 mL) at room temperature, and argon was bubbled into the mixture while tetrakis(triphenylphosphine)-palladium(0) (21 mg, 0.018 mmol), 4-hydroxyphenylboronic acid (21 mg, 0.21 mmol), cesium carbonate (118 mg, 0.36 mmol) and water (1 mL) were added. The mixture was deoxygenated for 10 minutes and heated under microwave irradiation at 140° C. for 30 minutes. On cooling, the mixture was diluted with dichloromethane (5 mL), adsorbed in silica and purified by column chromatography (Biotage™/Flash, silica, methanol:dichloromethane 0.4:9.6 to 1:9) to give 4-[2-(4-fluoro-phenylamino)-imidazo[2,1-b][1,3,4]thiadiazol-5-yl]-phenol as a beige solid (21 mg, 36% yield).

$^1$H-NMR (300 MHz, DMSO-$d_6$): δ 10.55 (s, 1H), 9.63 (s, 1H), 7.75 (d, J=8.4 Hz, 2H), 7.60 (dd, J=4.6, 8.7 Hz, 2H), 7.37 (s, 1H), 7.27 (t, J=8.7 Hz, 2H), 6.88 (d, J=8.4 Hz, 2H).

MS (ES+) m/z 327 (M+H)$^+$ (MW: 326.35).

Example 19

N-{4-[2-(4-Fluoro-phenylamino)-imidazo[2,1-b][1,3,4]thiadiazol-5-yl]-phenyl}-acetamide (4-Fluoro-phenyl)-(5-iodo-imidazo[2,1-b][1,3,4]thiadiazol-2-yl)-amine (0.065 g, 0.18 mmol) was suspended in 1,4-dioxane (1 mL) at room temperature, and Argon was bubbled into the mixture while dichlorobis(triphenylphosphine)-palladium(II) (13 mg, 0.018 mmol), 4-acetamidophenylboronic acid (37 mg, 0.21 mmol), cesium carbonate (118 mg, 0.36 mmol) and water (1 mL) were added. The mixture was deoxygenated for 10 minutes and heated under microwave irradiation at 140° C. for 30 minutes. On cooling, the mixture was diluted with dichloromethane (5 mL), adsorbed in silica and purified by column chromatography (Biotage™/Flash, silica, methanol:dichloromethane 0.4:9.6 to 1.5:8.5). The product obtained was treated with diethylether (7 mL) and filtered to give N-{4-[2-(4-fluoro-phenylamino)-imidazo[2,1-b][1,3,4]thiadiazol-5-yl]-phenyl}-acetamide as an off-white solid (10 mg, 15% yield).

$^1$H-NMR (300 MHz, DMSO-$d_6$): δ 10.58 (s, 1H), 10.04 (s, 1H), 7.87 (d, J=8.5 Hz, 2H), 7.69 (d, J=8.7 Hz, 2H), 7.61 (dd, J=4.7, 8.7 Hz, 2H), 7.49 (s, 1H), 7.28 (t, J=8.8 Hz, 2H), 2.07 (s, 3H).

MS (ES+) m/z 368 (M+H)$^+$ (MW: 367.41).

Intermediate 23

Imidazo[2,1-b][1,3,4]thiadiazol-2-yl-(4-methoxyphenyl)amine

A mixture of 2-bromo-imidazo[2,1-b][1,3,4]thiadiazole (1.0 g, 4.90 mmol) and p-anisidine (19.6 mmol, 2.41 g) in trifluoroethanol (12 mL) was heated under microwave irradiation at 170° C. for 1 hour. On cooling, the mixture was diluted with dichloromethane (10 mL) and purified by column chromatography (Biotage™/Flash, silica, methanol:dichloromethane 0.2:9.8 to 1:9). The residue obtained was triturated with diethylether and few drops of methanol to give imidazo[2,1-b][1,3,4]thiadiazol-2-yl-(4-methoxyphenyl)amine as a white solid (355 mg, 29% yield).

$^1$H-NMR (300 MHz, CDCl$_3$): δ 8.01 (s, 1H), 7.55 (s, 1H), 7.44 (d, J=8.9, 2H), 7.22 (s, 1H), 6.90 (d, J=8.8, 2H), 3.80 (s, 3H).

MS (ES+) m/z 247 (M+H)$^+$ (MW: 246.29).

Intermediate 24

(5-Iodo-imidazo[2,1-b][1,3,4]thiadiazol-2-yl)-(4-methoxyphenyl)amine

Imidazo[2,1-b][1,3,4]thiadiazol-2-yl-(4-methoxyphenyl)amine (0.455 g, 1.85 mmol) was dissolved in N,N-dimethylformamide (8 mL) and N-iodosuccinimide (2.03 mmol, 0.48 g) was added in one portion. The reaction mixture was stirred at room temperature for 22 hours in the absence of light. Solvent was evaporated and the residue was purified by column chromatography (Biotage™/Flash, silica, ethylacetate:dichloromethane 2:8 to 0:10) to give 0.11 g of (5-iodo-imidazo[2,1-b][1,3,4]thiadiazol-2-yl)-(4-methoxyphenyl)amine as an off-white solid (16% yield).

$^1$H-NMR (300 MHz, DMSO-$d_6$): δ 10.30 (s, 1H), 7.59 (d, J=9.0 Hz, 2H), 7.06 (s, 1H), 6.93 (d, J=9.0 Hz, 2H), 3.68 (s, 3H).

MS (ES+) m/z 373 (M+H)$^+$ (MW: 372.19).

Example 20

{5-[3-Dimethylamino-phenyl)-imidazo[2,1-b][1,3,4]thiadiazol-2-yl]}-(4-methoxyphenyl)amine (5-Iodo-imidazo[2,1-b][1,3,4]thiadiazol-2-yl)-(4-methoxyphenyl)amine (55 mg, 0.10 mmol) was suspended in 1,4-dioxane (1 mL) at room temperature and argon was bubbled into the mixture while tetrakis(triphenylphosphine)palladium(0) (0.011 mmol, 12 mg), 3-(N,N-dimethylamino)phenylboronic acid (0.202 mmol, 33 mg), cesium carbonate (0.268 mmol, 88 mg) and water (1 mL) were added. The mixture was deoxygenated for 10 minutes and heated under microwave irradiation at 140° C. for 1 hour. On cooling, the mixture was diluted with dichloromethane, adsorbed in silica and purified by column chromatography (Biotage™/Flash, silica, methanol:dichloromethane 0.2:9.8 to 2:8). The obtained residue was further purified by preparative HPLC to give {5-[3-dimethylaminophenyl)-imidazo[2,1-b][1,3,4]thiadiazol-2-yl]}-(4-methoxyphenyl)-amine as a white solid (4 mg, 7% yield).

$^1$H-NMR (300 MHz, DMSO-$d_6$): δ 8.43 (br s, 1H), 7.60-7.54 (m, 2H), 7.54-7.52 (s, 1H), 7.52-7.49 (m, 1H), 7.25 (t, J=7.9, 1H), 7.14 (d, J=7.8, 1H), 6.94 (d, J=9.0, 2H), 6.67 (dd, J=2.2, 8.0, 1H), 3.75 (s, 3H), 2.99 (s, 6H).

MS (ES+) m/z 366 (M+H)$^+$ (MW: 365.46).

Intermediate 25

2-Bromo-7,7a-dihydro-imidazo[2,1-b][1,3,4]thiadiazole-5-carbaldehyde

3-Bromo-imidazothiazole (1 g, 4.9 mmol) was added over a mixture of dimethylformamide (10 mL) and phosphorus oxychloride (1.5 mL, 16.1 mmol) (Vilsmeier-Haack reagent) at 0° C. The mixture was stirred at 0° C. for 30 minutes, at room temperature for 2 hours and at 60° C. for additional 2 hours. The reaction mixture turned dark red-brown and was poured in aqueous solution of sodium carbonate. The resulted mixture was stirred at 90° C. for 2 hours. The reaction mixture was cooled to room temperature, diluted with water (30 mL) and extracted with chloroform (3×40 mL). The combined organic layers were washed with water (3×40 mL), dried over anhydrous sodium sulphate and concentrated. The crude was purified by column chromatography (Biotage/flash, silica, methanol:dichloromethane 0:10 to 0.7:9.3), yielding a fraction containing the title compound and a byproduct. Both compounds were separated employing flash column chromatography (Isolute II-5 g, methanol:dichloromethane, 0:10 to 0.6:9.4), giving 2-bromo-7,7a-dihydro-imidazo[2,1-b][1,3,4]thiadiazole-5-carbaldehyde as a pale-brown solid (0.085 g, 7.5% yield).

$^1$H NMR (300 MHz, CDCl$_3$): δ 9.86 (s, 1H), 7.98 (s, 1H)
MS (APCI+) m/z 233.9, 231.9 (M+H)$^+$ (MW: 232.06).

General Procedure F for the Preparation of Intermediates 26-29

2-Bromo-7,7a-dihydro-imidazo[2,1-b][1,3,4]thiadiazole-5-carbaldehyde (1 eq) and appropriate amine (1.1 eq) (e.g. 4-amino-phenyl-ethanone) were mixed in dichloroethane (14 mL/mmol) and treated with sodium triacetoxyborohydride (1.4 eq) and acetic acid (1 eq). The mixture was stirred at room temperature under inert atmosphere (N$_2$) for 3 hours. The reaction mixture was quenched with 2M aqueous potassium hydroxide and extracted with ethyl acetate. The combined organic layers were washed with brine, dried over anhydrous sodium sulphate and concentrated, yielding the required product without additional purification needed (e.g. 1-{4-[(2-bromo-imidazo[2,1-b][1,3,4]thiadiazol-5-ylmethyl)-amino]-phenyl}-ethanone).

Intermediate 26

1-{4-[(2-Bromo-imidazo[2,1-b][1,3,4]thiadiazol-5-ylmethyl)-amino]-phenyl}-ethanone The title compound was obtained in 90% yield.
$^1$H NMR (300 MHz, CDCl$_3$): δ 7.22-7.06 (m, 4H), 6.81 (d, J=8.1, 1H), 4.56 (s, 2H), 3.91 (s br, 1H), 2.48 (m, 3H).
MS (ES+) m/z 352.9, 351.9 (M+H)$^+$ (MW: 351.23).

Intermediate 27

(2-Bromo-imidazo[2,1-b][1,3,4]thiadiazol-5-ylmethyl)-(3,4-dimethoxy-phenyl)-amine The title compound was obtained in 75% yield.
MS (ES+) m/z 369.0, 371.0 (M+H)$^+$ (MW: 369.24).

Intermediate 28

(2-Bromo-imidazo[2,1-b][1,3,4]thiadiazol-5-ylmethyl)-(3-chloro-4-fluoro-phenyl)-amine The title compound was obtained in 51% yield.
MS (ES+) m/z 360.0, 362.0 (M+H)$^+$ (MW: 361.62)

Intermediate 29

2-Dimethylamino-7,7a-dihydro-imidazo[2,1-b][1,3,4]thiadiazole-5-carbaldehyde

The title compound was isolated as a by-product in the preparation of 2-bromo-7,7a-dihydro-imidazo[2,1-b][1,3,4]thiadiazole-5-carbaldehyde. The required product was obtained as a dark cream solid (35 mg, 3.6% yield).

$^1$H NMR (300 MHz, CDCl$_3$): δ 9.76 (s, 1H), 7.75 (s, 1H), 3.11 (s, 3H), 3.08 (s, 3H)
MS (APCI+) m/z 197.0 (M+H)$^+$ (MW: 196.23).

General Procedure G for the Preparation of Examples 21-26.

A mixture of the appropriate bromide (e.g. (2-bromo-imidazo[2,1-b][1,3,4]thiadiazol-5-ylmethyl)-(3-chloro-4-fluoro-phenyl)-amine) (1 eq) and the adequate amine (e.g. isobutylamine) (4 eq) in 1,4-dioxane (about 25 mL/mmol) was heated at 145° C. by microwave irradiation for several hours (from 2 to 4 hours depending upon the corresponding amine). The reaction mixture was diluted with dichloromethane, washed with water (×2), brine, dried over anhydrous sodium sulphate and concentrated. The residue was purified by column chromatography on flash silica gel to give the desired product (e.g. {5-[(3-Chloro-4-fluoro-phenylamino)-methyl]-7,7a-dihydro-imidazo[2,1-b][1,3,4]thiadiazol-2-yl}-isobutyl-amine).

Example 21

1-{3-[(2-Dimethylamino-7,7a-dihydro-imidazo[2,1-b][1,3,4]thiadiazol-5-ylmethyl)-amino]phenyl}-ethanone The title compound was obtained in 30% yield after purification by column chromatography on flash silica gel (methanol:dichloromethane, 0:10 to 0.7:9.3).
$^1$H NMR (300 MHz, CDCl$_3$): δ 7.35-7.07 (m, 3H), 6.96 (s, 1H), 6.91-6.70 (m, 1H), 4.46 (s, 2H), 3.06 (s, 6H), 2.49 (s, 3H).
MS (ES+) m/z 316.1 (M+H)$^+$ (MW: 315.40).

Example 22

1-{3-[(2-Isobutylamino-7,7a-dihydro-imidazo[2,1-b][1,3,4]thiadiazol-5-ylmethyl)-amino]phenyl}-ethanone The title compound was obtained in 34% yield after purification by column chromatography on flash silica gel (methanol:dichloromethane, 0:10 to 0.5:9.5).
$^1$H NMR (300 MHz, CDCl$_3$): δ 7.36-7.08 (m, 3H), 6.88-6.73 (m, 1H), 6.29 (s, 1H), 4.44 (s, 2H), 3.11 (d, J=6.3 Hz, 2H), 2.51 (m, 3H), 1.89 (dt, J=6.7 Hz, 13.4 Hz, 1H), 0.92 (d, J=6.7 Hz, 6H).
MS (ES+) m/z 344.1 (M+H)$^+$ (MW: 343.45).

Example 23

1-(3-{[2-(2-Methoxy-ethylamino)-7,7a-dihydro-imidazo[2,1-b][1,3,4]thiadiazol-5-ylmethyl]-amino}-phenyl)-ethanone The title compound was obtained in 34% yield after purification by column chromatography on flash silica gel (methanol:dichloromethane, 0:10 to 0.5:9.5).
$^1$H NMR (300 MHz, CDCl$_3$): δ 7.42-7.01 (m, 3H), 6.81 (d, J=7.9 Hz, 1H), 6.30 (s, 1H), 4.44 (s, 2H), 3.63-3.40 (m, 4H), 3.40-3.18 (m, 3H), 2.57-2.32 (m, 3H).
MS (ES+) m/z 346.1 (M+H)$^+$ (MW: 345.43).

Example 24

{5-[(3,4-Dimethoxy-phenylamino)-methyl]-7,7a-dihydro-imidazo[2,1b][1,3,4]thiadiazol-2-yl}-(2-methoxy-ethyl)-amine The title compound was obtained in 34% yield after purification by column chromatography on flash silica gel (methanol:dichloromethane, 0:10 to 0.5:9.5).
$^1$H NMR (300 MHz, CDCl$_3$): δ 6.95 (s, 1H), 6.68 (d, J=8.5 Hz, 1H), 6.34-6.10 (m, 2H), 5.75 (s, 1H), 4.37 (s, 2H), 3.75 (d, J=9.2 Hz, 6H), 3.64-3.43 (m, 4H), 3.33 (s, 3H), 2.99-2.70 (m, 2H).
MS (ES+) m/z 364.1 (M+H)$^+$ (MW: 363.44).

Example 25

{5-[(3,4-Dimethoxy-phenylamino)-methyl]-7,7a-dihydro-imidazo[2,1-b][1,3,4]thiadiazol-2-yl}-(tetrahydro-pyran-4-yl)-amine The title compound was obtained in 26% yield after purification by column chromatography on flash silica gel (methanol:dichloromethane, 0:10 to 0.5:9.5).
$^1$H NMR (300 MHz, CDCl$_3$): δ 6.95 (s, 1H), 6.68 (d, J=8.5 Hz, 1H), 6.33-6.06 (m, 3H), 4.38 (s, 2H), 3.95 (m, 2H), 3.81-3.61 (m, 6H), 3.46 (m, 2H), 2.35 (1H, m), 2.04 (m, 2H), 1.59 (m, 2H).
MS (ES+) m/z 390.1 (M+H)$^+$ (MW: 389.48).

Example 26

{5-[(3-Chloro-4-fluoro-phenylamino)-methyl]-7,7a-dihydro-imidazo[2,1-b][1,3,4]thiadiazol-2-yl}-isobutyl-amine The title compound was obtained in 26% yield after purification by column chromatography on flash silica gel (methanol:dichloromethane, 0:10 to 0.5:9.5).
$^1$H NMR (300 MHz, CDCl$_3$): δ 6.89 (s, 1H), 6.65 (m, 1H), 6.52-6.32 (m, 1H), 4.35 (s, 2H), 3.22-3.05 (m, 2H), 1.90 (dt, J=6.7 Hz, 13.4 Hz, 1H), 0.94 (s, 6H).
MS (ES+) m/z 354.1 (M+H)$^+$ (MW: 353.85).

Intermediate 30

2-Bromo-imidazo[2,1-b][1,3,4]thiadiazole-5-sulfonic acid

The starting 2-bromo-imidazo[2,1-b][1,3,4]thiadiazole (2.0 g; 9.9 mmol) was dissolved in oleum (4.0 mL) and the resulting solution was heated at 80° C. for 8 hours. The reaction was allowed to cool to room temperature and then poured onto crushed ice. One spoon of sodium chloride was added and the resulting precipitate was isolated by vacuum filtration and washed with cold water. It was dried by azeotrope distillation with toluene. The title compound 2-bromo-imidazo[2,1-b][1,3,4]thiadiazole-5-sulfonic acid was isolated as a beige solid, (2.33 g; 83% yield).
$^1$H NMR (300 MHz, DMSO-d$_6$): δ 7.30 (1H, s).
MS (ES+) m/z 283.9 (M+H)$^+$ (MW: 218.08).

Intermediate 31

2-Bromo-imidazo[2,1-b][1,3,4]thiadiazole-5-sulfonyl chloride

2-Bromo-imidazo[2,1-b][1,3,4]thiadiazole-5-sulfonic acid (1.1 g; 3.87 mmol) was reacted with phosphorus oxychloride (2.53 mL; 27.1 mmol) and phosphorus pentachloride (0.56 g; 2.7 mmol) in anhydrous 1,2-dichloroethane (4 mL) at 90° C. for 5 hours. The reaction mixture was allowed to cool and a mixture (1:1) of dichloromethane and ether was added. A brown oil was separated. The supernatant was decanted and the oil washed with ether and the crude product used immediately. 0.85 g was isolated.

General Procedure H for the Preparation of Intermediates 32-34

2-Bromo-imidazo[2,1-b][1,3,4]thiadiazole-5-sulfonyl chloride (1 eq) was dissolved in acetonitrile (6 mL/mmol) and triethylamine (1 eq) was added to the solution. The resulting mixture was cooled in an ice bath and the appropriate amine (e.g. morpholine) (2.5 eq) was added. The reaction was stirred for 30 minutes at 0° C., then at room temperature for 2 hours. The solvent was evaporated and the crude product was taken up in dichloromethane and sodium hydrogen carbonate-solution. Extraction with dichloromethane, drying with sodium sulphate and evaporation gave the crude material that was washed with ether:hexane (1:3) to give the desired sulphonamide (e.g. 2-bromo-5-(morpholine-4-sulfonyl)-imidazo[2,1-b][1,3,4]thiadiazole) of good purity.

Intermediate 32

2-Bromo-5-(morpholine-4-sulfonyl)-imidazo[2,1-b][1,3,4]thiadiazole

The title compound was isolated in 29% yield.
$^1$H NMR (300 MHz, DMSO-d$_6$): δ 7.84 (1H, s), 3.58 (4H, m), 3.04 (4H, m).

Intermediate 33

2-Bromo-imidazo[2,1-b][1,3,4]thiadiazole-5-sulfonic acid ethylamide

The title compound was isolated in 35% yield.
$^1$H NMR (300 MHz, DMSO-d$_6$): δ 7.77 (1H, s), 5.21 (1H, m), 3.07 (2H, m), 1.10 (3H, t, J=7.3 Hz).

Intermediate 34

2-Bromo-imidazo[2,1-b][1,3,4]thiadiazole-5-sulfonic acid phenylamide

The title compound was isolated in 59% yield.
MS (ES+) m/z 360.90 (M+H)$^+$ (MW: 359.22).

General Procedure I for the Preparation of Example 27-29

The appropriate 2-bromo-imidazo[2,1-b][1,3,4]thiadiazole sulphonamide (e.g. 2-bromo-imidazo[2,1-b][1,3,4]thiadiazole-5-sulfonic acid phenylamide) (1 eq) was added to 4-fluorobenzyl amine (10 eq) and the mixture was heated in a microwave reactor at 200 W for 20 minutes at 135° C. The reaction mixture was taken up in sodium bicarbonate and dichloromethane and extracted. The solvent was evaporated and the residue was purified on silica gel (ethyl acetate) to give the desired product (e.g. 2-(4-fluoro-benzylamino)-imidazo[2,1-b][1,3,4]thia-diazole-5-sulfonic acid phenylamide).

Example 27

2-(4-Fluoro-benzylamino)-imidazo[2,1-b][1,3,4]thiadiazole-5-sulfonic acid phenylamide The title compound was isolated in 10% yield.
$^1$H NMR (300 MHz, DMSO-d$_6$): δ 9.17 (1H, s), 7.61 (1H, s), 7.41 (2H, dd, J=5.6, 8.5 Hz), 7.37 (1H, s), 7.11 (4H, m), 7.01 (2H, t, J=8.8 Hz), 6.92 (1H, ddd, J=2.8, 5.8, 8.4 Hz), 4.55 (2H, d, J=5.7 Hz).
MS (ES+) m/z 404.0 (M+H)+ (MW: 403.46).

Example 28

(4-Fluoro-benzyl)-[5-(morpholine-4-sulfonyl)-imidazo[2,1-b][1,3,4]thiadiazol-2-yl]-amine The title compound was isolated in 13% yield.
$^1$H NMR (300 MHz, DMSO-d$_6$): δ 7.73 (1H, s), 7.37 (3H, m), 7.00 (2H, t, J=8.8 Hz), 4.51 (2H, d, J=5.7 Hz), 3.49 (4H, m), 2.97 (4H, m).
MS (ES+) m/z 398.05 (M+H)+ (MW: 397.45).

Example 29

2-(4-Fluoro-benzylamino)-imidazo[2,1-b][1,3,4] thiadiazole-5-sulfonic acid ethylamide The title compound was isolated in 9% yield.
$^1$H NMR (300 MHz, DMSO-d$_6$): δ 7.65 (1H, s), 7.37 (3H, m), 6.99 (2H, t, J=8.8 Hz), 6.46 (1H, t, J=5.5 Hz), 4.51 (2H, d, J=5.7 Hz), 2.93 (2H, m), 0.91 (3H, t, J=7.2 Hz).
MS (ES+) m/z 356.12 (M+H)+ (MW: 355.42).

General Procedure J for the Preparation of Example 30-33

The appropriate 2-bromo-imidazo[2,1-b][1,3,4]thiadiazole sulphonamide (e.g. 2-bromo-imidazo[2,1-b][1,3,4]thiadiazole-5-sulfonic acid phenylamide) (1 eq) was dissolved in anhydrous acetonitrile (6 mL/mmol) and reacted at room temperature for 16 hours with an aliphatic amine (e.g. cyclopropanemethylamine) (2.5 eq) in the presence of triethylamine (1 eq). The solvent was removed in vacuo and the reaction mixture was taken up in sodium bicarbonate and dichloromethane and extracted. Drying over sodium sulphate and evaporation of the solvent gave the product (e.g. 2-(cyclopropylmethyl-amino)-imidazo[2,1-b][1,3,4]thiadiazole-5-sulfonic acid phenylamide) that was further purified by washing with ether:hexane (1:3).

Example 30

2-(Cyclopropylmethyl-amino)-imidazo[2,1-b][1,3,4] thiadiazole-5-sulfonic acid phenylamide The title compound was isolated in 22% yield.
$^1$H NMR (300 MHz, DMSO-d$_6$): δ 9.09 (1H, s), 7.39 (1H, m), 7.14 (3H, m), 6.92 (1H, t, J=8.8 Hz), 3.46 (1H, s), 3.19 (2H, m), 1.07 (1H, m), 0.46 (2H, m). 0.20 (2H, m).
MS (ES+) m/z 350.1 (M+H)+ (MW: 349.44).

Example 31

2-Isobutylamino-imidazo[2,1-b][1,3,4]thiadiazole-5-sulfonic acid phenyl-amide

The title compound was isolated in 14% yield.
$^1$H NMR (300 MHz, DMSO-d$_6$): δ 9.18 (1H, s), 7.36 (1H, s), 7.15 (5H, m), 6.92 (1H, t, J=6.9 Hz), 3.17 (2H, t, J=6.2 Hz), 1.92 (1H, m), 0.87 (6H, d, J=6.7 Hz).
MS (ES+) m/z 352.1 (M+H)+ (MW: 351.45).

Example 32

Cyclopropylmethyl-[5-(morpholine-4-sulfonyl)-imidazo[2,1-b][1,3,4]thiadiazol-2-yl]-amine The title compound was isolated in 66% yield.
$^1$H NMR (300 MHz, DMSO-d$_6$): δ 7.34 (1H, s), 3.55 (4H, m), 3.18 (2H, dd, J=5.3, 6.8 Hz), 3.08 (4H, m), 6.92 (1H, t, J=6.9 Hz), 1.06 (1H, m), 0.42 (2H, m), 0.20 (2H, m).
MS (ES+) m/z 344.1 (M+H)+ (MW: 343.43).

Example 33

2-Ethylamino-imidazo[2,1-b][1,3,4]thiadiazole-5-sulfonic acid ethylamide

2-Bromo-imidazo[2,1-b][1,3,4]thiadiazole-5-sulfonyl chloride (0.15 g; 0.50 mmol) was dissolved in dry acetonitrile (5 mL). Triethylamine (69 µL; 0.50 mmol) was added, and the reaction mixture was cooled at 0° C. for 10 minutes before adding ethylamine (2M in tetrahydrofuran, 2.5 mL; 5.0 mmol). The reaction was allowed to reach room temperature and stirred overnight. The solvent was evaporated and the crude taken up in dichloromethane and sodium hydrogen carbonate solution. Extraction with dichloromethane, drying over sodium sulphate and evaporation of the solvent gave a brown gum that was purified on silica gel (ethyl acetate: hexane 4:1). The title product 2-ethylamino-imidazo[2,1-b][1,3,4]thiadiazole-5-sulfonic acid ethylamide was isolated as a white powder (43 mg, 31%).
$^1$H NMR (300 MHz, DMSO-d$_6$): δ 7.29 (1H, s), 7.14 (1H, s), 6.50 (1H, s), 3.34 (2H, m), 2.98 (2H, m), 1.16 (3H, t, J=7.2 Hz), 0.97 (3H, t, J=7.2 Hz).
MS (ES+) m/z 276.0 (M+H)+ (MW: 275.35).

Example 34

The following compounds were either made according to the procedures described herein, or, were acquired from publicly-available sources:

(1) 1-[3-(2-Isobutylamino-imidazo[2,1-b][1,3,4]thiadiazol-5-yl)-phenyl]-ethanone;
(2) 1-[3-(2-Cyclohexylamino-imidazo[2,1-b][1,3,4]thiadiazol-5-yl)-phenyl]ethan-one;
(3) [5-(3-Dimethylamino-phenyl)-imidazo[2,1-b][1,3,4]thiadiazol-2-yl]-isobutyl-amine;
(4) (5-Naphthalen-2-yl-imidazo[2,1-b][1,3,4]thiadiazol-2-yl)-(2-phenoxy-ethyl)-amine;
(5) [5-(3-Chloro-phenyl)-imidazo[2,1-b][1,3,4]thiadiazol-2-yl]-(2-pyridin-2-yl-ethyl)-amine;
(6) [5-(4-Chloro-phenyl)-imidazo[2,1-b][1,3,4]thiadiazol-2-yl]-(2-pyridin-2-yl-ethyl)-amine;
(7) N-{3-[2-(Cyclopropylmethyl-amino)-imidazo[2,1-b][1,3,4]thiadiazol-5-yl]-phenyl}-acetamide;
(8) (2-Methoxy-ethyl)-(5-naphthalen-2-yl-imidazo[2,1-b][1,3,4]thiadiazol-2-yl)-amine;
(9) (2-Pyridin-2-yl-ethyl)[5-(3-trifluoromethoxy-phenyl)-imidazo[2,1-b][1,3,4]thiadiazol-2-yl]-amine;
(10) Cyclopropylmethyl-(5-naphthalen-2-yl-imidazo[2,1-b][1,3,4]thiadiazol-2-yl)-amine;
(11) (5-Naphthalen-2-yl-imidazo[2,1-b][1,3,4]thiadiazol-2-yl)-(tetrahydro-pyran-4-ylmethyl)-amine;
(12) (4-Methoxy-benzyl)-(5-naphthalen-2-yl-imidazo[2,1-b][1,3,4]thiadiazol-2-yl)-amine;
(13) [5-(3-Chloro-4-fluoro-phenyl)-imidazo[2,1-b][1,3,4]thiadiazol-2-yl]-isobutyl-amine;
(14) [5-(3-Chloro-4-fluoro-phenyl)-imidazo[2,1-b][1,3,4]thiadiazol-2-yl]-(2-meth-oxyethyl)-amine;
(15) (2-Pyridin-2-yl-ethyl)[5-(3-trifluoromethyl-phenyl)-imidazo[2,1-b][1,3,4]thia-diazol-2-yl]-amine;
(16) [5-(3-Dimethylamino-phenyl)-imidazo[2,1-b][1,3,4]thiadiazol-2-yl]-(tetrahydro-pyran-4-ylmethyl)-amine;

(17) N-(3-{2-[(Furan-2-ylmethyl)-amino]-imidazo[2,1-b][1,3,4]thiadiazol-5-yl}-phenyl)-acetamide;
(18) Cyclopropylmethyl-[5-(3-trifluoromethyl-phenyl)-imidazo[2,1-b][1,3,4]thia-diazol-2-yl]-amine;
(19) [5-(3-Dimethylamino-phenyl)-imidazo[2,1-b][1,3,4]thiadiazol-2-yl]-(2-methoxy-ethyl)-amine;
(20) (Tetrahydro-pyran-4-ylmethyl)[5-(3-trifluoromethoxy-phenyl)-imidazo[2,1-b]-[1,3,4]thiadiazol-2-yl]-amine;
(21) 1-(3-{2-[(Tetrahydro-pyran-4-ylmethyl)-amino]-imidazo[2,1-b][1,3,4]thiadiazol-5-yl}-phenyl)-ethanone;
(22) 1-(3-{2-[(Thiophen-2-ylmethyl)-amino]-imidazo[2,1-b][1,3,4]thiadiazol-5-yl}-phenyl)-ethanone;
(23) [5-(3-Chloro-phenyl)-imidazo[2,1-b][1,3,4]thiadiazol-2-yl]-(tetrahydro-pyran-4-ylmethyl)-amine;
(24) 4-(2-Cyclohexylamino-imidazo[2,1-b][1,3,4]thiadiazol-5-yl)-phenol;
(25) 4-[2-(Cyclopropylmethyl-amino)-imidazo[2,1-b][1,3,4]thiadiazol-5-yl]-2-methoxy-phenol;
(26) N-(3-{2-[(Thiophen-2-ylmethyl)-amino]-imidazo[2,1-b][1,3,4]thiadiazol-5-yl}-phenyl)-acetamide;
(27) [5-(3-Chloro-phenyl)-imidazo[2,1-b][1,3,4]thiadiazol-2-yl]-(2-methoxy-ethyl)-amine;
(28) N-{3-[2-(2-Pyridin-2-yl-ethylamino)-imidazo[2,1-b][1,3,4]thiadiazol-5-yl]-phenyl}-acetamide;
(29) [5-(4-Chloro-phenyl)-imidazo[2,1-b][1,3,4]thiadiazol-2-yl]-(tetrahydro-pyran-4-ylmethyl)-amine;
(30) Isobutyl-[5-(3-trifluoromethoxy-phenyl)-imidazo[2,1-b][1,3,4]thiadiazol-2-yl]-amine;
(31) [5-(4-Chloro-phenyl)-imidazo[2,1-b][1,3,4]thiadiazol-2-yl]-(2-methoxy-ethyl)-amine;
(32) Isobutyl-(5-naphthalen-2-yl-imidazo[2,1-b][1,3,4]thiadiazol-2-yl)-amine;
(33) [5-(3-Chloro-4-fluoro-phenyl)-imidazo[2,1-b][1,3,4]thiadiazol-2-yl]-(4-meth-oxybenzyl)-amine;
(34) [5-(3-Dimethylamino-phenyl)-imidazo[2,1-b][1,3,4]thiadiazol-2-yl]-(2-methyl-benzyl)-amine;
(35) Isobutyl-[5-(6-methoxy-pyridin-3-yl)-imidazo[2,1-b][1,3,4]thiadiazol-2-yl]-amine;
(36) Benzyl-(5-pyridin-4-yl-imidazo[2,1-b][1,3,4]thiadiazol-2-yl)-amine;
(37) (4-Fluoro-benzyl)[5-(6-methoxy-pyridin-3-yl)-imidazo[2,1-b][1,3,4]thiadiazol-2-yl]-amine;
(38) [5-(3-Dimethylamino-phenyl)-imidazo[2,1-b][1,3,4]thiadiazol-2-yl]-(4-fluoro-benzyl)-amine;
(39) Cyclopropylmethyl-[5-(3-trifluoromethoxy-phenyl)-imidazo[2,1-b][1,3,4]thia-diazol-2-yl]-amine;
(40) 4-{2-[(Furan-2-ylmethyl)-amino]-imidazo[2,1-b][1,3,4]thiadiazol-5-yl}-phenol;
(41) N-{3-[2-(4-Fluoro-benzylamino)-imidazo[2,1-b][1,3,4]thiadiazol-5-yl]-phenyl}-acetamide;
(42) 4-{2[(Furan-2-ylmethyl)-amino]-imidazo[2,1-b][1,3,4]thiadiazol-5-yl}-2-methoxy-phenol;
(43) Benzyl-[5-(3-dimethylamino-phenyl)-imidazo[2,1-b][1,3,4]thiadiazol-2-yl]-amine;
(44) 1-{3-[2-(2-Methoxy-ethylamino)-imidazo[2,1-b][1,3,4]thiadiazol-5-yl]-phenyl}-ethanone;
(45) (4-Fluoro-benzyl)-(5-pyridin-4-yl-imidazo[2,1-b][1,3,4]thiadiazol-2-yl)-amine;
(46) (2-Methoxy-ethyl)-[5-(3-trifluoromethoxy-phenyl)-imidazo[2,1-b][1,3,4]thia-diazol-2-yl]-amine;
(47) Cyclohexyl-[5-(5-methoxy-pyridin-3-yl)-imidazo[2,1-b][1,3,4]thiadiazol-2-yl]-amine;
(48) (2-Pyridin-2-yl-ethyl)-(5-thiophen-3-yl-imidazo[2,1-b][1,3,4]thiadiazol-2-yl]-amine;
(49) 4-[2-(Cyclopropylmethyl-amino)-imidazo[2,1-b][1,3,4]thiadiazol-5-yl]-phenol;
(50) N-{3-[2-(2-Methoxy-ethylamino)-imidazo[2,1-b][1,3,4]thiadiazol-5-yl]-phenyl}-acetamide;
(51) 2-Methoxy-4-[2-(2-methoxy-ethylamino)-imidazo[2,1-b][1,3,4]thiadiazol-5-yl]-phenol;
(52) 4-[2-(2-Methoxy-ethylamino)-imidazo[2,1-b][1,3,4]thiadiazol-5-yl]-benzonitrile;
(53) [5-(3-Chloro-phenyl)-imidazo[2,1-b][1,3,4]thiadiazol-2-yl]-cyclopropylmethyl-amine;
(54) Cyclopropylmethyl-[5-(6-methoxy-pyridin-3-yl)-imidazo[2,1-b][1,3,4]thiadiazol-2-yl]-amine;
(55) Isobutyl-(5-thiophen-3-yl-imidazo[2,1-b][1,3,4]thiadiazol-2-yl)-amine;
(56) [5-(4-Chloro-phenyl)-imidazo[2,1-b][1,3,4]thiadiazol-2-yl]-isobutyl-amine;
(57) (4-Fluoro-benzyl)-(5-pyridin-3-yl-imidazo[2,1-b][1,3,4]thiadiazol-2-yl)-amine;
(58) 4-[2-(Cyclopropylmethyl-amino)-imidazo[2,1-b][1,3,4]thiadiazol-5-yl]-2,6-dimethylphenol;
(59) Cyclopropylmethyl-(5-thiophen-3-yl-imidazo[2,1-b][1,3,4]thiadiazol-2-yl)-amine;
(60) (2-Methoxy-ethyl)-(5-thiophen-2-yl-imidazo[2,1-b][1,3,4]thiadiazol-2-yl)-amine;
(61) 3-(2-Isobutylamino-imidazo[2,1-b][1,3,4]thiadiazol-5-yl)-N,N-dimethyl-benz-amide;
(62) Benzo[1,3]dioxol-5-ylmethyl-[5-(3-chloro-4-fluoro-phenyl)-imidazo[2,1-b][1,3,4]-thiadiazol-2-yl]-amine;
(63) Isobutyl-[5-(5-methoxy-pyridin-3-yl)-imidazo[2,1-b][1,3,4]thiadiazol-2-yl]-amine;
(64) [5-(3-Fluoro-phenyl)-imidazo[2,1-b][1,3,4]thiadiazol-2-yl]-(2-methoxy-ethyl)-amine;
(65) 1-{3-[2-(2-Morpholin-4-yl-ethylamino)-imidazo[2,1-b][1,3,4]thiadiazol-5-yl]-phenyl}-ethanone;
(66) (5-Phenyl-imidazo[2,1-b][1,3,4]thiadiazol-2-yl)-(2-pyridin-2-yl-ethyl)-amine;
(67) (Tetrahydro-pyran-4-ylmethyl)-(5-thiophen-3-yl-imidazo[2,1-b][1,3,4]thiadiazol-2-yl)-amine;
(68) [5-(6-Methoxy-pyridin-3-yl)-imidazo[2,1-b][1,3,4]thiadiazol-2-yl]-(tetrahydro-pyran-4-ylmethyl)-amine;
(69) [5-(5-Methoxy-pyridin-3-yl)-imidazo[2,1-b][1,3,4]thiadiazol-2-yl]-(tetrahydro-pyran-4-ylmethyl)-amine;
(70) Isobutyl-(5-pyridin-4-yl-imidazo[2,1-b][1,3,4]thiadiazol-2-yl)-amine;
(71) Cyclopropylmethyl-[5-(3,4-dimethoxy-phenyl)-imidazo[2,1-b][1,3,4]thiadiazol-2-yl]-amine;
(72) 3-[2-(Cyclopropylmethyl-amino)-imidazo[2,1-b][1,3,4]thiadiazol-5-yl]-N-(2-dimethylamino-ethyl)-benza-mide;
(73) [5-(3-Fluoro-phenyl)-imidazo[2,1-b][1,3,4]thiadiazol-2-yl]-(tetrahydro-pyran-4-ylmethyl)-amine;
(74) Furan-2-ylmethyl-(5-thiophen-3-yl-imidazo[2,1-b][1,3,4]thiadiazol-2-yl)-amine;
(75) Cyclopropylmethyl-[5-(5-methoxy-pyridin-3-yl)-imidazo[2,1-b][1,3,4]thiadiazol-2-yl]-amine;
(76) (2-Methoxy-ethyl)[5-(6-methoxy-pyridin-3-yl)-imidazo[2,1-b][1,3,4]thiadiazol-2-yl]-amine;
(77) [5-(2-Chloro-phenyl)-imidazo[2,1-b][1,3,4]thiadiazol-2-yl]-(tetrahydro-pyran-4-ylmethyl)-amine;
(78) (5-Phenyl-imidazo[2,1-b][1,3,4]thiadiazol-2-yl)-(tetrahydro-pyran-4-ylmethyl)-amine;
(79) Cyclopropylmethyl-[5-(1-methyl-1H-pyrazol-4-yl)-imidazo[2,1-b][1,3,4]thia-diazol-2-yl]-amine;
(80) 3-[2-(Cyclopropylmethyl-amino)-imidazo[2,1-b][1,3,4]thiadiazol-5-yl]-N,N-dimethyl-benzamide;
(81) (2-Methyl-benzyl)-(5-pyridin-3-yl-imidazo[2,1-b][1,3,4]thiadiazol-2-yl)-amine;
(82) [5-(3-Chloro-phenyl)-imidazo[2,1-b][1,3,4]thiadiazol-2-yl]-(4-fluoro-benzyl)-amine;

(83) N-{3-[2-(4-Dimethylamino-benzylamino)-imidazo[2,1-b][1,3,4]thiadiazol-5-yl]-phenyl}-acetamide;
(84) Isobutyl-(5-pyridin-3-yl-imidazo[2,1-b][1,3,4]thiadiazol-2-yl)-amine;
(85) (5-Naphthalen-2-yl-imidazo[2,1-b][1,3,4]thiadiazol-2-yl)-(2-pyridin-2-yl-ethyl)-amine;
(86) Cyclopropylmethyl-(5-pyridin-3-yl-imidazo[2,1-b][1,3,4]thiadiazol-2-yl)-amine;
(87) [5-(2-Chloro-phenyl)-imidazo[2,1-b][1,3,4]thiadiazol-2-yl]-(2-pyridin-2-yl-ethyl)amine;
(88) 4-{2-[(Furan-2-ylmethyl)-amino]-imidazo[2,1-b][1,3,4]thiadiazol-5-yl}-2,6-dimethyl-phenol;
(89) Cyclopropylmethyl-(5-phenyl-imidazo[2,1-b][1,3,4]thiadiazol-2-yl)-amine;
(90) Benzyl-(5-pyridin-3-yl-imidazo[2,1-b][1,3,4]thiadiazol-2-yl)-amine;
(91) Isobutyl-(5-phenyl-imidazo[2,1-b][1,3,4]thiadiazol-2-yl)-amine;
(92) Benzyl-[5-(6-methoxy-pyridin-3-yl)-imidazo[2,1-b][1,3,4]thiadiazol-2-yl]-amine;
(93) Cyclopropylmethyl-(5-pyridin-4-yl-imidazo[2,1-b][1,3,4]thiadiazol-2-yl)-amine;
(94) (4-Fluoro-benzyl)[5-(5-methoxy-pyridin-3-yl)-imidazo[2,1-b][1,3,4]thiadiazol-2-yl]-amine;
(95) 4-[2-(Cyclopropylmethyl-amino)-imidazo[2,1-b][1,3,4]thiadiazol-5-yl]-N-(2-hydroxy-ethyl)-benzamide;
(96) (4-Methoxy-benzyl)-(5-pyridin-4-yl-imidazo[2,1-b][1,3,4]thiadiazol-2-yl)-amine;
(97) [5-(2-Chloro-phenyl)-imidazo[2,1-b][1,3,4]thiadiazol-2-yl]-cyclopropylmethyl-amine;
(98) 1-(3-{2-[(Benzo[1,3]dioxol-5-ylmethyl)-amino]-imidazo[2,1-b][1,3,4]thiadiazol-5-yl}-phenyl)-ethanone;
(99) Furan-2-ylmethyl-[5-(1-methyl-1H-pyrazol-4-yl)-imidazo[2,1-b][1,3,4]thia-diazol-2-yl]-amine;
(100) (4-Fluoro-benzyl)-(5-naphthalen-2-yl-imidazo[2,1-b][1,3,4]thiadiazol-2-yl)-amine;
(101) [5-(3,4-Dimethoxy-phenyl)-imidazo[2,1-b][1,3,4]thiadiazol-2-yl]-isobutyl-amine;
(102) [5-(2-Chloro-phenyl)-imidazo[2,1-b][1,3,4]thiadiazol-2-yl]-isobutyl-amine;
(103) N-(2-Hydroxy-ethyl)-4-{2-[(tetrahydro-pyran-4-ylmethyl)-amino]-imidazo[2,1-b][1,3,4]thiadiazol-5-yl}-benzamide;
(104) Cyclohexyl-(5-pyridin-3-yl-imidazo[2,1-b][1,3,4]thiadiazol-2-yl)-amine;
(105) (5-Naphthalen-2-yl-imidazo[2,1-b][1,3,4]thiadiazol-2-yl)-thiophen-2-ylmethylamine;
(106) [5-(5-Methoxy-pyridin-3-yl)-imidazo[2,1-b][1,3,4]thiadiazol-2-yl]-thiophen-2-ylmethyl-amine;
(107) [5-(6-Methoxy-pyridin-3-yl)-imidazo[2,1-b][1,3,4]thiadiazol-2-yl]-thiophen-2-ylmethyl-amine;
(108) Benzo[1,3]dioxol-5-ylmethyl-(5-pyridin-3-yl-imidazo[2,1-b][1,3,4]thiadiazol-2-yl)-amine;
(109) Benzo[1,3]dioxol-5-ylmethyl-[5-(4-chloro-phenyl)-imidazo[2,1-b][1,3,4]thia-diazol-2-yl]-amine;
(110) [5-(4-Chloro-phenyl)-imidazo[2,1-b][1,3,4]thiadiazol-2-yl]-(4-fluoro-benzyl)-amine;
(111) 1-{3-[2-(4-Methoxy-benzylamino)-imidazo[2,1-b][1,3,4]thiadiazol-5-yl]-phenyl}ethanone;
(112) (2-Methoxy-ethyl)-(5-thiophen-3-yl-imidazo[2,1-b][1,3,4]thiadiazol-2-yl)-amine;
(113) Benzyl-[5-(5-methoxy-pyridin-3-yl)-imidazo[2,1-b][1,3,4]thiadiazol-2-yl]-amine.

Example 35

The following examples are also prepared in accordance with the methods described herein.

2-[5-(3-Trifluoromethyl-phenyl)-imidazo[2,1-b][1,3,4]thiadiazol-2-ylamino]-acetamide;
[5-(3-Cyano-phenyl)-imidazo[2,1-b][1,3,4]thiadiazol-2-ylamino]-acetic acid;
2-[5-(3-Fluoro-phenyl)-imidazo[2,1-b][1,3,4]thiadiazol-2-ylamino]-acetamide;
(2-Piperidin-1-yl-ethyl)[5-(3-trifluoromethoxy-phenyl)-imidazo[2,1-b][1,3,4]thiadiazol-2-yl]-amine;
4-[5-(3-Trifluoromethyl-phenyl)-imidazo[2,1-b][1,3,4]thiadiazol-2-ylamino]-cyclohexanol;
[5-(3,5-Difluoro-phenyl)-imidazo[2,1-b][1,3,4]thiadiazol-2-yl]-(2-morpholin-4-yl-ethyl)-amine;
Cyclopropylmethyl-(5-phenyl-imidazo[2,1-b][1,3,4]thiadiazol-2-yl)-amine;
4-(2-Phenylsulfanyl-imidazo[2,1-b][1,3,4]thiadiazol-5-ylamino)-benzonitrile;
(3-Fluoro-phenyl)-(2-phenoxy-imidazo[2,1-b][1,3,4]thiadiazol-5-yl)-amine;
(2-Methoxy-imidazo[2,1-b][1,3,4]thiadiazol-5-yl)-(3-trifluoromethyl-Phenyl)-amine;
Cyclopropylmethyl-[5-(4-trifluoromethyl-phenyl)-imidazo[2,1-b][1,3,4]thiadiazol-2-yl]-amine;
4-[(5-Naphthalen-2-yl-imidazo[2,1-b][1,3,4]thiadiazol-2-ylamino)-methyl]-benzenesulfonamide;
4-[2-(3-Hydroxy-propylamino)-imidazo[2,1-b][1,3,4]thiadiazol-5-yl]-benzonitrile;
[5-(3-Amino-phenyl)-imidazo[2,1-b][1,3,4]thiadiazol-2-yl]-[2-(5-methyl-1H-pyrazol-4-yl)-ethyl]-amine;
3-[2-(2-Pyrazin-2-yl-ethylamino)-imidazo[2,1-b][1,3,4]thiadiazol-5-yl]-benzoic acid;
1-(3-{2-[(Furan-2-ylmethyl)-amino]-imidazo[2,1-b][1,3,4]thiadiazol-5-yl}-phenyl)-ethanone;
[5-(3-Chloro-4-fluoro-phenyl)-imidazo[2,1-b][1,3,4]thiadiazol-2-yl]-(1H-pyrrol-2-ylmethyl)-amine;
2-[5-(3-Chloro-4-fluoro-phenyl)-imidazo[2,1-b][1,3,4]thiadiazol-2-ylamino]-ethanol;
2-(5-Naphthalen-2-yl-imidazo[2,1-b][1,3,4]thiadiazol-2-ylamino)-ethanol;
1-{2-[5-(3-Methanesulfonyl-phenyl)-imidazo[2,1-b][1,3,4]thiadiazol-2-ylamino]-ethyl}-imidazolidin-2-one;
(3-Imidazol-1-yl-propyl)[5-(4-trifluoromethoxy-phenyl)-imidazo[2,1-b][1,3,4]-thiadiazol-2-yl]-amine;
4-[2-(4-Fluoro-benzylamino)-imidazo[2,1-b][1,3,4]thiadiazol-5-yl]-phenol;
(E)-3-(4-{2-[(Furan-2-ylmethyl)-amino]-imidazo[2,1-b][1,3,4]thiadiazol-5-yl}-phenyl)-acrylic acid;
(E)-3-{-4-[2-((S)-1-Hydroxymethyl-2-methyl-propylamino)-imidazo[2,1-b][1,3,4]thiadiazol-5-yl]-phenyl}-acrylic acid;
4-[2-(4-Methoxy-benzylamino)-imidazo[2,1-b][1,3,4]thiadiazol-5-yl]-benzoic acid;
4-[2-(3,4-Dichloro-benzylamino)-imidazo[2,1-b][1,3,4]thiadiazol-5-yl]-benzoic acid;
4-{2-[(Furan-2-ylmethyl)-amino]-imidazo[2,1-b][1,3,4]thiadiazol-5-yl}-benzoic acid;
[5-(1-Methyl-1H-pyrazol-4-yl)-imidazo[2,1-b][1,3,4]thiadiazol-2-yl]-thiophen-2-ylmethyl-amine;
(E)-3-[4-(2-Propylamino-imidazo[2,1-b][1,3,4]thiadiazol-5-yl)-phenyl]-acrylic acid;
(E)-3-{4-[2-(3,4-Dichloro-benzylamino)-imidazo[2,1-b][1,3,4]thiadiazol-5-yl]-phenyl}-acrylic acid;
4-[2-(3-Chloro-benzylamino)-imidazo[2,1-b][1,3,4]thiadiazol-5-yl]-benzoic acid;
(E)-3-{4-[2-(Cyclopropylmethyl-amino)-imidazo[2,1-b][1,3,4]thiadiazol-5-yl]-phenyl}-acrylic acid;
(4-Fluoro-benzyl)-[5-(1H-indol-5-yl)-imidazo[2,1-b][1,3,4]thiadiazol-2-yl]-amine;

Cyclopropylmethyl-[5-(1H-indol-5-yl)-imidazo[2,1-b][1,3,4]thiadiazol-2-yl]-amine;
[5-(4-Amino-phenyl)-imidazo[2,1-b][1,3,4]thiadiazol-2-yl]-pyridin-3-ylmethyl-amine;
(E)-3-(4-{2-[(Pyridin-3-ylmethyl)-amino]-imidazo[2,1-b][1,3,4]thiadiazol-5-yl}-phenyl)-acrylic acid;
4-{[2-(Cyclopropylmethyl-amino)-imidazo[2,1-b][1,3,4]thiadiazole-5-carbonyl]-amino}-benzoic acid;
2-(Cyclopropylmethyl-amino)-imidazo[2,1-b][1,3,4]thiadiazole-5-carboxylic acid (3-acetyl-phenyl)-amide;
Ethanesulfonic acid [2-(3,4-dichloro-benzylamino)-imidazo[2,1-b][1,3,4]thia-diazol-5-yl]-amide;
(4-Methoxy-benzyl)-(5-phenylethynyl-imidazo[2,1-b][1,3,4]thiadiazol-2-yl)-amine;
4-[(5-Cyclohexyl-imidazo[2,1-b][1,3,4]thiadiazol-2-ylamino)-methyl]-benzenesulfonamide;
4-[2-(3,4-Dichloro-benzylamino)-6-methyl-imidazo[2,1-b][1,3,4]thiadiazol-5-yl]-benzoic acid;
2-(6-Fluoro-5-naphthalen-2-yl-imidazo[2,1-b][1,3,4]thia-diazol-2-ylamino)-ethanol;
3-Acetylamino-N-[2-(3,4-dichloro-benzylamino)-imidazo[2,1-b][1,3,4]thiadiazol-5-yl]-propionamide;
{[2-(3,4-Dichloro-benzylamino)-6-methyl-imidazo[2,1-b][1,3,4]thiadiazole-5-carbonyl]-amino}-acetic acid;
4-[2-(3-Chloro-benzoylamino)-imidazo[2,1-b][1,3,4]thia-diazol-5-yl]-benzoic acid;
4-[2-(Methylcarbamoylmethyl-amino)-imidazo[2,1-b][1,3,4]thiadiazol-5-yl]-benzoic acid;
N-[5-(3-Acetyl-phenyl)-imidazo[2,1-b][1,3,4]thiadiazol-2-yl]-propionamide;
2-[5-(4-Chloro-phenyl)-imidazo[2,1-b][1,3,4]thiadiazol-2-yloxy]-N-methyl-acetamide;
4-(2-Phenylethynyl-imidazo[2,1-b][1,3,4]thiadiazol-5-yl)-benzoic acid;
3-[2-(3-Chloro-phenyl)-imidazo[2,1-b][1,3,4]thiadiazol-5-ylamino]-benzoic acid;
1-{4-[5-(4-Methoxy-benzylamino)-imidazo[2,1-b][1,3,4]thiadiazol-2-yl]-phenyl}-ethanone;
[2-(3,4-Dimethoxy-phenyl)-imidazo[2,1-b][1,3,4]thiadiazol-5-yl]-(tetrahydro-pyran-4-yl)-amine;
[5-(5-Methoxy-pyridin-3-yl)-imidazo[2,1-b][1,3,4]thiadiazol-2-yl]-(tetrahydro-pyran-4-yl)-amine;
4-[2-(Tetrahydro-pyran-4-ylamino)-imidazo[2,1-b][1,3,4]thiadiazol-5-yl]-benzoic acid;
[5-(1H-Indol-2-yl)-imidazo[2,1-b][1,3,4]thiadiazol-2-yl]-(tetrahydro-pyran-4-yl)-amine;
[5-(3,4-Dimethoxy-phenyl)-imidazo[2,1-b][1,3,4]thiadiazol-2-yl]-(tetrahydro-pyran-4-yl)-amine;
2-[5-(3,4-Dimethoxy-phenyl)-imidazo[2,1-b][1,3,4]thiadiazol-2-ylamino]-butan-1-ol;
[5-(3,4-Dimethoxy-phenyl)-imidazo[2,1-b][1,3,4]thiadiazol-2-yl]-propyl-amine;
4-{[5-(6-Methoxy-pyridin-3-yl)-imidazo[2,1-b][1,3,4]thiadiazol-2-ylamino]-methyl}-benzenesulfonamide;
2-(4-Chloro-3-fluoro-benzyloxy)-5-morpholin-4-yl-imidazo[2,1-b][1,3,4]thiadiazole;
[5-(3-Chloro-4-fluoro-phenoxy)-imidazo[2,1-b][1,3,4]thia-diazol-2-yl]-(2,2-dimethyl-propyl)-amine;

Example 36

Compounds of the examples were tested in the biological tests described above and were found to exhibit 50% inhibition of PIM-1 or PIM-2 (as appropriate) at a concentration of 50 μM or below (e.g. at a concentration of 10 μM).

For example, the following representative compounds of the examples exhibited the following approximate percentage of PIM-1 inhibition at a concentration of 10 μM.

| Ex. | Percentage Inhibition of PIM-1 at 10 μM |
|---|---|
| 4 | 83 |
| 15 | 89 |
| 18 | 82 |
| 34(3) | 97 |
| 34(4) | 71 |
| 34(5) | 98 |
| 34(8) | 98 |
| 34(10) | 77 |
| 34(12) | 58 |
| 34(14) | 96 |
| 34(16) | 99 |
| 34(22) | 82 |
| 34(33) | 84 |
| 34(39) | 82 |
| 34(40) | 100 |
| 34(57) | 73 |
| 34(58) | 97 |
| 34(65) | 77 |

The invention claimed is:
1. A compound of formula I,

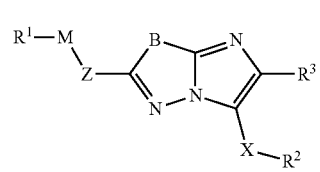

wherein:
B represents —S—, —S(O)— or —SO$_2$—;
Z represents a direct bond, —(CH$_2$)$_n$—O—, —(CH$_2$)$_n$—S—, —(CH$_2$)$_n$—N(R$^a$)—, —(CH$_2$)$_{n1}$—S(O)—, —(CH$_2$)$_n$—SO$_2$—, —(CH$_2$)$_n$—NH—SO$_2$—, —(CH$_2$)$_{n1}$—SO$_2$—NH—, —(CH$_2$)$_n$—N(R$^a$)—CO—, —(CH$_2$)$_n$—NH—CO—NH— or —(CH$_2$)$_n$—CO—N(R$^a$)—;
n represents, on each occasion when used herein, 0, 1 or 2;
n1 represents, on each occasion when used herein, 1 or 2;
M represents a direct bond;
R$^1$ represents aryl where the aryl is optionally substituted with one or more substituents selected from B$^3$;
X represents a direct bond;
R$^2$ represents -T-Q;
T represents a direct bond;
Q represents C$_{3-6}$ heterocycloalkyl where the heterocycloalkyl group is optionally substituted by one or more substituents selected from B$^6$, or heteroaryl where the heteroaryl group is optionally substituted by one or more substituents selected from B$^8$;
B$^3$, B$^6$, and B$^8$ independently represent halo, —OR$^e$, —C(O)$_2$R$^e$, —C(O)R$^e$, —C(O)N(R$^e$)$_2$, —N(R$^e$)—C(O)—R$^e$, —CN, —S(O)$_2$R$^e$, —S(O)$_2$N(R$^e$)$_2$, —N(R$^e$)$_2$ and/or C$_{1-4}$ alkyl optionally substituted by one or more substituents selected from halo, —OR$^e$ and —C(O)$_2$R$^e$; or,
B$^6$ may alternatively and independently represent =O;
R$^3$ represents hydrogen, halo, —R$^f$, —OR$^f$, —SR$^f$, cyano or —N(R$^f$)$_2$;
R$^a$, R$^e$ and R$^f$ represent independently, on each occasion when used herein, hydrogen, phenyl optionally substituted by one or more halo and/or $C_{1-3}$ alkyl substituents and/or $C_{1-4}$ alkyl optionally substituted with one or more substituents selected from halo, —$OR^h$ and —$N(R^h)_2$;

$R^h$ represents, on each occasion when used herein, hydrogen or $C_{1-3}$ alkyl optionally substituted by one or more halo atoms, or a pharmaceutically acceptable ester, amide, solvate or salt thereof, provided that when B represents —S—,
X, Z and M all represent direct bonds, $R^3$ represents hydrogen, then $R^2$ does not represent 1-piperidinyl when $R^1$ represents unsubstituted phenyl.

2. A pharmaceutical composition comprising a compound of formula I together with a pharmaceutically acceptable adjuvant, diluent or carrier,

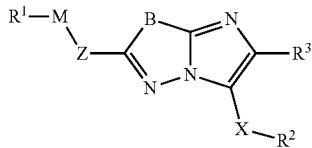

wherein:

B represents —S—, —S(O)— or —$SO_2$—;

Z represents a direct bond, —$(CH_2)_n$—O—, —$(CH_2)_n$—S—, —$(CH_2)_n$—$N(R^a)$—, —$(CH_2)_{n1}$—S(O)—, —$(CH_2)_n$—$SO_2$—, —$(CH_2)_n$—NH—$SO_2$—, —$(CH_2)_{n1}$—$SO_2$—NH—, —$(CH_2)_n$—$N(R^a)$—CO—, —$(CH_2)_n$—NH—CO—NH— or —$(CH_2)_n$—CO—N$(R^a)$—;

n represents, on each occasion when used herein, 0, 1 or 2;

n1 represents, on each occasion when used herein, 1 or 2;

M represents a direct bond;

$R^1$ represents aryl where the aryl is optionally substituted with one or more substituents selected from $B^3$;

X represents a direct bond;

$R^2$ represents -T-Q;

T represents a direct bond;

Q represents $C_{3-6}$ heterocycloalkyl where the heterocycloalkyl group is optionally substituted by one or more substituents selected from $B^6$, or heteroaryl where the heteroaryl group is optionally substituted by one or more substituents selected from and $B^8$, respectively;

$B^3$, $B^6$, and $B^8$ independently represent halo, —$OR^e$, —$C(O)_2R^e$, —$C(O)R^e$, —$C(O)N(R^e)_2$, —$N(R^e)$—C(O)—$R^e$, —CN, —$S(O)_2R^e$, —$S(O)_2N(R^e)_2$, —$N(R^e)_2$ and/or $C_{1-4}$ alkyl optionally substituted by one or more substituents selected from halo, —$OR^e$ and —$C(O)_2R^e$; or, $B^6$ may alternatively and independently represent =O;

$R^3$ represents hydrogen, halo, —$R^f$, —$OR^f$, —$SR^f$, cyano or —$N(R^f)_2$;

$R^a$, $R^e$ and $R^f$ represent independently, on each occasion when used herein, hydrogen, phenyl optionally substituted by one or more halo and/or $C_{1-3}$ alkyl substituents and/or $C_{1-4}$ alkyl optionally substituted with one or more substituents selected from halo, —$OR^h$ and —$N(R^h)_2$;

$R^h$ represents, on each occasion when used herein, hydrogen or $C_{1-3}$ alkyl optionally substituted by one or more halo atoms, or a pharmaceutically acceptable ester, amide, solvate or salt thereof.

3. A compound as claimed in claim 1, wherein:

$B^3$, $B^6$, and $B^8$ independently represent halo, —$OR^e$, —$C(O)_2R^e$, —$C(O)R^e$, —$C(O)N(R^e)_2$, —CN, —$S(O)_2R^e$, —$S(O)_2N(R^e)_2$, —$N(R^e)_2$ and/or $C_{1-4}$ alkyl optionally substituted by one or more substituents selected from halo, —$OR^e$ and —$C(O)_2R^e$; or, $B^6$ may alternatively and independently represent =O;

$R^a$, $R^e$ and $R^f$ represent independently, on each occasion when used herein, hydrogen and/or $C_{1-4}$ alkyl optionally substituted with one or more substituents selected from halo and —$OR^h$;

when Z represents —$(CH_2)_n$—$N(R^a)$—CO—, then $R^a$ represents hydrogen.

4. A compound as claimed in claim 1, wherein Z represents a direct bond, —O—, —S—, —$(CH_2)_n$—$N(R^a)$— or —$(CH_2)_n$—N(H)—C(O)—.

5. A compound as claimed in claim 1, wherein $R^a$ represents H.

6. A compound as claimed in claim 1, wherein n represents 0.

7. A compound as claimed in claim 1, wherein $B^3$, $B^6$ and $B^8$ independently represent halo, —$OR^e$, —$C(O)_2R^e$, —$C(O)R^e$, —CN, —$S(O)_2R^e$, —$S(O)_2N(R^e)_2$, —$N(R^e)_2$ and/or $C_{1-3}$ alkyl, which alkyl group is optionally substituted by one or more substituents selected from halo, —$OR^e$ or —$C(O)_2R^e$, or $B^6$ may alternatively and independently represent =O.

8. A compound as claimed in claim 1, wherein $R^a$, $R^e$ and $R^f$ independently represent hydrogen or $C_{1-3}$ alkyl optionally substituted by one or more halo atoms.

9. A compound as claimed in claim 1, wherein $R^h$ represents H or $C_{1-2}$ alkyl.

10. A compound as claimed in claim 1, wherein $R^3$ represents hydrogen, $C_{1-2}$ alkyl or fluoro.

11. A pharmaceutical formulation including a compound of claim 1, or a pharmaceutically acceptable ester, amide, solvate or salt thereof, in admixture with a pharmaceutically acceptable adjuvant, diluent or carrier.

12. A combination product comprising:

(A) a compound of formula I, or a pharmaceutically-acceptable ester, amide, solvate or salt thereof; and (B) another therapeutic agent that is useful in the treatment of in the treatment of cancer and/or a proliferative disease, wherein each of components (A) and (B) is formulated in admixture with a pharmaceutically-acceptable adjuvant, diluent or carrier, where the compound of formula 1 is

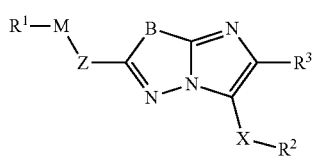

wherein:

B represents —S—, —S(O)— or —$SO_2$—;

Z represents a direct bond, —$(CH_2)_n$—O—, —$(CH_2)_n$—S—, —$(CH_2)_n$—$N(R^a)$—, —$(CH_2)_{n1}$—S(O)—, —$(CH_2)_n$—$SO_2$—, —$(CH_2)_n$—NH—$SO_2$—, —$(CH_2)_{n1}$—$SO_2$—NH—, —$(CH_2)_n$—$N(R^a)$—CO—, —$(CH_2)_n$—NH—CO—NH— or —$(CH_2)_n$—CO—N$(R^a)$—;

n represents, on each occasion when used herein, 0, 1 or 2;
n1 represents, on each occasion when used herein, 1 or 2;
M represents a direct bond
$R^1$ represents aryl where the aryl is optionally substituted with one or more substituents selected from $B^3$;
X represents a direct bond;
$R^2$ represents -T-Q;
T represents a direct bond;
Q represents $C_{3-6}$ heterocycloalkyl where the heterocycloalkyl group is optionally substituted by one or more substituents selected from $B^6$, or heteroaryl where the heteroaryl group is optionally substituted by one or more substituents selected from $B^8$;
$B^3$, $B^6$, and $B^8$ independently represent halo, —$OR^e$, —$C(O)_2R^e$, —$C(O)R^e$, —$C(O)N(R^e)_2$, —$N(R^e)$—C(O)—$R^e$, —CN, —$S(O)_2R^e$, —$S(O)_2N(R^e)_2$, —$N(R^e)_2$ and/or $C_{1-4}$ alkyl optionally substituted by one or more substituents selected from halo, —$OR^e$ and —$C(O)_2R^e$; or,
$B^6$ may alternatively and independently represent =O;
$R^3$ represents hydrogen, halo, —$R^f$, —$OR^f$, —$SR^f$, cyano or —$N(R^f)_2$;
$R^a$, $R^e$ and $R^f$ represent independently, on each occasion when used herein, hydrogen, phenyl optionally substituted by one or more halo and/or $C_{1-3}$ alkyl substituents and/or $C_{1-4}$ alkyl optionally substituted with one or more substituents selected from halo, —$OR^h$ and —$N(R^h)_2$;
$R^h$ represents, on each occasion when used herein, hydrogen or $C_{1-3}$ alkyl optionally substituted by one or more halo atoms,
or a pharmaceutically acceptable ester, amide, solvate or salt thereof.

13. A combination product as claimed in claim 12 wherein the compound of formula 1 is formulated as a pharmaceutical formulation with a pharmaceutically-acceptable adjuvant, diluent, or carrier.

14. A combination product as claimed in claim 12 which comprises a kit of parts comprising components:
(a) a pharmaceutical formulation including a compound of formula I as defined in claim 12, or a pharmaceutically-acceptable ester, amide, solvate or salt thereof, in admixture with a pharmaceutically-acceptable adjuvant, diluent or carrier; and
(b) a pharmaceutical formulation including another therapeutic agent that is useful in the treatment of cancer and/or a proliferative disease in admixture with a pharmaceutically-acceptable adjuvant, diluent or carrier,
which components (a) and (b) are each provided in a form that is suitable for administration in conjunction with the other.

15. A compound as claimed in claim 2, wherein:
$B^3$, $B^6$, and $B^8$ independently represent halo, —$OR^e$, —$C(O)_2R^e$, —$C(O)R^e$, —$C(O)N(R^e)_2$, —CN, —$S(O)_2R^e$, —$S(O)_2N(R^e)_2$, —$N(R^e)_2$ and/or $C_{1-4}$ alkyl optionally substituted by one or more substituents selected from halo, —$OR^e$ and —$C(O)_2R^e$; or,
$B^6$ may alternatively and independently represent =O;
$R^a$, $R^e$ and $R^f$ represent independently, on each occasion when used herein, hydrogen, and/or $C_{1-4}$ alkyl optionally substituted with one or more substituents selected from halo, —$OR^h$;
when Z represents —$(CH_2)_n$—$N(R^a)$—CO—, then $R^a$ represents hydrogen.

16. A compound as claimed in claim 2, wherein Z represents a direct bond, —O—, —S—, —$(CH_2)_n$—$N(R^a)$— or —$(CH_2)_n$—N(H)—C(O)—.

17. A compound as claimed in claim 2, wherein $R^a$ represents H.

18. A compound as claimed in claim 2, wherein n represents 0.

19. A compound as claimed in claim 2, wherein $B^3$, $B^6$ and $B^8$ independently represents halo, —$OR^e$, —$C(O)_2R^e$, —$C(O)R^e$, —CN, —$S(O)_2R^e$, —$S(O)_2N(R^e)_2$, —$N(R^e)_2$ and/or $C_{1-3}$ alkyl, which alkyl group is optionally substituted by one or more substituents selected from halo, —$OR^e$ or —$C(O)_2R^e$ or $B^6$ may alternatively represent =O.

20. A compound as claimed in claim 2, wherein $R^a$, $R^e$ and $R^f$ independently represent hydrogen or $C_{1-3}$ alkyl optionally substituted by one or more halo atoms.

21. A compound as claimed in claim 2, wherein $R^h$ represents H or $C_{1-2}$ alkyl.

22. A compound as claimed in claim 2, wherein $R^3$ represents hydrogen, $C_{1-2}$ alkyl or fluoro.

* * * * *

UNITED STATES PATENT AND TRADEMARK OFFICE
CERTIFICATE OF CORRECTION

PATENT NO. : 8,563,550 B2  
APPLICATION NO. : 12/679514  
DATED : October 22, 2013  
INVENTOR(S) : Pevarello et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 678 days.

Signed and Sealed this

Fifteenth Day of September, 2015

Michelle K. Lee  
*Director of the United States Patent and Trademark Office*

UNITED STATES PATENT AND TRADEMARK OFFICE
CERTIFICATE OF CORRECTION

PATENT NO. : 8,563,550 B2
APPLICATION NO. : 12/679514
DATED : October 22, 2013
INVENTOR(S) : Paolo Pevarello et al.

It is certified that error appears in the above-identified patent and that said Letters Patent is hereby corrected as shown below:

On the title page, column 1: Delete item "(73) Assignee: Centro Nacional de Investigaciones Oncologicas (CNIO)" and replace it with --(73) Assignee: Fundacion Centro Nacional de Investigaciones Oncologicas Carlos III--

Signed and Sealed this
Twenty-eighth Day of June, 2016

Michelle K. Lee
*Director of the United States Patent and Trademark Office*